United States Patent
Fink et al.

(10) Patent No.: US 7,141,571 B2
(45) Date of Patent: Nov. 28, 2006

(54) PYRROLOTRIAZINE COMPOUNDS AS KINASE INHIBITORS

(75) Inventors: Brian E. Fink, Princeton Junction, NJ (US); Ashvinikumar V. Gavai, Princeton Junction, NJ (US); Gregory D. Vite, Titusville, NJ (US); Ping Chen, Belle Mead, NJ (US); Harold Mastalerz, Guilford, CT (US); Derek J. Norris, Pennington, NJ (US); John S. Tokarski, Princeton, NJ (US); Yufen Zhao, Pennington, NJ (US); Wen-Ching Han, Newton, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 15 days.

(21) Appl. No.: 11/019,901

(22) Filed: Dec. 22, 2004

(65) Prior Publication Data

US 2005/0182058 A1   Aug. 18, 2005

Related U.S. Application Data

(60) Provisional application No. 60/533,335, filed on Dec. 29, 2003.

(51) Int. Cl.
C07D 487/04 (2006.01)
A61K 31/53 (2006.01)

(52) U.S. Cl. .................. 514/243; 544/183
(58) Field of Classification Search ............... 544/183; 514/243
See application file for complete search history.

(56) References Cited

U.S. PATENT DOCUMENTS

| | | |
|---|---|---|
| 6,670,357 B1 | 12/2003 | Leftheris et al. |
| 6,787,545 B1 | 9/2004 | Ohtani et al. |
| 6,867,300 B1 | 3/2005 | Godfrey, Jr. et al. |
| 6,869,952 B1 | 3/2005 | Bhide et al. |
| 6,908,916 B1 | 6/2005 | Mastalerz et al. |
| 6,916,815 B1 | 7/2005 | Vite et al. |
| 2003/0232832 A1 | 12/2003 | Lombardo et al. |
| 2003/0232861 A1 | 12/2003 | Dyckman et al. |
| 2004/0063707 A1 | 4/2004 | Bhide et al. |
| 2004/0063708 A1 | 4/2004 | Bhide et al. |
| 2004/0077858 A1 | 4/2004 | Bhide et al. |
| 2004/0229877 A1 | 11/2004 | Leftheris et al. |

FOREIGN PATENT DOCUMENTS

| | | |
|---|---|---|
| EP | 0 713 876 | 5/1996 |
| WO | WO 98/08847 | 3/1998 |
| WO | WO 00/71129 | 11/2000 |
| WO | WO 02/40486 | 5/2002 |
| WO | WO 03/090912 | 11/2003 |
| WO | WO 2004/009784 | 1/2004 |

OTHER PUBLICATIONS

Tsi-Ping et al., TIPS 16:5766, 1995.*
U.S. Appl. No. 60/620,784, filed Oct. 21, 2004, Gavai et al.
U.S. Appl. No. 11/152,650, filed Jun. 14, 2005, Cai et al.
U.S. Appl. No. 11/157,460, filed Jun. 21, 2005, Gavai et al.
U.S. Appl. No. 11/008,719, filed Dec. 9, 2004, Swaminathan et al.
U.S. Appl. No. 11/019,899, filed Dec. 22, 2004, Gavai et al.
Ewald, H. et al., "Reaktionen von 1,2,4-Triazinen mit Acetylendicarbonsäure-dimethylester", Liebigs Ann. Chem., pp. 1718-1724 (1977).
Hunt, J.T. et al., "Discovery of the Pyrrolo[2,1-f][1,2,4]triazine Nucleus as a New Kinase Inhibitor Template", J. Med. Chem., vol. 47, No. 16, pp. 4054-4059 (2004).
Migliara, O. et al., "Synthesis of a New Bridgehead Nitrogen Heterocyclic System. Pyrrolo[2,1-f]-1,2,4—triazine Derivatives", J. Heterocyclic Chem., vol. 16, pp. 833-834 (1979).
Neunhoeffer, H. et al., "Cycloadditionen mit Methoxy- und Dialkylamino-1,2,4-triazinen", Liebigs Ann. Chem., pp. 1413-1420 (1977).
Patil, S.A. et al., "Synthesis of Pyrrolo[2,1-f][1,2,4]triazine Congeners of Nucleic Acid Purines via the N-Amination of 2-Substituted Pyrroles", J. Heterocyclic Chem., vol. 31, pp. 781-786 (1994).
Quintela, J.M. et al., "A Ready One-pot Preparation for Pyrrolo[2,1-f][1,2,4]triazine and Pyrazolo[5,1-c]pyrimido[4,5-e]-[1,2,4]traizine Derivatives", Tetrahedron, vol. 52, No. 8, pp. 3037-3048 (1996).

* cited by examiner

*Primary Examiner*—Venkataraman Balasubramanian
(74) *Attorney, Agent, or Firm*—Elliot Korsen

(57) ABSTRACT

The present invention provides compounds of formula I

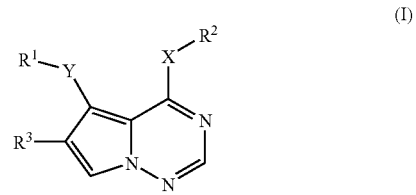

and pharmaceutically acceptable salts thereof.

The formula I compounds inhibit tyrosine kinase activity of growth factor receptors such as HER1, HER2 and HER4 thereby making them useful as antiproliferative agents. The formula I compounds are also useful for the treatment of other diseases associated with signal transduction pathways operating through growth factor receptors.

4 Claims, 2 Drawing Sheets

X-ray structure of HER1, color-coded by key elements of a typical kinase.

X-ray structure of CDK2 complexed with ATP. Different regions of a typical ATP-binding site are delineated.

PYRROLOTRIAZINE COMPOUNDS AS KINASE INHIBITORS

This application claims priority from U.S. Provisional Application No. 60/533,335 filed Dec. 29, 2003, the disclosures of which are incorporated herein by reference in their entirety.

FIELD OF THE INVENTION

This invention relates to compounds that inhibit the tyrosine kinase activity of growth factor receptors such as HER1, HER2, and HER4 thereby making them useful as anti-cancer agents. The compounds are also useful in the treatment of diseases, other than cancer, which are associated with signal transduction pathways operating through growth factor receptors such as HER1, HER2 and HER4.

BACKGROUND OF THE INVENTION

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain.

The human epidermal growth factor receptor (HER) family consists of four distinct receptor tyrosine kinases referred to HER1, HER2, HER3, and HER4. These kinases are also referred to as erbB1, erbB2, etc. HER1 is also commonly referred to as the epidermal growth factor (EGF) receptor. With the exception of HER3, these receptors have intrinsic protein kinase activity that is specific for tyrosine residues of phosphoacceptor proteins. The HER kinases are expressed in most epithelial cells as well as tumor cells of epithelial origin. They are also often expressed in tumor cells of mesenchymal origin such as sarcomas or rhabdomyosarcomas. RTKs such as HER1 and HER2 are involved in cell proliferation and are associated with diseases such as psoriasis and cancer. Disruption of signal transduction by inhibition of these kinases would have an antiproliferative and therapeutic effect.

The enzymatic activity of receptor tyrosine kinases can be stimulated by either overexpression, or by ligand-mediated dimerization. The formation of homodimers as well as heterodimers has been demonstrated for the HER receptor family. An example of homodimerization is the dimerization of HER1 (EGF receptor) by one of the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization as involving HER2 and HER3, or a HER3/HER4 combination, results in a significant stimulation of the tyrosine kinase activity of the receptor dimers even though one of the receptors (HER3) is enzymatically inert. The kinase activity of HER2 has been shown to be activated also by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase ) and the phosphatidylinositol 3-kinase (PI3 kinase). Activation of these pathways have been shown to lead to cell proliferation and the inhibition of apoptosis. Inhibition of HER kinase signaling has been shown to inhibit cell proliferation and survival.

All protein kinases contain a structurally conserved catalytic domain of approximately 250–300 amino acid residues[1]. FIG. 1 shows an X-ray structure of HER1[2] which encompasses the highly conserved features of all members of the protein kinase family. The protein kinase fold is separated into two subdomains, or lobes. The smaller N-terminal lobe, or N lobe, is composed of a five-stranded $\beta$ sheet and one prominent $\alpha$ helix, called helix $\alpha$C. The C lobe is larger and is predominantly helical. The two lobes are connected through a single polypeptide strand (the linker/hinge region), which acts as a hinge about which the two domains can rotate with respect to one other upon binding of ATP and/or substrate. ATP is bound in the deep cleft between the two lobes and sits beneath a highly conserved loop connecting strands $\beta1$ and $\beta2$. This phosphate binding loop, or P loop, contains a conserved glycine-rich sequence motif (GXGX$\phi$G) where $\phi$ is usually tyrosine or phenylalanine. The glycine residues allow the loop to approach the phosphates of ATP very closely and to coordinate them via backbone interactions. The conserved aromatic side chain caps the site of phosphate transfer. ATP is anchored to the enzyme via hydrogen bonds between its adenine moiety and the backbone atoms of the linker region, and the ribose ring to residues at the start of the C-terminal domain.

Optimal phosphotransfer requires the precise spatial arrangement of several catalytic residues that are absolutely conserved among all known kinases. Asp813 and Asn818 (HER1 numbering as given in reference 2 or numbered as Asp837 and Asn842 as found in REFSEQ: accession NM_005228) emanate from a highly conserved loop structure at the base of the active site, called the catalytic loop. Asp813 interacts with the attacking hydroxyl side chain of the substrate, while Asn818 engages in hydrogen bonding interactions that orient Asp813. Asn818 and another absolutely conserved catalytic residue, Asp831 (numbered as Asp855 as found in REFSEQ: accession NM_005228), are also required for the binding of two divalent metal cations involved in coordination of the triphosphate group.

Numerous structures of complexes with ATP, its analogs, or small-molecule inhibitors bound to different protein kinases have provided a clear description of the organization of the catalytic domain and the ATP-binding cleft and of the similarities and differences that exist within the binding region[3]. It is now clear that there are regions within the binding cleft that are not occupied by ATP, and that these show structural diversity between members of the kinase family. FIG. 2 shows the interactions of ATP with the hinge region of human cyclin-dependent kinase 2 (CDK2)[4]. The generic regions of all known kinase ATP binding sites are delineated in the figure as: (1) the adenine binding region; (2) the ribose pocket; (3) the phosphate binding pocket; (4) a mostly hydrophobic region 1, behind the adenine ring, and (5) region 2, a cleft or a tunnel adjacent to the ribose pocket and the N3 nitrogen of adenine which points towards a surface-exposed area of the kinase domain. The available structures of kinase/inhibitor complexes indicate that one can take advantage of the regions not occupied by ATP, e.g. regions 1 and 2, for increasing binding interactions and hence binding potency and potentially because of sequence differences between kinases in these regions also modulate selectivity.

A combination of crystallography, modeling, screening and medicinal chemistry efforts has led to the understanding of the binding mode of the pyrrolotriazine chemotype in the ATP binding site. Based on an X-ray crystal structure of the pyrrolotriazine chemotype inhibitor in VEGFR-2, it has been shown that the pyrrolotriazine ring binds in the adenine pocket and makes several key interactions with the hinge region similarly to ATP. In this binding mode, the C5 group is directed into the highly conserved ribose-phosphate pockets. The C4 group, depending on its chemical constituency, can be directed into the specificity region 1 and the C6 group is directed into the specificity region 2. Modeling of enumerated examples of this chemotype in HER1 shows that the C5 group claimed in this invention can at the least occupy the ribose-phosphate pocket and interact with at least one or more of the absolutely conserved residues involved in phosphate binding, e.g., Asn818 and Asp831 (HER1 numbering).

The conserved nature of the kinase catalytic core structure makes it an excellent target for the generic kinase inhibitor template afforded by the pyrrolotriazine ring and the C5 group. This template can be successfully derivatized to make specific and potent kinase ATP-competitive inhibitors by targeting the poorly conserved areas of the ATP-binding site.

It has surprisingly been found that compounds of the invention and other compounds such as those disclosed in U.S. Pat. Nos. 5,457,105, 5,616,582 and 5,770,599, which contain a small aniline derivative as the substituent off of the C4 position of the bicyclic ring, exhibit both HER1 and HER2 activity.

REFERENCES (1) S. K. Hanks and T. Hunter, Protein kinases 6. The eukaryotic protein kinase superfamily: kinase (catalytic) domain structure and classification. FASEB J. 9 (1995), pp. 576–596.
(2) PDB ID: 1M14 Stamos, J., Sliwkowski, M. X., Eigenbrot, C.: Structure of the Epidermal Growth Factor Receptor Kinase Domain Alone and in Complex with a 4-Anilinoquinazoline Inhibitor. J. Biol. Chem. 277 pp. 46265 (2002).
(3) H. M. Berman, J. Westbrook, Z. Feng, G. Gilliland, T. N. Bhat, H. Weissig, I. N. Shindyalov, P. E. Bourne. The Protein Data Bank. Nucleic Acids Research, 28 pp. 235–242 (2000): website: http://www.pdb.org/.
(4) PDB ID: 1HCK Schulze-Gahmen, U., De Bondt, H. L., Kim, S. H.: High-resolution crystal structures of human cyclin-dependent kinase 2 with and without ATP: bound waters and natural ligand as guides for inhibitor design. J Med Chem 39 pp. 4540 (1996).

DETAILED DESCRIPTION OF THE INVENTION

Figure 1:
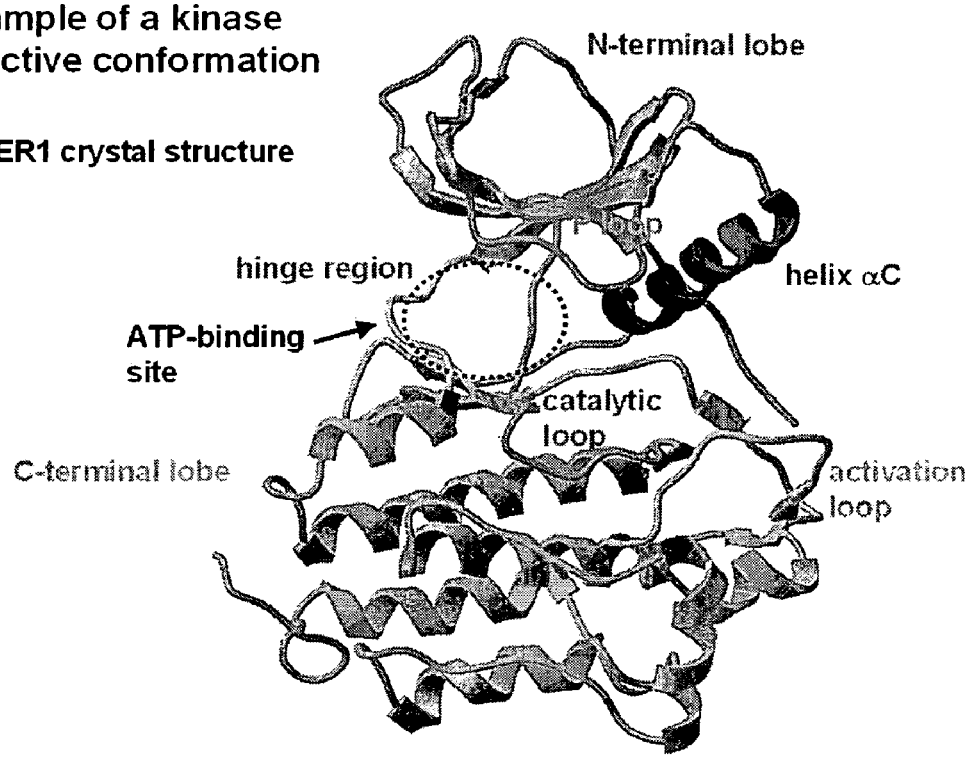
FIG. 1 depicts the X-ray structure of HER1, color-coded by key elements of a typical kinase.
Figure 2:
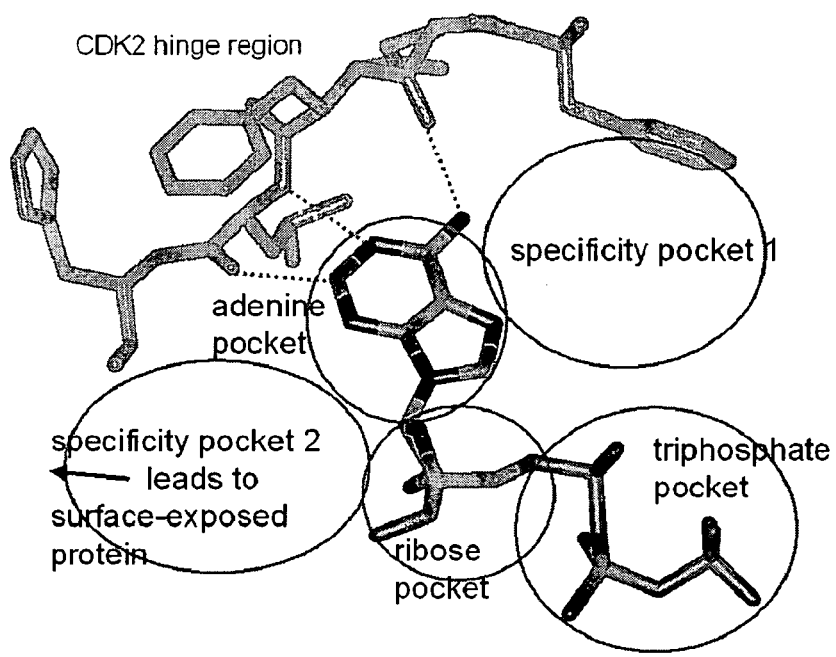
FIG. 2 depicts an X-ray structure of CDK2 complexed with ATP. Different regions of a typical ATP-binding site are delineated.

The present invention provides for compounds of formula I, pharmaceutical compositions employing such compounds and for methods of using such compounds.

In accordance with the present invention, there are disclosed compounds of formula I

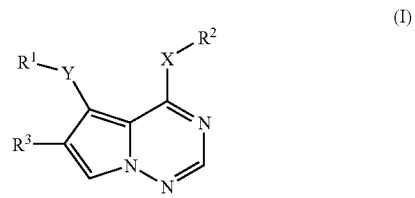

wherein the symbols have the following meanings and are, for each occurrence, independently selected:
$R^1$ is cycloalkyl or substituted cycloalkyl, aryl or substituted aryl, heterocyclyl or substituted heterocyclyl;
$R^2$ is aryl, substituted aryl, heteroaryl or substituted heteroaryl, heterocyclyl or substituted heterocyclyl;
$R^3$ is hydrogen, alkyl or substituted alkyl;
X is a direct bond, —$NR^3$— or —O—;
Y is a direct bond, alkyl or substituted alkyl, alkenyl or substituted alkenyl, alkynyl or substituted alkynyl;
or a pharmaceutically acceptable salt or stereoisomer thereof,
with the proviso that $R^2$ is not indazolyl or substituted indazolyl.

These compounds inhibit the tyrosine kinase activity of growth factor receptors such as HER2.

In another embodiment, the invention comprises a compound of formula I wherein
$R^1$ is heterocyclyl or substituted heterocyclyl;
$R^2$ is aryl, substituted aryl, heteroaryl or substituted heteroaryl;
$R^3$ is hydrogen;
X is —$NR^3$— or —O—;
Y is alkyl or substituted alkyl;

or a pharmaceutically acceptable salt or stereoisomer thereof.

Preferred $R^2$ substituents include
oxazolyl, thienyl, pyridinyl, thiazolyl, pyrazinyl, and phenyl, all of which may be suitably substituted with one or more substitutents.

Preferred $R^1$ substituents include
benzyl, imidazolyl-ethyl, (methyl-imidazolyl)-ethyl, piperidinyl-ethyl, pyridinyl-propyl, pyridinyl-methyl, morpholinyl-ethyl, (methyl-imidazolyl)-methyl, pyridinyl-ethyl, amino- piperidinyl-methyl, 4-amino-1-methyl-piperidin-3-ol, (methyl-piperazinyl)-ethyl, pyridinyl-ethyl, (methyl-piperidinyl)-ethyl, (methyl-imidazolyl)-propyl, (methyl-piperidinyl)-methyl, (methyl-piperazinyl)-propyl, diisopropylamino-ethyl, piperidinyl-propyl, dimethylamino-ethyl, dimethylamino-propyl, [(trifluoro-acetyl)-piperidinyl]-propyl, piperidinyl-ethyl, piperazinyl-ethyl, piperazinyl-propyl, pyrrolidinyl-ethyl, triazolyl-ethyl, triazolyl-propyl, (dimethylamino-ethoxy)-ethyl, imidazolyl-propyl, [(trifluoro-acetyl)-piperidinyl]-propyl, (piperazinyl-ethoxy)-ethyl, [(trifluoro-acetyl)-piperazinyl]-propyl, [(trifluoro-acetyl)-piperazinyl]-ethyl, piperidinyl-methyl, pyrazolyl-ethyl, (amino-ethoxy)-ethyl, (methoxy-ethoxy)-ethyl, pyrazolyl-propyl, [(methoxy-ethyl)-methyl-amino]-ethyl, morpholinyl-propyl, (cyanomethyl-piperazinyl)-ethyl, [(cyano-ethyl)-methyl-amino]-ethyl, [(methoxy-ethyl)-piperidinyl]-methyl, [(methoxy-ethyl)-piperidinyl]-ethyl, [(fluoro-ethyl)-methyl-amino]-ethyl, [(fluoro-ethyl)-methyl-amino]-propyl, (methyl-piperidinyl)-propyl, [(methanesulfonyl-ethyl)-piperazinyl]-ethyl, [(cyano-ethyl)-piperazinyl]-ethyl, [(methoxy-ethyl)-piperazinyl]-ethyl, [(methoxy-ethyl)-methyl-amino]-propyl, (cyanomethyl-methyl-amino)-propyl, (cyanomethyl-methyl-amino)-ethyl, [(methanesulfonyl-ethyl)-methyl-amino]-propyl, (difluoro-piperidinyl)-propyl, (difluoro-piperidinyl)-ethyl, [(cyano-ethyl)-methyl-amino]-propyl, [(methanesulfonyl-ethyl)-methyl-amino]-ethyl, [(trifluoro-ethyl)-piperazinyl]-ethyl, [cyanomethyl-(methanesulfonyl-ethyl)-amino]-propyl, [cyanomethyl-(methanesulfonyl-ethyl)-amino]-ethyl, (cyanomethyl-piperazinyl)-propyl, [(methanesulfonyl-ethyl)-piperazinyl]-propyl, [(cyano-ethyl)-piperazinyl]-propyl, [(trifluoro-ethyl)-piperazinyl]-propyl, (methanesulfonyl-ethyl-amino)-ethyl, [(cyano-ethyl)-piperidinyl]-methyl, (cyanomethyl-piperidinyl)-methyl, (hydroxy-piperidinyl)-propyl, [(methanesulfonyl-ethyl)-piperidinyl]-methyl, piperidinyl-methyl, piperidinyl, imidazolyl-propyl, 1-methyl-[1,4]-diazepan-6-ol, methanesulfonyl-propyl, (methanesulfonyl-ethyl-amino)-propyl, pyrrolidinyl-methyl, methanesulfonyl-ethyl, (cyanomethyl-amino)-ethyl, (cyanomethyl-amino)-propyl, (dioxo-thiomorpholinyl)-propyl, (oxo-piperidinyl)-propyl, [(difluoro-ethyl)-methyl-amino]-ethyl, morpholinyl-methyl, (hydroxy-pyrrolidinyl)-propyl, (hydroxy-piperidinyl)-propyl, pyrrolidinyl-methyl, (hydroxy-pyrrolidinyl)-propyl, methyl-piperidinyl, (methyl-pyrrolidinyl)-methyl, morpholinyl-methyl, pyrrolidinyl-methyl, (methyl-tetrahydro-pyridinyl)-methyl, (cyano-ethyl)-piperidinyl, azetidinyl, (methanesulfonyl-ethyl)-piperidinyl, (cyano-methyl)-piperidinyl, isopropyl-piperidinyl, propyl-piperidinyl, acetyl-piperidinyl, ethyl-piperidinyl, allyl-piperidinyl, tetrahydro-pyranyl, (hydroxy-ethyl)-piperidinyl, (methyl-pyrrolidinyl)-methyl, (methoxyethyl)-piperidinyl, piperidinyl, (methoxy-ethyl)-azetidinyl, (methoxy-methoxymethyl-ethyl)-piperidinyl, (methoxy-acetyl)-piperidinyl, methoxycarbonyl-piperidnyl, (hydroxy-acetyl)-piperidinyl, piperidine-carboxylic acid-acetoxy-ethyl, piperidine-carboxylic acid-acetoxy-methyl-ethyl, hydroxy-piperidinyl, amino-cyclohexyl, piperidinyl, piperidine-carboxylic acid-methyl-oxo-dioxolylmethyl, hydroxymethyl-piperidinyl, (aminomethyl)-cyclohexyl, amino-methyl-cyclohexyl, hydroxy-piperidinyl-methyl, morpholinyl, amino-cyclohexyl, hydroxymethyl-piperidinyl, tetrahydro-pyranyl, methanesulfonyl-propyl, amino-methyl-propyl, amino-cyclohexyl, amino-methyl-cyclohexyl, (hydroxy-piperidinyl)-propyl, piperidinyl, amino-propyl, morpholinyl-methyl, piperidinyl, (tert-butoxycarbonyl-morpholinyl)-methyl, benzyl, imidazolyl-ethyl, piperidinyl-ethyl, methoxyethyl, (diethylamino)-(methoxyethyl), pyrrolidinyl-ethyl, acetamide and methyl.

In another embodiment, the invention comprises a compound of formula II,

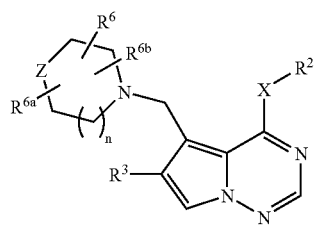

(II)

wherein

X is a direct bond, —NR$^3$— or —O—;

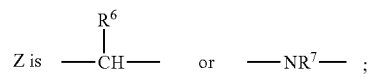

$R^2$ is aryl or substituted aryl, heteroaryl or substituted heteroaryl, $R^3$, $R^4$ and $R^5$ are independently selected from hydrogen, alkyl and substituted alkyl;

$R^6$, $R^{6a}$ and $R^{6b}$ are independently selected from the group consisting of one or more hydrogen, halogen, alkyl, alkoxy, aryloxy, —CN, —NH$_2$, —OH, —COOH, —CH$_2$OR$^5$, —CONHSO$_2$R$^5$, —CONR$^4$R$^5$, —NHalkyl, —NHCOalkyl, —NR$^4$SO$_2$alkyl, —NR$^4$SO$_2$NR$^4$R$^5$, —OCONR$^4$R$^5$, —CF$_3$ and —OCF$_3$, two of which may be attached to the same ring carbon atom provided that the resultant compound is chemically stable;

$R^7$ is hydrogen, alkyl or —NH$_2$, and n is 0, 1, 2 or 3;

or a pharmaceutically acceptable salt or stereoisomer thereof.

In another embodiment, the invention comprises a compound of formula III,

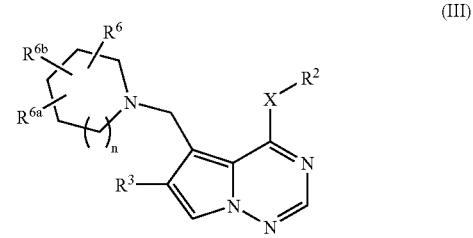

(III)

wherein

X is a direct bond, —NR$^3$— or —O—;

$R^2$ is aryl or substituted aryl, heteroaryl or substituted heteroaryl, $R^3$, $R^4$ and $R^5$ are independently selected from hydrogen, alkyl and substituted alkyl;

$R^6$, $R^{6a}$ and $R^{6b}$ are independently selected from the group consisting of one or more hydrogen, halogen, alkyl, alkoxy, aryloxy, —CN, —NH$_2$, —OH, —COOH, —CH$_2$OR$^5$, —CONHSO$_2$R$^5$, —CONR$^4$R$^5$, —NHalkyl, —NHCOalkyl, —NR$^4$SO$_2$alkyl, —NR$^4$SO$_2$NR$^4$R$^5$, —OCONR$^4$R$^5$, —CF$_3$ and —OCF$_3$, two of which may be attached to the same ring carbon atom provided that the resultant compound is chemically stable; and n is 0, 1, 2 or 3;

or a pharmaceutically acceptable salt or stereoisomer thereof.

In another embodiment, the invention comprises a compound of formula III, wherein $R^2$ is phenyl, substituted phenyl, pyridinyl, substituted pyridinyl, pyrimidinyl, substituted pyrimidinyl, oxazole, substituted oxazole, thiazole, substituted thiazole, pyrazinyl or substituted pyrazinyl;

$R^6$, $R^{6a}$ and $R^{6b}$ are independently selected from the group consisting of one or more hydrogen, —NH$_2$, OH, alkoxy, —CONR$^4$R$^5$, —NR$^4$SO$_2$alkyl, —NR$^4$SO$_2$NR$^4$R$^5$, —OCONR$^4$R$^5$, —NHalkyl and —NHCOalkyl;

X is —NH—; and n is 1 or 2.

Preferred compounds of the invention include the following

5-[(4-Amino-1-piperidinyl)methyl]-N-(3-chloro-4-fluorophenyl)pyrrolo[2,1-f][1,2,4]triazine-4-amine, 5-[(4-Amino-1-piperidinyl)methyl]-N-2-naphthalenylpyrrolo[2,1-f][1,2,4]triazin-4-amine, 5-[(4-Amino-1-piperidinyl)methyl]-N-phenylpyrrolo[2,1-f][1,2,4]triazin-4-amine, 5-[(4-Amino-1-piperidinyl)methyl]-N-(3-methoxyphenyl)pyrrolo[2,1-f][1,2,4]triazin-4-amine, 5-[(4-Amino-1-piperidinyl)methyl]-N-(3-ethynylphenyl)pyrrolo[2,1-f][1,2,4]triazin-4-amine, 5-[(4-aminopiperidin-1-yl)methyl]-N-(4-fluoro-3-methoxyphenyl)pyrro-lo[2,1-f][1,2,4]triazin-4-amine, (3R,4R)-4-amino-1-[[4-[(3-chloro-4-fluorophenyl)amino]pyrrolo[2,1-f][1,2,4]triazin-5-yl]methyl]piperidin-3-ol, (3S,4S)-4-amino-1-[[4-[(3-chloro-4-fluorophenyl)amino]pyrrolo[2,1-f][1,2,4]triazin-5-yl]methyl]piperidin-3-ol, (3R,4R)-4-amino-1-[[4-[(3-methoxyphenyl)amino]pyrrolo[2,1-f][1,2,4]triazin-5-yl]methyl]piperidin-3-ol, (3S,4S)-4-amino-1-[[4-[(3-methoxyphenyl)amino]pyrrolo[2,1-f][1,2,4]triazin-5-yl]methyl]piperidin-3-ol, (3R,4R)-4-amino-1-[[4-[(3-methoxy-4-fluorophenyl)amino]pyrrolo[2,1-f][1,2,4]triazin-5-yl]methyl]piperidin-3-ol, (3R,4R)-4-amino-1-({4-[(3-ethynylphenyl)-amino]pyrrolo[2,1-f]-[1,2,4]-triazin-5-yl}-methyl)piperidin-3-ol, (3R,4R)-4-amino-1-({4-[(3-ethoxyphenyl)-amino]-pyrrolo[2,1-f]-[1,2,4]triazin-5-yl }-methyl)piperidin-3-ol (3R,4R)-4-amino-1-{[4-(2-naphthylamino)-pyrrolo[2,1-f][1,2,4]-triazin-5-yl]methyl}piperidin-3-ol, (3R,4R)-4-amino-1-({4-[(3-methoxy-4-methyl-phenyl)amino]pyrrolo[2,1-f][1,2,4]triazin-5-yl)-methyl)piperidin-3-ol, (3R,4R)-4-amino-1-({4-[(3-bromophenyl)amino]pyrrolo[2,1-f][1,2,4]-triazin-5-yl}methyl)-piperidin-3-ol, (3R,4R)-4-amino-1-({4-[(3-fluoro-5-methoxy-phenyl)amino]pyrrolo[2,1-f][1,2,4]triazin-5-yl}-methyl)piperidin-3-ol, (3S,4R)-4-amino-1-({4-[(3-methoxyphenyl)amino]pyrrolo[2,1-f][1,2,4]triazin-5-yl}methyl)piperidin-3-ol, (3S,4S)-4-amino-1-({4-[(3-methoxyphenyl)amino]pyrrolo[2,1-f][1,2,4]triazin-5-yl}methyl)piperidin-3-ol (3S,4R)-4-amino-1-({4-[(3-chlorophenyl)amino]-pyrrolo[2,1-f][1,2,4]-triazin-5-yl}methyl)-piperidin-3-ol, (3S,4R)-4-amino-1-({4-[(3-chloro-4-fluoro-phenyl)amino]pyrrolo[2,1-f][1,2,4]triazin-5-yl}-methyl)piperidin-3-ol, (3S,4R)-4-amino-1-({4-[(3-ethynylphenyl)amino]pyrrolo[2,1-f][1,2,4]triazin-5-yl}methyl)piperidin-3-ol, (3R,4S)-4-amino-1-({4-[(3-ethynylphenyl)-amino]pyrrolo[2,1-f][1,2,4]triazin-5-yl}methyl)piperidin-3-ol, (3R,4S)-4-amino-1-({4-[(3-chlorophenyl)amino]pyrrolo[2,1-f][1,2,4]-triazin-5-yl}methyl)-piperidin-3-ol, (3R,4R)-4-amino-1-({4-[(3-methoxyphenyl)amino]pyrrolo[2,1-f][1,2,4]triazin-5-yl}methyl)piperidin-3-yl carbamate, (3R,4R)-4-amino-1-({4-[(3-ethynylphenyl)-amino]pyrrolo[2,1-f][1,2,4]triazin-5-yl}-methyl)piperidin-3-yl carbamate, (3R,4R)-4-amino-1-({4-[(3-chloro-4-fluoro-phenyl)amino]pyrrolo[2,1-[1,2,4]triazin-5-yl}-methyl)piperidin-3-yl carbamate, (3S,4R)-4-amino-1-({4-[(3-chloro-4-fluoro-phenyl)amino]pyrrolo[2,1-f][1,2,4]triazin-5-yl}methyl)piperidin-3-yl carbamate, (3S,4R)-4-amino-1-({4-[(3-ethynylphenyl)-amino]pyrrolo[2,1-f][1,2,4]triazin-5-yl}-methyl)piperidin-3-yl carbamate, (3S,4R)-4-amino-1-({4-[(3-methoxyphenyl)amino]pyrrolo[2,1-f][1,2,4]triazin-5-yl}methyl)-3-methylpiperidin-3-ol, (3R/S,5R/S)-4-amino-1-({4-[(3-methoxyphenyl)amino]pyrrolo[2,1-f][1,2,4]triazin-5-yl}methyl)piperidine-3,5-diol, (3S,5S)-4-amino-1-({4-[(4-fluoro-3-methoxy-phenyl)amino]pyrrolo[2,1-f][1,2,4]triazin-5-yl}-methyl)piperidine-3,5-diol, (3R,5R)-4-amino-1-({4-[(3-ethynylphenyl)-amino]pyrrolo[2,1-f][1,2,4]triazin-5-yl}methyl)piperidine-3,5-diol, 5-{[(3R,4R)-4-amino-3-methoxypiperidin-1-yl]methyl}-N-(3-methoxyphenyl)pyrrolo[2,1-f][1,2,4]triazin-4-amine, 5-(((4aR,8aR)-rel-hexahydro-1H-pyrido[3,4-b][1,4]oxazin-6(7H)-yl)methyl)-N-(3-methoxyphenyl)pyrrolo[1,2-f][1,2,4]triazin-4-amine, (3R,4R)-4-amino-1-({4-[(3-methoxyphenyl)amino]pyrrolo[2,1-f][1,2,4]triazin-5-yl}methyl)-N-(methylsulfonyl)piperidine-3-carboxamide, (3R,4R)-4-amino-1-({4-[(3-ethynylphenyl)amino]pyrrolo[2,1-f][1,2,4]triazin-5-yl}methyl)-N-methylpiperidine-3-carboxamide, (3R,4R)-4-amino-1-({4-[(3-methoxyphenyl)amino]pyrrolo[2,1-f][1,2,4]triazin-5-yl}methyl)-N-methylpiperidine-3-carboxamide, (3R,4R)-4-amino-1-({4-[(3-methoxyphenyl)amino]pyrrolo[2,1-f][1,2,4]triazin-5-yl}methyl)piperidine-3-carboxamide, ((3R,4R)-1-((4-(3-methoxyphenylamino)pyrrolo[1,2-f][1,2,4]-triazin-5-yl)methyl)-4-((R)-1-phenylethylamino)piperidin-3-yl)methanol, N-[(3R,4R)-4-amino-1-({4-[(3-methoxyphenyl)amino]pyrrolo[2,1-f][1,2,4]triazin-5-yl}methyl)piperidin-3-yl]urea, N-[(3R,4R)-4-amino-1-({4-[(3-methoxyphenyl)amino]pyrrolo[2,1-f][1,2,4]triazin-5-yl}methyl)piperidin-3-yl]methanesulfonamide, and N-[(3S,4R)-4-amino-1-({4-[(3-methoxyphenyl)amino]pyrrolo[2,1-f][1,2,4]triazin-5-yl}methyl)piperidin-3-yl]methanesulfonamide, or a pharmaceutically acceptable salt thereof.

The following are definitions of terms that may be used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl or a substituted aryl group bonded directly through an alkyl group, such as benzyl.

The term "aryloxy" refers to an aryl or a substituted aryl group bonded directly through an alkoxy group, such as methoxy or ethoxy.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl]or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents. Also included are smaller heterocyclyls, such as, epoxides and aziridines.

The term "carbocyclic ring" refers to stable, saturated or partially unsaturated monocyclic hydrocarbon rings of 3 to 7 carbon atoms such as cyclopropyl, cyclobutyl, cyclopentyl, cyclohexyl and cycloheptyl. The term "optionally substituted" as it refers to "carbocyclic ring" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Any compound that will be converted in vivo to provide the bioactive agent (i.e., the compound for formulas I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991); and c) H. Bundgaard, *Advanced Drug Delivery Reviews*, 8, 1–38 (1992).

It should further be understood that solvates (e.g., hydrates) of the compounds of formula I are also with the scope of the present invention. Methods of solvation are generally known in the art.

Utility

The present invention is based on the discovery that certain pyrrolotriazines are inhibitors of protein kinases. More specifically, pyrrolotriazines such as those described in this invention inhibit the protein tyrosine kinase activity of members of the HER family of receptors. These inhibitors will be useful in the treatment of proliferative diseases that are dependent on signaling by one or more of these receptors. Such diseases include psoriasis, rheumatoid arthritis, and solid tumors of the lung, head and neck, breast, colon, ovary, and prostate. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with HER1 (EGF receptor) and HER2, especially those tumors which are significantly dependent on HER1 or HER2 for their growth and spread, including for example, cancers of the bladder, squamous cell, head, colorectal, oesophageal, gynecological (such as ovarian), pancreas, breast, prostate, vulva, skin, brain, genitourinary tract, lymphatic system (such as thyroid), stomach, larynx and lung. In another embodiment, the compounds of the present invention are also useful in the treatment of noncancerous disorders such as psoriasis and rheumatoid arthritis.

Thus according to a further aspect of the invention there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

By virtue of their ability to inhibit HER1, HER2, and HER4 kinases, compounds of the present invention can be used for the treatment of proliferative diseases, including psoriasis and cancer. The HER1 receptor kinase has been shown to be expressed and activated in many solid tumors including head and neck, prostate, non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor efficacy in preclincal and clinical studies. It is therefore expected that inhibitors of the HER1 and HER2 kinases will have efficacy in the treatment of tumors that depend on signaling from either of the two receptors. In addition, these compounds will have efficacy in inhibiting tumors that rely on HER receptor heterodimer signaling. These compounds are expected to have efficacy either as single agent or in combination (simultaneous or sequentially) with other chemotherapeutic agents such as Taxol®, adriamycin, and cisplatin. Since HER1 and HER2 signaling has been shown to regulate expression of angiogenic factors such as vascular endothelial growth factor (VEGF) and interleukin 8 (IL8), these compounds are expected to have anti-tumor efficacy resulting from the inhibition of angiogenesis in addition to the inhibition of tumor cell proliferation and survival. The HER2 receptor has been shown to be involved in the hyperproliferation of synovial cells in rheumatoid arthritis, and may contribute to the angiogenic component of that inflammatory disease state. The inhibitors described in this invention are therefore expected to have efficacy in the treatment of rheumatoid arthritis. The ability of these compounds to inhibit HER1 further adds to their use as antiangiogenic agents. See the following documents and references cited therein: Schlessinger J., "Cell signaling by receptor tyrosine kinases", *Cell* 103(2), p. 211–225 (2000); Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639–2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904–914 (2000); Satoh, K., Kikuchi, S., Sekimata, M., Kabuyama, Y., Homma, M. K., and Homma Y., "Involvement of ErbB-2 in rheumatoid synovial cell growth", *Arthritis Rheum.* 44(2), p. 260–265 (2001).

The antiproliferative treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine, and taxoids such as Taxol® (paclitaxel), Taxotere® (docetaxel) and newer microbtubule agents such as epothilone analogs, discodermolide analogs, and eleutherobin analogs); topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the present invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, and osteosarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as HER1 (EGF receptor), HER2, or HER4.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.™. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

HER1, HER2 or HER4 Kinase Assays

Compounds of interest were assayed in a kinase buffer that contained 20 mM Tris.HCl, pH 7.5, 10 mM $MnCl_2$, 0.5 mM dithiothreitol, bovine serum albumin at 0.1 mg/ml, poly(glu/tyr, 4:1) at 0.1 mg/ml, 1 µM ATP, and 4 µCi/ml [γ-$^{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1 and HER4, the cytoplasmic sequences of the receptors were expressed in insect cells as GST fusion proteins, which were purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

The instant compounds inhibit HER1, HER2, and HER4 kinases with IC50 values between 0.001 to 25 µM. Preferred compounds have $IC_{50}$ values between 0.001–5.0 µM. More preferred compounds have $IC_{50}$ values between 0.001–1.0 µM. Most preferred compounds have $IC_{50}$ values between 0.001–0.1 µM.

Methods of Preparation

Certain compounds of formula I may generally be prepared according to the following schemes and the knowledge of one skilled in the art. Supplemental preparation information may also be found in co-pending U.S. patent application Ser. No. 09/573,829 filed May 18, 2000 and International Publication Number WO 00/71129, both herein incorporated by reference.

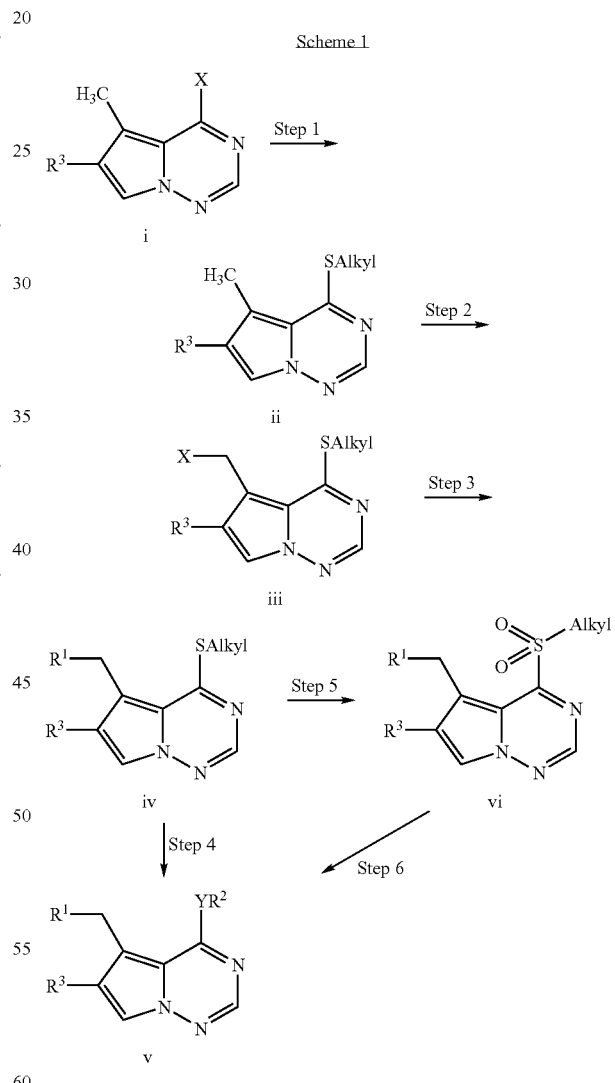

Where X = Halogen, Y = N or O, Alk = $CH_3$ or nBu

Step 1

The first step of Scheme 1 is accomplished by treating Compound i (Ref. WO 03/042172 A2) with a thiol such as methanethiol or butanethiol or their sodium salts in an anhydrous solvent such as THF under an inert atmosphere such as $N_2$ to give Compound ii.

Step 2

Halogenation of the 5-methyl group of Compound ii is affected by treatment with a halogenating reagent such as N-bromosuccinimide. The reaction is preformed under an inert atmosphere such Ar in the presence of a catalyst such as dibenzoyl peroxide or 2,2'-azobisisobutyronitrile and gives the 5-halomethyl-pyrrolotrazine Compound iii.

Step 3

Treatment of Compound iii with a primary or secondary amine or alcohol in the presence of a base such as $NaHCO_3$ or triethylaamine or diisopropylethylamine in a solvent such as acetonitrile or N,N-dimehylformamide affords intermediate Compound iv.

Step 4

Treatment of intermediate Compound iv with an aniline in the presence of $HgCl_2$ in a solvent such as toluene affords the 4-substituted pyrrolotriazines Compound v.

Step 5

Alternatively compounds of formula iv may be treated with an appropriate oxidizing agent such as m-chloroperbenzoic acid in a solvent such as $CH_2Cl_2$ to afford sulfones vi.

Step 6

Sulfones vi may be converted to compound v by treatment with a primary or secondary amine or alcohol in an inert solvent such as $CH_2Cl_2$ Alternatively, compounds of general formula I may be prepared as shown in Scheme 2.

Step 1

The first step of Scheme 2 is accomplished by treating Compound i (Ref. WO 03/042172 A2) with a halogenating reagent such as N-bromosuccinimide under an inert atmosphere such as Ar. The reaction is performed in an appropriate solvent such as $CCl_4$ in the presence of a catalyst such as dibenzoyl peroxide or 2,2'-azobisisobutyronitrile to afford the dihalopyrrolotrazine Compound vii.

Step 2

Compound vii may be converted to ammonium salt Compound viii by treatment with a tertiary base such as triethylamine in an anhydrous solvent such as THF.

Step 3

Treatment of Compound viii with an amine or its anion in an anhydrous solvent such as acetonitrile, chloroform or THF affords ammonium salt Compound ix.

Step 4

Conversion of Compound ix to pyrrolotriazine Compound v may be accomplished by treatment of Compound ix with a primary or secondary amine or alcohol in the presence of a base such as diisopropylethylamine in a solvent such as acetonitrile.

Compounds prepared by the above methods having general formula x in Scheme 3 in which the 5-methylsubstituent contains a protecting group such as t-butoxycarbonyl may further be modified by removal of the protecting group in Step 1 by treatment with anhydrous HCl in diethyl ether or 1,4-dioxane or by treatment of a solution of the compound in $CH_2Cl_2$ with trifluoroacetic acid to prepare the free amines xi. Further modification may be accomplished in Step 2 by treating Compound xi with a carbonyl compound such as propanal in the presence of a reducing agent such as sodium triacetoxyborohydride in a solvent such as $CH_2Cl_2$ to afford substituted amines xii.

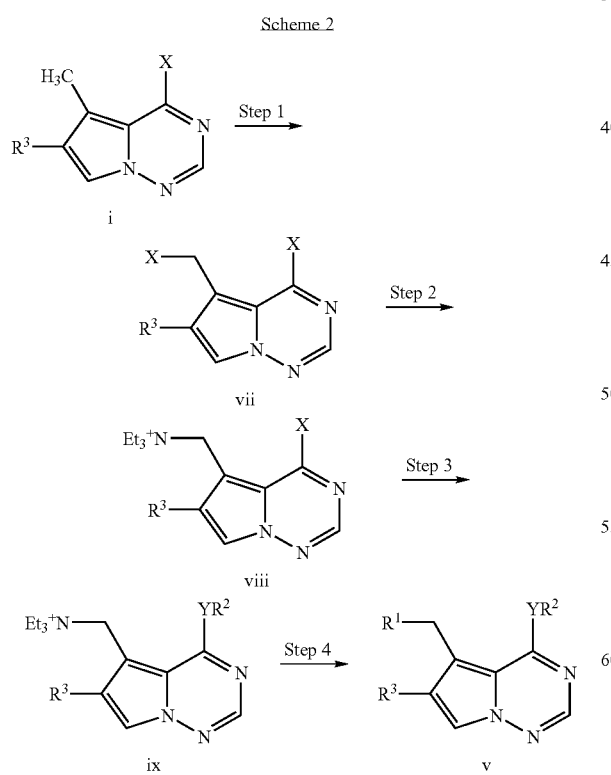

Scheme 2

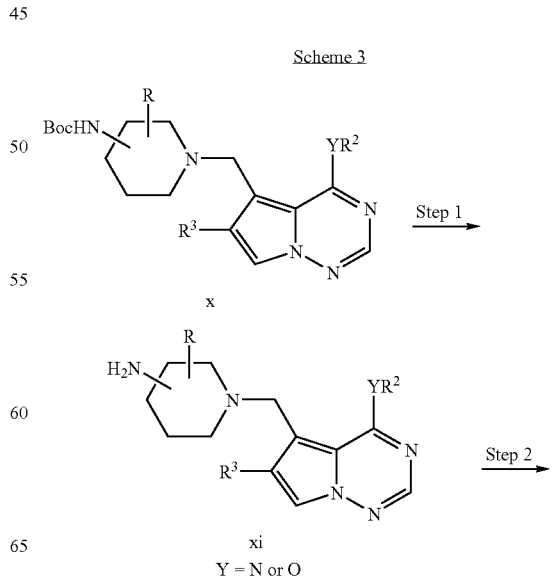

Scheme 3

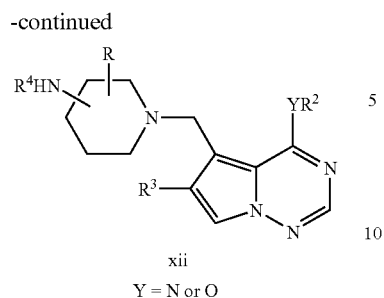

xii

Y = N or O

Further compounds may be prepared as shown in Scheme 4. In Step 1, compound ix may be treated with a secondary amine such as bis-(2-chloroethyl)amine in an appropriate solvent such as acetonitrile in the presence of a base such as diisopropylethylamine to afford Compound xii. Compound xii may further be treated with a nucleophile such as hydrazine in Step 2 to afford Compund xiii.

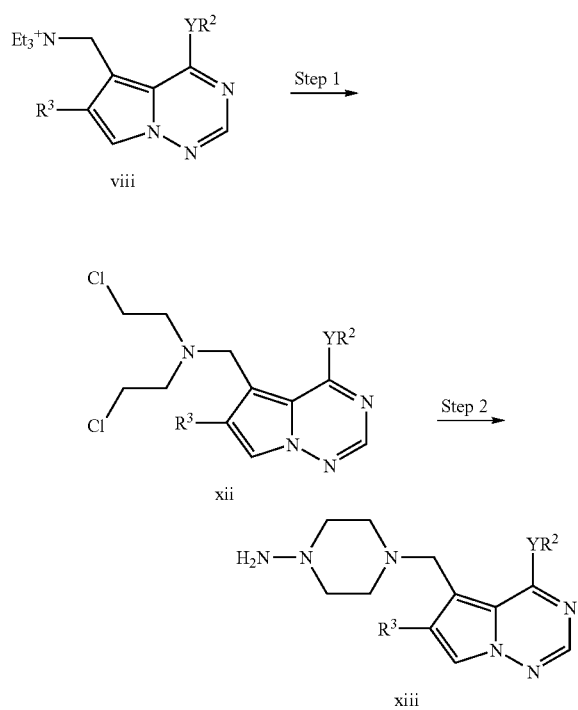

Further 5-substituted pyrrolotriazines may be prepared according to Scheme 5.

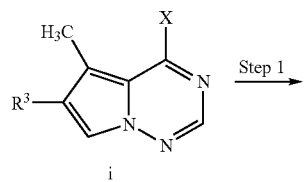

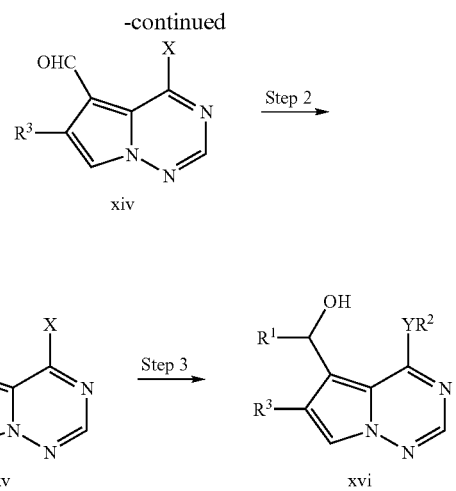

Step 1

Compound i may be treated with two equivalents of a brominating reagent such as N-bromosuccinimide in a solvent such as $CCl_4$ at elevated temperature. The resulting 5-dibromopyrrolotriazine may be converted to the corresponding dimethylacetal using methanol in the presence of a base such as $NaHCO_3$ and then to the aldehyde Compound xiv by treating the intermediate acetal with an acid such as trifluoroacetic acid in the presence of water.

Step 2

Treatment of aldehyde Compound xiv with an organometallic reagent such as a Grignard reagent in an anhydrous solvent such as THF affords alcohol xv.

Step 3

Alcohol xv may be treated with a primary or secondary amine or alcohol in the presence of a base such as $NaHCO_3$ in an appropriate solvent such as acetonitrile to afford compounds of formula xvi.

In addition, other compounds of formula I may be prepared using procedures generally known to those skilled in the art. In particular, the following examples provide additional methods for the preparation of the compounds of this invention.

The invention will now be further described by the following working examples(s), which are preferred embodiments of the invention. All temperatures are in degrees Celsius (°C.) unless otherwise indicated. "HPLC Ret Time" is the HPLC retention time that was obtained under the following conditions: column type and length, gradient time [unless otherwise indicated, all gradients started with 100% solvent A (10% MeOH, 90% $H_2O$, 0.1% TFA) and ended with 100% solvent B (90% MeOH, 10% $H_2O$, 0.1% TFA)], flow rate (mL/min). UV detection was always conducted at 220 nM. These examples are illustrative rather than limiting and it is to be understood that there may be other embodiments that fall within the spirit and scope of the invention as defined by the claims appended hereto.

EXAMPLE 1

5-[(4-Amino-1-piperidinyl)methyl]-N-(3-chloro-4-fluorophenyl)pyrrolo[2,1-f][1,2,4]triazin-4-amine

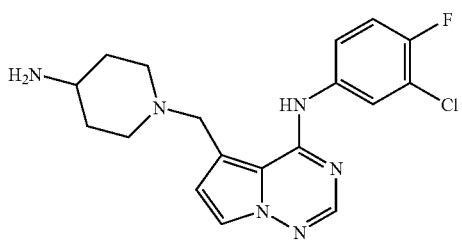

1A. Preparation of 5-methyl-4-methylsulfanyl-pyrrolo[2,1f][1,2,4]triazine

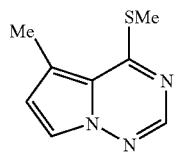

To a solution of 4-chloro-5-methyl-pyrrolo[2,1f][1,2,4]triazine (4.02 g, 24.0 mmol)(Ref. WO 03/042172 A2) in dry THF (200 ml) sparged with $N_2$ at 0° C. was added NaSMe (1.85 g, 26.3 mmol). The sparging was continued for 5 min. The reaction mixture was then stirred at rt overnight, concentrated in vacuo to about 50 ml volumn left. Diluted with $H_2O$ (280 ml) and stirred at 0° C. The solid was filtered, washed with cold water, dried to give 1A (3.91 g, 91%). It had an analytical HPLC retention time=3.38 min. (YMC S5 ODS column 4.6×50 mm, 10–90% aqueous methanol over 4 minutes containing 0.2% phosphoric acid, 4 ml/min, monitoring at 220 nm) and a LC/MS $M^++1=180$.

1B. Preparation of [1-(4-methylsulfanyl-pyrrolo[2,1-f][1,2,4]triazin-5-ylmethyl)-piperidin-4-yl]-carbamic acid tert-butyl ester

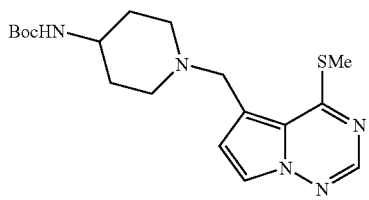

A mixture of 1A (1.94 g, 10.8 mmol), benzoyl peroxide (0.262 g, 1.08 mmol), NBS (2.12 g, 11.90 mmol) in $CCl_4$ (100 ml) was sparged with $N_2$, then immediately heated to 85° C. for 1.5 h. The mixture was cooled to rt and the precipitate was filtered off. The filtrate was concentrated in vacuo, diluted with dichloroethane (35 ml), and DIEA (2.24 ml, 12.96 mmol) and piperidin-4-yl-carbamic acid tert-butyl ester (2.38 g, 11.90 mmol) were added. The reaction mixture was stirred at rt for 1 h. The mixture was diluted with saturated $NaHCO_3$ (70 ml) and extracted with EtOAc (3×100 ml). The combined EtOAc extracts were washed with brine (1×100 ml), dried ($MgSO_4$), filtered and concentrated in vacuo. The residue was purified by silica gel flash column to give 1B (2.87 g, 70%) (0.1%–2% MeOH—$CH_2Cl_2$). It had an analytical HPLC retention time=2.12 min. (YMC S5 ODS column 4.6×50 mm, 10–90% aqueous methanol over 4 minutes containing 0.2% phosphoric acid, 4 Ml/min, monitoring at 220 nm) and a LC/MS $M^++1=378$.

1C. Preparation of 5-bromomethyl-4-chloro-pyrrolo[2,1-f][1,2,4]triazine

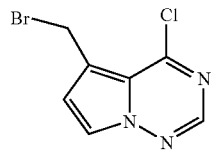

A mixture of 4-chloro-5-methyl-pyrrolo[2,1f][1,2,4]triazine (2.0 g, 11.93 mmol) (Ref. WO 03/042172 A2) and AIBN (195 mg, 1.19 mmol) in $CCl_4$ (80 ml) under $N_2$ was heated to 100° C. for 5 min, NBS (2.55 g, 14.3 mmol) was added. The reaction mixture was stirred for 10 min, then cooled to rt, filtered. The $CCl_4$ layer was washed with dilute $NaHCO_3$ aqueous solution, dried ($MgSO_4$), filtered and concentrated to give 1C (2.70 g, 92%).

1D. Preparation of (4-chloro-pyrrolo[2,1-f][1,2,4]triazin-5-ylmethyl)-triethyl-ammonium bromide

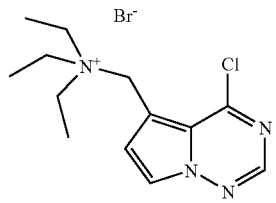

A mixture of 1C (2.7 g, 11 mmol), $Et_3N$ (5 ml, 36 mmol) in THF (20 ml) was stirred at rt for 12 h. The solid was filtered and rinsed with THF and $Et_2O$, dried to give 1D (3.38 g, 89%). It had an analytical HPLC retention time=0.776 min. (Chromolith SpeedROD 4.6×50 mm, 10–90% aqueous methanol over 4 minutes containing 0.1% TFA, 4 ml/min, monitoring at 220 nm) and a LC/MS $M^+=267$.

1E. Preparation of [4-(3-chloro-4-fluoro-phenylamino)-pyrrolo[2,1-f][1,2,4]triazin-5-ylmethyl]-triethyl-ammonium bromide hydrochloride

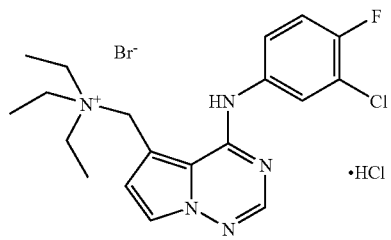

A mixture of 1C (1.0 g, 2.2 mmol) and 3-chloro-4-fluoro-phenylamine (418 mg, 2.87 mmol) in $CHCl_3$ (10 ml) was heated at 50° C. for 2 h. The solid was filtered and rinsed with $CHCl_3$, dried to give 1E (1.24 g, 87.4%). It had an analytical HPLC retention time=2.19 min. (Chromolith SpeedROD 4.6×50 mm, 10–90% aqueous methanol over 4 minutes containing 0.1% TFA, 4 ml/min, monitoring at 220 nm) and a LC/MS M+=376.

1F. Preparation of {1-[4-(3-chloro-4-fluoro-phenylamino)-pyrrolo[2,1-f][1,2,4]triazin-5-ylmethyl]-piperidin-4-yl}-carbamic acid tert-butyl ester

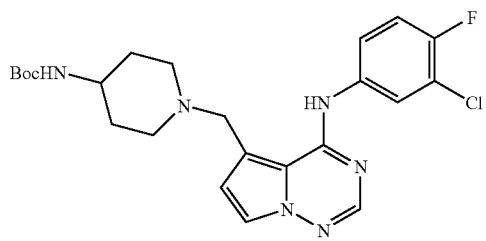

Method One:

A mixture of 1B (30 mg, 0.08 mmol), 3-chloro-4-fluoro-phenylamine (11 mg, 0.08 mmol) and HgCl$_2$ (24 mg, 0.088 mmol) in toluene (2 ml) was heated to reflux for 8 h. Cooled to rt, diluted with EtOAc (5 ml) and filtered. The filtrate was concentrated, and the residue was purified by prep HPLC to give 1F as an oil.

Method Two:

To a suspension of piperidin-4-yl-carbamic acid tert-butyl ester (4.1 g, 20.3 mmol) in CH$_3$CN (55 ml) at 70° C. was added a mixture of 1E (9.1 g, 18.4 mmol) and DIPEA (3.2 ml, 18.4 mmol) in CH$_3$CN (40 ml) dropwise in a period of 40 min. The reaction mixture was stirred at 70° C. for 1 h, then cooled to rt, after which H$_2$O (155 ml) was added slowly. The solid was filtered and rinsed with 15% CH$_3$CN/H$_2$O, then H$_2$O, and ried under vacuum to give 1F (7.84 g, 90%). It had an analytical HPLC retention time=2.73 min. (Chromolith SpeedROD 4.6×50 mm, 10–90% aqueous methanol over 4 minutes containing 0.1% TFA, 4 ml/min, monitoring at 220 nm) and a LC/MS M+ +1=475.

1G. Preparation of 5-[(4-amino-1-piperidinyl)methyl]-N-(3-chloro-4-fluorophenyl)pyrrolo[2,1-f][1,2,4]triazin-4-amine Compound 1F (from Method one) was treated 20% TFA/CH$_2$Cl$_2$ (3 ml) at 0° C., then stirred at rt for 2 h. The reaction mixture was concentrated and purified by prep HPLC to give the product as the TFA salt, which was treated with saturated NaHCO$_3$ to give the ree base 1G (4 mg, 13% for two steps). It had an analytical HPLC retention time=1.49 min. (Chromolith SpeedROD 4.6×50 mm, 10–90% aqueous methanol over 4 minutes containing 0.1% TFA, 4 ml/min, monitoring at 220 nm) and a LC/MS M+ +1=375.

EXAMPLE 2

5-[(4-Amino-1-piperidinyl)methyl]-N-4-pyridi-nylpyrrolo[2,1-f][1,2,4]triazin-4-amine

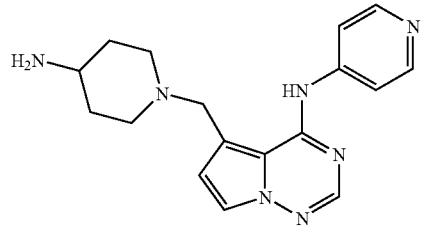

To a mixture of pyridin-4-ylamine (34 mg, 0.361 mmol) in THF (500 μl) was added 1N NaHMDS in THF (722 μl, 0.722 mmol). The mixture was cooled to 0° C. and a suspension of 1D (125 mg, 0.27 mmol) in DMF (800 μl) was added. The mixture was stirred at this temperature for 0.5 h. and piperidin-4-yl-carbamic acid tert-butyl ester (144 mg, 0.72 mmol)-was added to the cold mixture. The reaction mixture was heated to 50° C. for 10 min and concentrated to remove THF. TFA (1 ml) was added, the mixture was stirred until the protecting group was removed (2 h) (progress was monitored by HPLC). TFA was removed in vacuo and saturated NaHCO$_3$ was added. The mixture was extracted with EtOAc and the combined extracts were dried, concentrated and triturated first with Et2O to give the title compound (46 mg, 53%). Analytical HPLC retention time=0.51 min (Chromolith SpeedROD 4.6×50 mm, 10–90% aqueous methanol over 4 minutes containing 0.1% TFA, 4 ml/min, monitoring at 220 nm) and a LC/MS M+ +1=324.

EXAMPLES 3–37

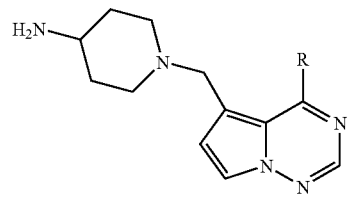

Compounds 3–37 were prepared using a similar process as the compound in Example 2 utilizing the corresponding amines.

| Ex. # | R | Compound Name | [M + H] | HPLC Ret Time (min) |
|---|---|---|---|---|
| 3 | ![pyrimidine] | 5-[(4-Amino-1-piperidinyl)methyl]-N-4-pyrimidinylpyrrolo[2,1-f][1,2,4]triazin-4-amine | 325 | 0.65(b) |

-continued

| Ex. # | R | Compound Name | [M + H] | HPLC Ret Time (min) |
|---|---|---|---|---|
| 4 | 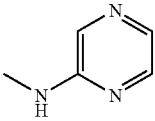 | 5-[(4-Amino-1-piperidinyl)methyl]-N-pyrazinylpyrrolo[2,1-f][1,2,4]triazin-4-amine | 325 | 1.02(b) |
| 5 | 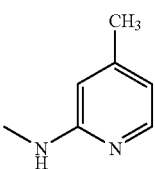 | 5-[(4-Amino-1-piperidinyl)methyl]-N-(4-methyl-2-pyridinyl)pyrrolo [2,1-f][1,2,4]triazin-4-amine | 338 | 0.71(b) |
| 6 | 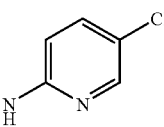 | 5-[(4-Amino-1-piperidinyl)methyl]-N-(5-methyl-2-pyridinyl)pyrrolo[2,1-f][1,2,4]triazin-4-amine | 338 | 0.80(b) |
| 7 | 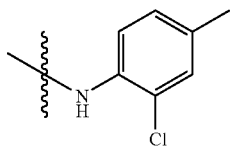 | 5-[(4-Amino-1-piperidinyl)methyl]-N-(2-chloro-4-methylphenyl)pyrrolo[2,1-f][1,2,4]triazin-4-amine | 371 | 1.61(b) |
| 8 | 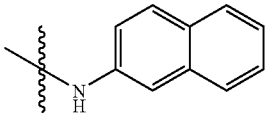 | 5-[(4-Amino-1-piperidinyl)methyl]-N-2-naphthalenylpyrrolo [2,1-f][1,2,4]triazin-4-amine | 373 | 1.81(b) |
| 9 | 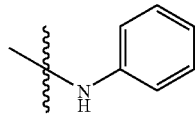 | 5-[(4-Amino-1-piperidinyl)methyl]-N-phenylpyrrolo[2,1-f][1,2,4]triazin-4-amine | 323 | 1.06(b) |
| 10 | 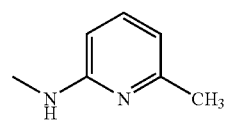 | 5-[(4-Amino-1-piperidinyl)methyl]-N-(6-methyl-2-pyridinyl)pyrrolo[2,1-f][1,2,4]triazin-4-amine | 338 | 0.60(b) |
| 11 | 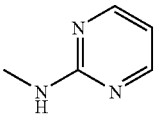 | 5-[(4-Amino-1-piperidinyl)methyl]-N-2-pyrimidinylpyrrolo[2,1-f][1,2,4]triazin-4-amine, trifluoroacetic acid salt (1:1) | 325 | 1.00(b) |
| 12 | 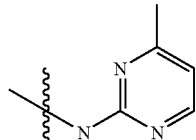 | 5-[(4-Amino-1-piperidinyl)methyl]-N-(4-methyl-2-pyrimidinyl)pyrrolo[2,1-f][1,2,4]triazin-4-amine, trifluoroacetic acid salt (1:1) | 339 | 1.03(b) |
| 13 | 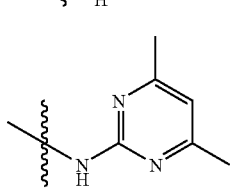 | 5-[(4-Amino-1-piperidinyl)methyl]-N-(4,6-dimethyl-2-pyrimidinyl)pyrrolo[2,1-f][1,2,4]triazin-4-amine, trifluoroacetic acid salt (1:1). | 353 | 1.08(b) |

-continued

| Ex. # | R | Compound Name | [M + H] | HPLC Ret Time (min) |
|---|---|---|---|---|
| 14 | 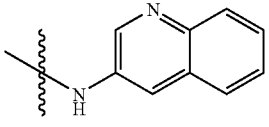 | N-[5-[(4-Amino-1-piperidinyl)methyl]pyrrolo[2,1-f][1,2,4]triazin-4-yl]-3-quinolinamine, trifluoroacetic acid salt (1:1). | 374 | 1.03(b) |
| 15 | 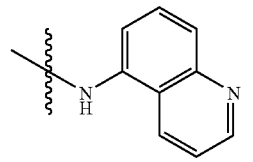 | N-[5-[(4-Amino-1-piperidinyl)methyl]pyrrolo[2,1-f][1,2,4]triazin-4-yl]-5-quinolinamine, trifluoroacetic acid salt (1:1). | 374 | 0.64(b) |
| 16 | 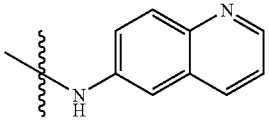 | N-[5-[(4-Amino-1-piperidinyl)methyl]pyrrolo[2,1-f][1,2,4]triazin-4-yl]-6-quinolinamine, trifluoroacetic acid salt (1:1). | 374 | 0.80(b) |
| 17 | 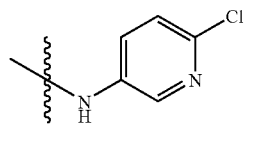 | 5-[(4-Amino-1-piperidinyl)methyl-N-(6-chloro-3-pyridinyl)pyrrolo[2,1-f][1,2,4]triazin-4-amine, trifluoroacetic acid salt (1:1). | 358 | 1.03(b) |
| 18 | 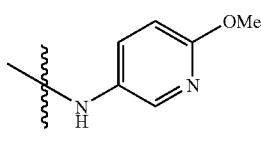 | 5-[(4-Amino-1-piperidinyl)methyl]-N-(6-methoxy-3-pyridinyl)pyrrolo[2,1-f][1,2,4]triazin-4-amine, trifluoroacetic acid salt (1:1). | 354 | 0.98(b) |
| 19 | 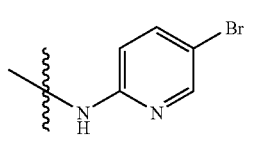 | 5-[(4-Amino-1-piperidinyl)methyl]-N-(5-bromo-2-pyridinyl)pyrrolo[2,1-f][1,2,4]triazin-4-amine, trifluoroacetic acid salt (1:1). | 402 | 1.63(b) |
| 20 | 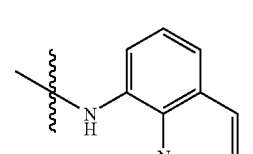 | N-[5-[(4-Amino-1-piperidinyl)methyl]pyrrolo[2,1-f][1,2,4]triazin-4-yl]-8-quinolinamine, trifluoroacetic acid salt (1:1). | 374 | 0.92(b) |
| 21 | 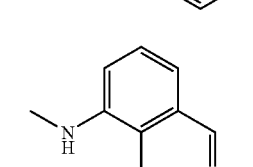 | N-[5-[(4-Amino-1-piperidinyl)methyl]pyrrolo[2,1-f][1,2,4]triazin-4-yl]-5-isoquinolinamine, trifluoroacetic acid salt (1:1). | 374 | 0.59(b) |
| 22 | 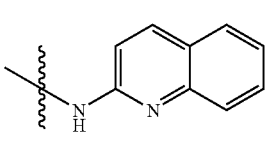 | N-[5-[(4-Amino-1-piperidinyl)methyl]pyrrolo[2,1-f][1,2,4]triazin-4-yl]-2-quinolinamine, trifluoroacetic acid salt (1:1). | 374 | 1.49(b) |

-continued

| Ex. # | R | Compound Name | [M + H] | HPLC Ret Time (min) |
|---|---|---|---|---|
| 23 | 5-chloro-2-pyridinyl-NH- | 5-[(4-Amino-1-piperidinyl)methyl]-N-(5-chloro-2-pyridinyl)pyrrolo[2,1-f][1,2,4]triazin-4-amine, trifluoroacetic acid salt (1:1). | 374 | 1.55(b) |
| 24 | 4-methoxy-6-methyl-2-pyrimidinyl-NH- | 5-[(4-Amino-1-piperidinyl)methyl]-N-(4-methoxy-6-methyl-2-pyrimidinyl)pyrrolo[2,1-f][1,2,4]triazin-4-amine, trifluoroacetic acid salt (1:1). | 369 | 1.03(b) |
| 25 | 6-ethyl-2-pyridinyl-NH- | 5-[(4-Amino-1-piperidinyl)methyl]-N-(6-ethyl-2-pyridinyl)pyrrolo[2,1-f][1,2,4]triazin-4-amine, trifluoroacetic acid salt (1:1). | 352 | 1.91(b) |
| 26 | 6-methoxy-4-pyrimidinyl-NH- | 5-[(4-Amino-1-piperidinyl)methyl]-N-(6-methoxy-4-pyrimidinyl)pyrrolo[2,1-f][1,2,4]triazin-4-amine, trifluoroacetic acid salt (1:1). | 355 | 1.25(b) |
| 27 | 6-isoquinolinyl-NH- | N-[5-[(4-Amino-1-piperidinyl)methyl]pyrrolo[2,1-f][1,2,4]triazin-4-yl]-6-isoquinolinamine, trifluoroacetic acid salt (1:1). | 374 | 1.85(b) |
| 28 | 3-methyl-2-pyridinyl-NH- | 5-[(4-Amino-1-piperidinyl)methyl]-N-(3-methyl-2-pyridinyl)pyrrolo[2,1-f][1,2,4]triazin-4-amine, trifluoroacetic acid salt (1:1). | 338 | 1.67(b) |
| 29 | 4-ethyl-2-pyridinyl-NH- | 5-[(4-Amino-1-piperidinyl)methyl]-N-(4-ethyl-2-pyridinyl)pyrrolo[2,1-f][1,2,4]triazin-4-amine, trifluoroacetic acid salt (1:1). | 352 | 1.00(b) |
| 30 | 6-bromo-2-pyridinyl-NH- | 5-[(4-Amino-1-piperidinyl)methyl]-N-(6-bromo-2-pyridinyl)pyrrolo[2,1-f][1,2,4]triazin-4-amine, trifluoroacetic acid salt (1:1). | 402 | 1.62(b) |

-continued

| Ex. # | R | Compound Name | [M + H] | HPLC Ret Time (min) |
|---|---|---|---|---|
| 31 | (2,6-dimethyl-4-pyrimidinyl)amino | 5-[(4-Amino-1-piperidinyl)methyl]-N-(2,6-dimethyl-4-pyrimidinyl)pyrrolo[2,1-f][1,2,4]triazin-4-amine, trifluoroacetic acid salt (1:1). | 353 | 0.89(b) |
| 32 | [6-(methoxymethyl)-2-pyridinyl]amino | 5-[(4-Amino-1-piperidinyl)methyl]-N-[6-(methoxymethyl)-4-pyrimidinyl]- pyrrolo[2,1-f][1,2,4]triazin-4-amine | 369 | 1.12(b) |
| 33 | (6-methyl-3-pyridazinyl)amino | 5-[(4-Amino-1-piperidinyl)methyl]-N-(6-methyl-3-pyridazinyl)pyrrolo[2,1-f][1,2,4]triazin-4-amine, trifluoroacetic acid salt (1:1). | 339 | 0.88(b) |
| 34 | (5-methyl-3-pyridazinyl)amino | 5-[(4-Amino-1-piperidinyl)methyl]-N-(5-methyl-3-pyridazinyl)pyrrolo[2,1-f][1,2,4]triazin-4-amine, trifluoroacetic acid salt (1:1). | 339 | 0.97(b) |
| 35 | (6-chloro-3-pyridazinyl)amino | 5-[(4-Amino-1-piperidinyl)methyl]-N-(6-chloro-3-pyridazinyl)pyrrolo[2,1-f][1,2,4]triazin-4-amine, trifluoroacetic acid salt (1:1). | 359 | 1.29(b) |
| 36 | (2-chloro-4-pyridinyl)amino | 5-[(4-Amino-1-piperidinyl)methyl]-N-(2-chloro-4-pyridinyl)pyrrolo[2,1-f][1,2,4]triazin-4-amine, trifluoroacetic acid salt (1:1). | 358 | 1.11(b) |
| 37 | (6-fluoro-5-methyl-3-pyridinyl)amino | 5-[(4-Amino-1-piperidinyl)methyl]-N-(6-fluoro-5-methyl-3-pyridinyl)pyrrolo[2,1-f][1,2,4]triazin-4-amine, trifluoroacetic acid salt (1:1). | 35 | 1.05(b) |

EXAMPLES 38–121

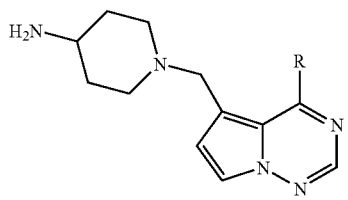

Method One:

Compounds (with HPLC note (a)) were prepared by the following standard method.

In a 1 dram vial was added 1D (55.0 mg, 0.16 mmol), aniline (0.16 mmol, 1.0 eq) and $CH_3CN$ (1 ml). The mixture was shaken at 65° C. overnight. To this mixture was added piperidin-4-yl-carbamic acid tert-butyl ester (34.9 mg, 0.17 mmol) followed by addition of DIEA (28 μl, 0.16 mmol). The reaction was continued at 65° C. for 3 h. The mixture was concentrated; the residue was purified by Prep HPLC, and the desired fraction was collected and concentrated. The obtained residue was dried under high vacuum overnight.

To the above residue was added $CH_2Cl_2$ (1.5 ml) and TFA (0.2 ml), and the reaction mixture was shaken at rt for 2 h. The mixture was concentrated, and dried in speed vacuum overnight to give the solid product. Further Prep HPLC was used only when the solid was impure.

Method Two:

Compounds (with HPLC note (b)) were prepared by the following standard method.

A mixture of 1D (75 mg, 0.216 mmol) and anilines (1.0 eq, 0.216 mmol) in N,N-dimethyl acetamide (0.5 ml) in a small vial was heated at 70° C. for 3–5 hrs until a clear solution obtained. HPLC was used to follow the progress of the reaction. The reaction mixture was cooled to rt and piperidin-4-yl-carbamic acid tert-butyl ester (43 mg, 0.216 mmol) was added, followed by N,N-diisopropylethylamine (75 μl). The reaction mixture again was heated to 70° C. overnight. Upon cooling, the reaction mixture was diluted with $CH_2Cl_2$ (0.5 ml) and cooled to 0° C. TFA (1.0 ml) was added and the mixture was stirred at ambient temperature overnight. The solvent was removed under reduced pressure (speedVac) and the residue was taken into methanol and purified by Prep HPLC to give the desired product.

| Ex. | R | Compound Name | [M + H] | HPLC Ret Time (min) |
|---|---|---|---|---|
| 38 | ![R group with NHMe benzamide] | 3-[[5-[(4-Amino-1-piperidinyl)methyl]pyrrolo[2,1-f][1,2,4]triazin-4-yl]amino]-N-methyl benzamide | 380.25 | 0.91(a) |
| 39 | ![R group with 4-chlorophenoxy] | 5-[(4-Amino-1-piperidinyl)methyl]-N-[3-(4-chlorophenoxy)phenyl]pyrrolo[2,1-f][1,2,4]triazin-4-amine | 449.20 | 2.59(a) |
| 40 | ![R group with phenylmethoxy] | 5-[(4-Amino-1-piperidinyl)methyl]-N-[3-(phenyl-methoxy)phenyl]pyrrolo[2,1-f][1,2,4]triazin-4-amine | 429.26 | 2.183(a) |
| 41 | ![R group with 4-ethylphenyl] | 5-[(4-Amino-1-piperidinyl)methyl]-N-(4-ethyl-phenyl)pyrrolo[2,1-f][1,2,4]triazin-4-amine | 351.28 | 1.64(a) |
| 42 | ![R group with benzamide NH2] | 3-[[5-[(4-Amino-1-piperidinyl)methyl]pyrrolo[2,1-f][1,2,4]triazin-4-yl]amino]benzamide | 366.25 | 0.76(a) |

-continued

| Ex. | R | Compound Name | [M + H] | HPLC Ret Time (min) |
|---|---|---|---|---|
| 43 | 3-(1-methylethoxy)phenyl-NH- | 5-[(4-Amino-1-piperidinyl)methyl]-N-[3-(1-methylethoxy)phenyl]pyrrolo[2,1-f][1,2,4]triazin-4-amine | 381.27 | 1.66(a) |
| 44 | 3-ethoxyphenyl-NH- | 5-[(4-Amino-1-piperidinyl)methyl]-N-(3-ethoxy-phenyl)pyrrolo[2,1-f][1,2,4]triazin-4-amine | 367.26 | 1.44(a) |
| 45 | 3-(trifluoromethyl)phenyl-NH- | 5-[(4-Amino-1-piperidinyl)methyl]-N-[3-(trifluoro-methyl)phenyl]pyrrolo[2,1-f][1,2,4]triazin-4-amine | 391.18 | 1.71(a) |
| 46 | 3-(1-methylethyl)phenyl-NH- | 5-[(4-Amino-1-piperidinyl)methyl]-N-[3-(1-methyl-ethyl)phenyl]pyrrolo[2,1-f][1,2,4]triazin-4-amine | 365.29 | 1.89(a) |
| 47 | 3-(trifluoromethoxy)phenyl-NH- | 5-[(4-Amino-1-piperidinyl)methyl]-N-[3-(trifluoro-methoxy)phenyl]pyrrolo[2,1-f][1,2,4]triazin-4-amine | 407.19 | 1.90(a) |
| 48 | 3,5-dimethoxyphenyl-NH- | 5-[(4-Amino-1-piperidinyl)methyl]-N-(3,5-dimethoxy-phenyl)pyrrolo[2,1-f][1,2,4]triazin-4-amine | 383.24 | 1.32(a) |
| 49 | 3,5-dichlorophenyl-NH- | 5-[(4-Amino-1-piperidinyl)methyl]-N-(3,5-dichloro-phenyl)pyrrolo[2,1-f][1,2,4]triazin-4-amine | 391.13 | 1.85(a) |
| 50 | 4-CN-2-Cl-phenyl-NH- | 4-[[5-[(4-Amino-1-piperidinyl)methyl]pyrrolo[2,1-f][1,2,4]triazin-4-yl]amino]-2-chlorobenzonitrile | 382.19 | 1.63(a) |
| 51 | 3,5-dimethylphenyl-NH- | 5-[(4-Amino-1-piperidinyl)methyl]-N-(3,5-dimethyl-phenyl)pyrrolo[2,1-f][1,2,4]triazin-4-amine | 351.28 | 1.56(a) |

-continued

| Ex. | R | Compound Name | [M + H] | HPLC Ret Time (min) |
|---|---|---|---|---|
| 52 | 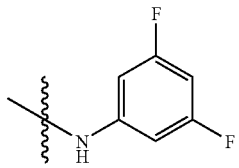 | 5-[(4-Amino-1-piperidinyl)methyl]-N-(3,5-difluorophenyl)pyrrolo[2,1-f][1,2,4]triazin-4-amine | 359.24 | 1.14(a) |
| 53 | 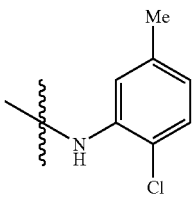 | 5-[(4-Amino-1-piperidinyl)methyl]-N-(2-chloro-5-methylphenyl)pyrrolo[2,1-f][1,2,4]triazin-4-amine | 371.21 | 1.38(a) |
| 54 | 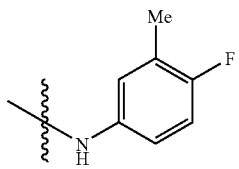 | 5-[(4-Amino-1-piperidinyl)methyl]-N-(4-fluoro-3-methylphenyl)pyrrolo[2,1-f][1,2,4]triazin-4-amine | 355.27 | 1.33(a) |
| 55 | 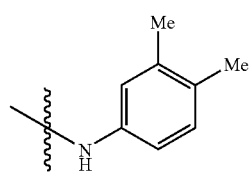 | 5-[(4-Amino-1-piperidinyl)methyl]-N-(3,4-dimethylphenyl)pyrrolo[2,1-f][1,2,4]triazin-4-amine | 351.28 | 1.58(a) |
| 56 | 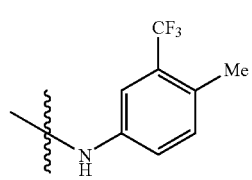 | 5-[(4-Amino-1-piperidinyl)methyl]-N-[4-methyl-3-(trifluoromethyl)phenyl]pyrrolo[2,1-f][1,2,4]triazin-4-amine | 405.21 | 2.10(a) |
| 57 | 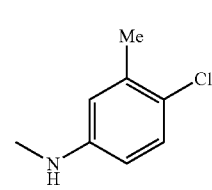 | 5-[(4-Amino-1-piperidinyl)methyl]-N-(4-chloro-3-methylphenyl)pyrrolo[2,1-f][1,2,4]triazin-4-amine | 371.21 | 1.74(a) |
| 58 | 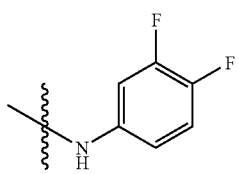 | 5-[(4-Amino-1-piperidinyl)methyl]-N-(3,4-difluorophenyl)pyrrolo[2,1-f][1,2,4]triazin-4-amine | 359.23 | 1.16(a) |
| 59 | 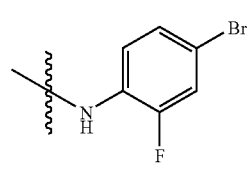 | 5-[(4-Amino-1-piperidinyl)methyl]-N-(4-bromo-2-fluorophenyl)pyrrolo[2,1-f][1,2,4]triazin-4-amine | 419.08 | 1.55(a) |

-continued

| Ex. | R | Compound Name | [M + H] | HPLC Ret Time (min) |
|---|---|---|---|---|
| 60 | 2-fluoro-4-methylphenyl-NH- | 5-[(4-Amino-1-piperidinyl)methyl]-N-(2-fluoro-4-methylphenyl)pyrrolo[2,1-f][1,2,4]triazin-4-amine | 355.22 | 1.42(a) |
| 61 | 4-bromo-2-chlorophenyl-NH- | 5-[(4-Amino-1-piperidinyl)methyl]-N-(4-bromo-2-chlorophenyl)pyrrolo[2,1-f][1,2,4]triazin-4-amine | 435.08 | 1.68(a) |
| 62 | 2,4-dimethylphenyl-NH- | 5-[(4-Amino-1-piperidinyl)methyl]-N-(2,4-dimethyl-phenyl)pyrrolo[2,1-f][1,2,4]triazin-4-amine | 351.24 | 1.36(a) |
| 63 | 4-bromo-3-(trifluoromethyl)phenyl-NH- | 5-[(4-Amino-1-piperidinyl)methyl]-N-[4-bromo-3-(trifluoromethyl)phenyl]pyrrolo[2,1-f][1,2,4]triazin-4-amine | 469.12 | 2.35(a) |
| 64 | 4-chloro-3-(trifluoromethyl)phenyl-NH- | 5-[(4-Amino-1-piperidinyl)methyl]-N-[4-chloro-3-(trifluoromethyl)phenyl]pyrrolo[2,1-f][1,2,4]triazin-4-amine | 425.13 | 2.26(a) |
| 65 | 3-fluoro-4-methylphenyl-NH- | 5-[(4-Amino-1-piperidinyl)methyl]-N-(3-fluoro-4-methylphenyl)pyrrolo[2,1-f][1,2,4]triazin-4-amine | 355.22 | 1.51(a) |
| 66 | 3-bromo-4-(trifluoromethoxy)phenyl-NH- | 5-[(4-Amino-1-piperidinyl)methyl]-N-[3-bromo-4-(trifluoromethoxy)phenyl]pyrrolo[2,1-f][1,2,4]triazin-4-amine | 485.11 | 2.43(a) |
| 67 | 4-fluoro-3-(trifluoromethyl)phenyl-NH- | 5-[(4-Amino-1-piperidinyl)methyl]-N-[4-fluoro-3-(trifluoromethyl)phenyl]pyrrolo[2,1-f][1,2,4]triazin-4-amine | 409.17 | 1.88(a) |
| 68 | 3-fluoro-4-methoxyphenyl-NH- | 5-[(4-Amino-1-piperidinyl)methyl]-N-(3-fluoro-4-methoxyphenyl)pyrrolo[2,1-f][1,2,4]triazin-4-amine | 371.23 | 0.76(a) |
| 69 | 2,3-dihydro-1,4-benzodioxin-6-yl-NH- | 5-[(4-Amino-1-piperidinyl)methyl]-N-(2,3-dihydro-1,4-benzodioxin-6-yl)pyrrolo[2,1-f][1,2,4]triazin-4-amine | 381.23 | 1.24(a) |

-continued

| Ex. | R | Compound Name | [M + H] | HPLC Ret Time (min) |
|---|---|---|---|---|
| 70 | (2,5-difluorophenyl)-NH- | 5-[(4-Amino-1-piperidinyl)methyl]-N-(2,5-difluorophenyl)pyrrolo[2,1-f][1,2,4]triazin-4-amine | 359.20 | 1.13(a) |
| 71 | (2-fluoro-5-methylphenyl)-NH- | 5-[(4-Amino-1-piperidinyl)methyl]-N-(2-fluoro-5-methylphenyl)pyrrolo[2,1-f][1,2,4]triazin-4-amine | 355.22 | 1.35(a) |
| 72 | (4-chloro-2-fluorophenyl)-NH- | 5-[(4-Amino-1-piperidinyl)methyl]-N-(4-chloro-2-fluorophenyl)pyrrolo[2,1-f][1,2,4]triazin-4-amine | 375.19 | 1.45(a) |
| 73 | (3-methoxy-4-methylphenyl)-NH- | 5-[(4-Amino-1-piperidinyl)methyl]-N-(3-methoxy-4-methylphenyl)pyrrolo[2,1-f][1,2,4]triazin-4-amine | 367.25 | 1.48(a) |
| 74 | (5-chloro-2-fluorophenyl)-NH- | 5-[(4-Amino-1-piperidinyl)methyl]-N-(5-chloro-2-fluorophenyl)pyrrolo[2,1-f][1,2,4]triazin-4-amine | 375.18 | 1.44(a) |
| 75 | (2,3-difluorophenyl)-NH- | 5-[(4-Amino-1-piperidinyl)methyl]-N-(2,3-difluorophenyl)pyrrolo[2,1-f][1,2,4]triazin-4-amine | 359.21 | 1.16(a) |
| 76 | (5,6,7,8-tetrahydro-1-naphthalenyl)-NH- | 5-[(4-Amino-1-piperidinyl)methyl]-N-(5,6,7,8-tetrahydro-1-naphthalenyl)pyrrolo[2,1-f][1,2,4]triazin-4-amine | 377 | 1.79(b) |
| 77 | 1,3-benzodioxol-5-yl-NH- | 5-[(4-Amino-1-piperidinyl)methyl]-N-1,3-benzodioxol-5-ylpyrrolo[2,1-f][1,2,4]triazin-4-amine | 367 | 1.17(b) |
| 78 | (3-chloro-4-methylphenyl)-N(Me)- | 5-[(4-aminopiperidin-1-yl)methyl]-N-(3-chloro-4-methylphenyl)pyrrolo[2,1-f][1,2,4]triazin-4-amine | 371 | 1.793 |

-continued

| Ex. | R | Compound Name | [M + H] | HPLC Ret Time (min) |
|---|---|---|---|---|
| 79 | 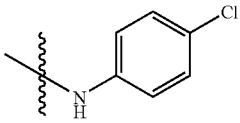 | 5-[(4-Amino-1-piperidinyl)methyl]-N-(4-chloro-phenyl)pyrrolo[2,1-f][1,2,4]triazin-4-amine | 357 | 1.44(b) |
| 80 | 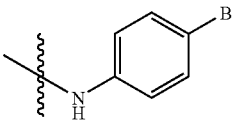 | 5-[(4-Amino-1-piperidinyl)methyl]-N-(4-bromo-phenyl)pyrrolo[2,1-f][1,2,4]triazin-4-amine | 401 | 1.56(b) |
| 81 | 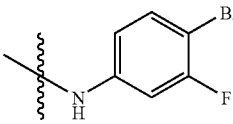 | 5-[(4-Amino-1-piperidinyl)methyl]-N-(4-bromo-3-fluorophenyl)pyrrolo[2,1-f][1,2,4]triazin-4-amine | 419 | 1.68(b) |
| 82 | 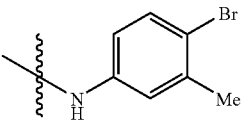 | 5-[(4-Amino-1-piperidinyl)methyl]-N-(4-bromo-3-methylphenyl)pyrrolo[2,1-f][1,2,4]triazin-4-amine | 415 | 1.85(b) |
| 83 | 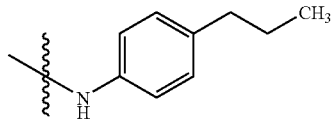 | 5-[(4-Amino-1-piperidinyl)methyl]-N-(4-propyl-phenyl)pyrrolo[2,1-f][1,2,4]triazin-4-amine | 365 | 1.98(b) |
| 84 | 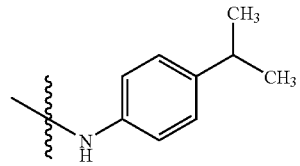 | 5-[(4-Amino-1-piperidinyl)methyl]-N-[4-(1-methyl-ethyl)phenyl]pyrrolo[2,1-f][1,2,4]triazin-amine | 365 | 1.93(b) |
| 85 | 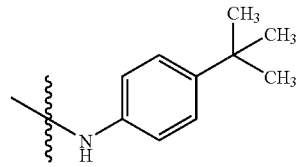 | 5-[(4-Amino-1-piperidinyl)methyl]-N-[4-(1,1-dimethyl-ethyl)phenyl]pyrrolo[2,1-f][1,2,4]triazin-4-amine | 379 | 2.21(b) |
| 86 | 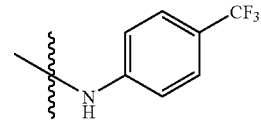 | 5-[(4-Amino-1-piperidinyl)methyl]-N-[4-(trifluoro-methyl)phenyl]pyrrolo[2,1-f][1,2,4]triazin-4-amine | 391 | 1.83(b) |
| 87 | 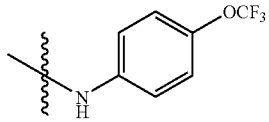 | 5-[(4-Amino-1-piperidinyl)methyl]-N-[4-(trifluoro-methoxy)phenyl]pyrrolo[2,1-f][1,2,4]triazin-4-amine | 407 | 1.88(b) |
| 88 | 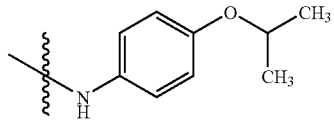 | 5-[(4-Amino-1-piperidinyl)methyl]-N-[4-(1-methyl-ethoxy)phenyl]pyrrolo[2,1-f][1,2,4]triazin-4-amine | 381 | 1.68(b) |

-continued

| Ex. | R | Compound Name | [M + H] | HPLC Ret Time (min) |
|---|---|---|---|---|
| 89 | 3,4-dimethoxyphenyl-NH- | 5-[(4-Amino-1-piperidinyl)methyl]-N-(3,4-dimethoxyphenyl)pyrrolo[2,1-f][1,2,4]triazin-4-amine | 383 | 1.09(b) |
| 90 | 4-acetylphenyl-NH- | 1-[4-[[5-[(4-Amino-1-piperidinyl)methyl]pyrrolo[2,1-f][1,2,4]triazin-4-yl]amino]phenyl]ethanone | 365 | 1.44(b) |
| 91 | 4-ethoxyphenyl-NH- | 5-[(4-Amino-1-piperidinyl)methyl]-N-(4-ethoxyphenyl)pyrrolo[2,1-f][1,2,4]triazin-4-amine | 367 | 1.44(b) |
| 92 | 4-(difluoromethoxy)phenyl-NH- | 5-[(4-Amino-1-piperidinyl)methyl]-N-[4-(difluoromethoxy)phenyl]pyrrolo[2,1-f][1,2,4]triazin-4-amine | 389 | 1.45(b) |
| 93 | 4-carbamoylphenyl-NH- | 4-[[5-[(4-Amino-1-piperidinyl)methyl]pyrrolo[2,1-f][1,2,4]triazin-4-yl]amino]benzamide | 366 | 0.82(b) |
| 94 | 4-acetamidophenyl-NH- | N-[4-[[5-[(4-Amino-1-piperidinyl)methyl]pyrrolo[2,1-f][1,2,4]triazin-4-yl]amino]phenyl]acetamide. | 380 | 1.04(b) |
| 95 | 2-cyano-5-methylphenyl-NH- | 2-[[5-[(4-Amino-1-piperidinyl)methyl]pyrrolo[2,1-f][1,2,4]triazin-4-yl]amino]-4-methylbenzonitrile. | 362 | 2.40(b) |
| 96 | 2-cyano-5-chlorophenyl-NH- | 2-[[4-[(4-Amino-1-piperidinyl)methyl]pyrrolo[2,1-f][1,2,4]triazin-4-yl]amino]-4-chlorobenzonitrile. | 382 | 1.12(b) |
| 100 | 4-morpholinophenyl-NH- | 5-[(4-Amino-1-piperidinyl)methyl]-N-[4-(4-morpholinyl)phenyl]pyrrolo[2,1-f][1,2,4]triazin-4-amine. | 408 | 1.12(b) |
| 102 | 2,3-dihydro-1H-inden-5-yl-NH- | 5-[(4-Amino-1-piperidinyl)methyl]-N-(2,3-dihydro-1H-inden-5-yl)pyrrolo[2,1-f][1,2,4]triazin-4-amine. | 363 | 1.78(b) |

-continued

| Ex. | R | Compound Name | [M + H] | HPLC Ret Time (min) |
|---|---|---|---|---|
| 103 | 3-cyanophenyl-NH- | 3-[[5-[(4-Amino-1-piperidinyl)methyl]pyrrolo[2,1-f][1,2,4]triazin-4-yl]amino]benzonitrile, trifluoroacetic acid salt (1:1). | 348 | 1.05(a) |
| 105 | 3-methoxyphenyl-NH- | 5-[(4-Amino-1-piperidinyl)methyl]-N-(3-methoxy-phenyl)pyrrolo[2,1-f][1,2,4]triazin-4-amine, trifluoroacetic acid salt (1:1) | 353 | 1.17(a) |
| 106 | 3-methylphenyl-NH- | 5-[(4-Amino-1-piperidinyl)methyl]-N-(3-methyl-phenyl)pyrrolo[2,1-f][1,2,4]triazin-4-amine, trifluoroacetic acid salt (1:1) | 337 | 1.25(a) |
| 107 | 3-ethynylphenyl-NH- | 5-[(4-Amino-1-piperidinyl)methyl]-N-(3-ethynylphenyl)pyrrolo[2,1-f][1,2,4]triazin-4-amine | 347 | 1.35(a) |
| 108 | 3,4-dichlorophenyl-NH- | 5-[4-(4-Amino-1-piperidinyl)methyl]-N-(3,4-dichloro phenyl)pyrrolo[2,1-f][1,2,4]triazin-4-amine. | 391 | 1.91(a) |
| 109 | 3-chlorophenyl-NH- | 5-[(4-Amino-1-piperidinyl)methyl]-N-(3-chlorophenyl) pyrrolo[2,1-f][1,2,4]triazin-4-amine. | 357 | 0.75(a) |
| 110 | 3-chloro-4-methoxyphenyl- | 5-[(4-aminopiperidin-1-yl)methyl]-N-(3-chloro-4-methoxyphenyl)pyrrolo[2,1-f][1,2,4]triazin-4-amine | 387 | 1.530 |
| 111 | 3-bromophenyl- | 5-[(4-aminopiperidin-1-yl)methyl]-N-(3-bromophenyl)pyrrolo[2,1-f][1,2,4]triazin-4-amine | 401 | 1.560 |
| 112 | 4-fluorophenyl- | 5-[(4-aminopiperidin-1-yl)methyl]-N-(4-fluorophenyl)pyrrolo[2,1-f][1,2,4]triazin-4-amine | 341 | 1.020 |
| 113 | 2-methylphenyl- | 5-[(4-aminopiperidin-1-yl)methyl]-N-(2-methylphenyl)pyrrolo[2,1-f][1,2,4]triazin-4-amine | 337 | 1.030 |

-continued

| Ex. | R | Compound Name | [M + H] | HPLC Ret Time (min) |
|---|---|---|---|---|
| 114 | 3-fluorophenyl | 5-[(4-aminopiperidin-1-yl)methyl]-N-(3-fluorophenyl)pyrrolo[2,1-f][1,2,4]triazin-4-amine | 341 | 1.110 |
| 115 | 4-methylphenyl | 5-[(4-aminopiperidin-1-yl)methyl]-N-(4-methylphenyl)pyrrolo[2,1-f][1,2,4]triazin-4-amine | 337 | 1.310 |
| 116 | 4-methoxyphenyl | 5-[(4-aminopiperidin-1-yl)methyl]-N-(4-methoxyphenyl)pyrrolo[2,1-f][1,2,4]triazin-4-amine | 353 | 1.170 |
| 117 | 2-fluoro-5-(...)benzonitrile | 5-({5-[(4-aminopiperidin-1-yl)methyl]pyrrolo[2,1-f][1,2,4]triazin-4-yl}amino)-2-fluorobenzonitrile | 366 | 1.103 |
| 118 | 3-ethynyl-4-fluorophenyl | 5-[(4-aminopiperidin-1-yl)methyl]-N-(3-ethynyl-4-fluorophenyl)-pyrrolo[2,1-f][1,2,4]triazin-4-amine | 365 | 1.350 |
| 119 | 3-(hydroxymethyl)phenyl | [3-({5-[(4-aminopiperidin-1-yl)methyl]pyrrolo[2,1-f][1,2,4]triazin-4-yl}amino)phenyl]methanol | 353 | 0.837 |
| 120 | 4-fluoro-3-methoxyphenyl | 5-[(4-aminopiperidin-1-yl)methyl]-N-(4-fluoro-3-methoxyphenyl)pyrrolo[2,1-f][1,2,4]triazin-4-amine | 371 | 1.162 |
| 121 | 3-(difluoromethoxy)phenyl | 5-[(4-aminopiperidin-1-yl)methyl]-N-[3-(difluoromethoxy)phenyl]pyrrolo[2,1-f][1,2,4]triazin-4-amine | 389 | 1.370 |

53

HPLC conditions:

(a): (YMC S5 ODS column 4.6×50 mm, 10–90% aqueous methanol over 4 minutes containing 0.2% H$_3$PO$_4$, 3 ml/min, monitoring at 220 nm)

(b): (Chromolith SpeedROD 4.6×50 mm, 10–90% aqueous methanol over 4 minutes containing 0.1% TFA, 4 ml/min, monitoring at 220 nm)

Note: Examples 97–99, 101 and 104 have been deleted from the table as duplicates.

54

EXAMPLES 122–132

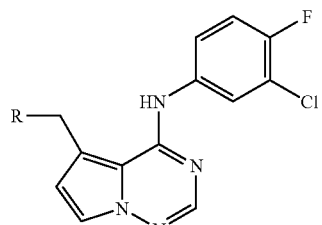

Compounds 122–132 were prepared from Compound 1D, 3-chloro-4-fluoro-phenylamine and corresponding amines or Boc protected amines by a route analogous to that used for the preparation of Compounds 38–121.

| Ex. | R | Compound Name | [M + H] | HPLC Ret Time (min) |
|---|---|---|---|---|
| 122 | (3S)-3-aminopiperidinyl | 5-[[(3S)-3-Amino-1-piperidinyl]methyl]-N-(3-chloro-4-fluorophenyl)pyrrolo[2,1-f][1,2,4]triazin-4-amine. | 375 | 1.82(b) |
| 123 | (3R)-3-aminopiperidinyl | 5-[[(3R)-3-Amino-1-piperidinyl]methyl]-N-(3-chloro-4-fluorophenyl)pyrrolo[2,1-f][1,2,4]triazin-4-amine. | 375 | 1.83(b) |
| 124 | 3,4-dihydroxypiperidinyl | 1-[[4-[(3-Chloro-4-fluorophenyl)amino]pyrrolo[2,1-f][1,2,4]triazin-5-yl]methyl]-(3R,4S)-rel-3,4-piperidinediol. | 392 | 1.74(b) |
| 125 | 3,6-dihydro-2H-pyridinyl | N-(3-Chloro-4-fluorophenyl)-5-[(3,6-dihydro-1(2H)-pyridinyl)methyl]pyrrolo[2,1-f][1,2,4]triazin-4-amine. | 358 | 2.12(b) |
| 126 | 4-amino-4-methylpiperidinyl | 5-[[(3R,4R)-rel-4-Amino-3-methyl-1-piperidinyl]methyl]-(3-chloro-4-fluorophenyl)pyrrolo[2,1-f][1,2,4]triazin-4-amine, trifluoroacetic acid salt (1:1). | 389 | 1.71(b) |
| 127 | 4-amino-3-methylpiperidinyl | 5-[[(3R,4S)-rel-4-Amino-3-methyl-1-piperidinyl]methyl]-N-(3-chloro-4-fluorophenyl)pyrrolo[2,1-f][1,2,4]triazin-4-amine, trifluoroacetic acid salt (1:1). | 389 | 1.557(b) |

-continued

| Ex. | R | Compound Name | [M + H] | HPLC Ret Time (min) |
|---|---|---|---|---|
| 128 | (piperazine with CH2OH, 2S) | 4-[[4-[(3-Chloro-4-fluorophenyl)amino]pyrrolo[2,1-f][1,2,4]triazin-5-yl]methyl]-(2S)-2-piperazinemethanol, trifluoroacetic acid salt (1:1). | 391 | 1.97(b) |
| 129 | (3R,4S)-4-amino-3-methylpiperidine | 5-[[(3R,4S)-4-Amino-3-methyl-1-piperidinyl]methyl]-N-(3-chloro-4-fluorophenyl)pyrrolo[2,1-f][1,2,4]triazin-4-amine | 389 | 1.557(b) |
| 130 | (3S,4R)-rel-4-amino-3-methylpiperidine | 5-[[(3S,4R)-rel-4-Amino-3-methyl-1-piperidinyl]methyl]-N-(3-chloro-4-fluorophenyl)pyrrolo[2,1-f][1,2,4]triazin-4-amine, trifluoroacetic acid salt (1:1). | 389 | 1.557(b) |
| 131 | 4-(methylamino)piperidine | N-(3-chloro-4-fluoro-phenyl)-5-{[4-(methyl-amino)piperidin-1-yl]-methyl}pyrrolo[2,1-f]-[1,2,4]triazin-4-amine | 389 | 1.000$^a$ |
| 132 | 4-amino-4-methylpiperidine | 5-[(4-amino-4-methyl-piperidin-1-yl)methyl]-N-(3-chloro-4-fluoro-phenyl)pyrrolo[2,1-f]-[1,2,4]triazin-4-amine | 389 | 1.030$^a$ |

EXAMPLE 133

5-[(4-Amino-1-piperazinyl)methyl]-N-(3-chloro-4-fluorophenyl)pyrrolo[2,1-f][1,2,4]triazin-4-amine

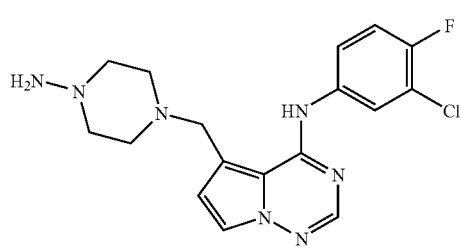

133A Preparation of (5-{[bis-(2-chloro-ethyl)-amino]-methyl}-pyrrolo[2,1-f][1,2,4]triazin-4-yl)-(3-chloro-4-fluoro-phenyl)-amine

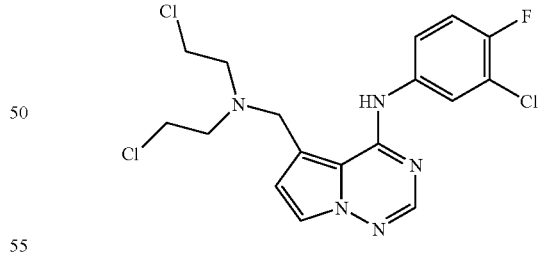

A mixture of Compound 1E (50 mg, 0.1 mmol), bis-(2-chloroethyl)amine hydrochloride (18 mg, 0.1 mmol), DIEA (36 μl, 0.2 mmol) in $CH_3CN$ (0.5 ml) was heated to 60° C. for 3 h. The mixture was cooled to rt and concentrated to give Compound 133A which was used directly in next step. 133A had an analytical HPLC retention time=2.986 min. (Chromolith SpeedROD 4.6×50 mm, 10–90% aqueous methanol over 4 minutes containing 0.1% TFA, 4 ml/min, monitoring at 220 nm) and a LC/MS $M^++1=416$.

The crude 133A from the last step was taken into neat anhydrous N₂H₄ (0.5 ml) and heated at 100° C. for several hours. The mixture was cooled to rt, diluted with H₂O and extracted with CH₂Cl₂. The combined extracts were washed with brine, dried over Na₂SO₄ and concentrated in vacuo. The residue was purified by prep HPLC to give, after neutralization and extraction (with CH₂Cl₂), Compound 133 (38.8 mg, 100% for two steps). Analytical HPLC retention time=1.709 min. (Chromolith SpeedROD 4.6×50 mm, 10–90% aqueous methanol over 4 minutes containing 0.1% TFA, 4 ml/min, monitoring at 220 nm) and a LC/MS M⁺+1=376.

EXAMPLE 134

(3-Chloro-4-fluoro-phenyl)-[5-(morpholin-2-yl-methoxymethyl)-pyrrolo[2,1-f][1,2,4]triazin-4-yl]-amine

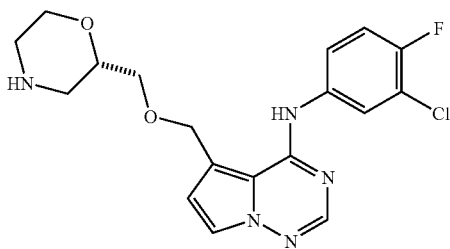

134A Preparation of 2-(4-Methylsulfanyl-pyrrolo[2,1-f][1,2,4]triazin-5-ylmethoxymethyl)-morpholine-4-carboxylic acid tert-butyl ester

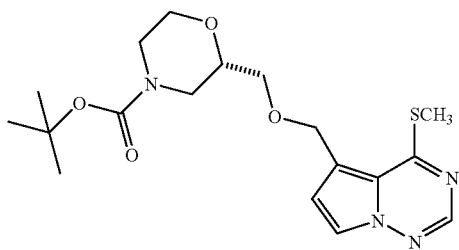

A solution of Compound 1A (1.0 g, 5.6 mmol) in CCl₄ (50 mL) was purged with nitrogen for one hour. Benzoyl peroxide (270 mg, 1.12 mmol) was added and the reaction mixture was heated to 86° C. N-bromosuccinimide (1.04 g, 5.88 mmol) was added in one portion. After 30 minutes, the reaction was cooled to room temperature and filtered. The filtrate was concentrated, re-dissolved in toluene (10 mL) and treated with 2-hydroxymethyl-morpholine-4-carboxylic acid tert-butyl ester (1.5 g, 6.9 mmol). The solution was heated to 110° C. for eight hours, cooled to room temperature and concentrated. Flash chromatography on silica (20% EtOAc/Hexanes) afforded the product as a light yellow oil that crystallized upon standing (770 mg, 32%). HPLC t$_R$=3.783 min (YMC S5 ODS 4.6×50 mm, 10–90% aqueous methanol, 4 min gradient, monitored at 220 nm). LC/MS (M+H)=178.

134B Preparation of 2-[4-(3-Chloro-4-fluoro-phenylamino)-pyrrolo[2,1-f][1,2,4]triazin-5-ylmethoxymethyl]-morpholine-4-carboxylic acid tert-butyl ester

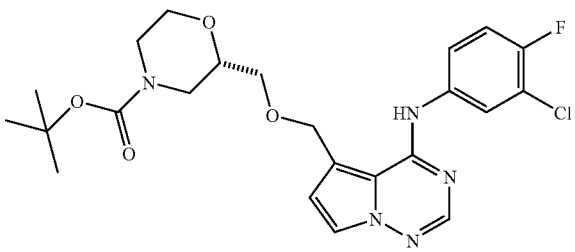

A solution of 2-(4-methylsulfanyl-pyrrolo[2,1-f][1,2,4]triazin-5-ylmethoxymethyl)-morpholine-4-carboxylic acid tert-butyl ester (60 mg, 0.15 mmol) in CH₂Cl₂ (3 mL) was cooled to 0 C. and treated with a solution of mCPBA (56 mg, 0.32 mmol) in CH₂Cl₂ (2 mL). The reaction was stirred for 15 minutes at 0 C. then warmed to room temperature. To this solution was added 3-chloro-4-fluoroaniline and stirred at room temperature for one hour. The resulting orange solution was diluted with CH₂Cl₂ and washed with saturated aqueous NaHCO₃, then saturated aqueous NaCl. The organic layer was dried (Na₂SO₄), filtered and concentrated. Preparative reverse-phase HPLC afforded the desired compound (30 mg, 41%). HPLC t$_R$=4.383 min (YMC S5 ODS 4.6×50 mm, 10–90% aqueous methanol, 4 min gradient, monitored at 220 nm). LC/MS (M+H)=492.

A solution of 134B (30 mg, 0.06 mmol) in CH₂Cl₂ (3 mL) at 0° C. was treated with trifluoroacetic acid (0.3 mL) dropwise. The reaction was stirred for two hours then diluted with CH₂Cl₂ and washed with saturated aqueous NaHCO₃. The organic layer was separated, dried (Na₂SO₄), filtered and concentrated. The crude compound was purified by radial chromatography (1 mm plate, 15% MeOH/CH₂Cl₂ to 30% MeOH/CH₂Cl₂) to afford Compound 134 (17 mg, 67%). HPLC t$_R$=2.83 min (YMC S5 ODS 4.6×50 mm, 10–90% aqueous methanol, 4 min gradient, monitored at 220 nm). LC/MS (M+H)=392.

EXAMPLE 135

4-Amino-1-[[4-[(3-chloro-4-fluorophenyl)amino]pyrrolo[2,1-f][1,2,4]triazin-5-yl]methyl]-(3R,4R)-rel-3-piperidinol

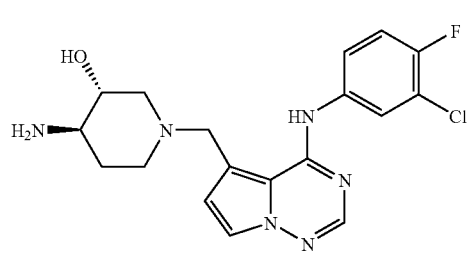

Compound 135A:

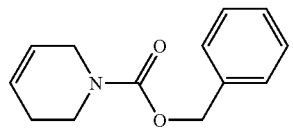

To a solution of 1,2,3,6-tetrahydropyridine (1.66 g, 20.0 mmol) in dry CH$_2$Cl$_2$ (10 mL) was added triethyl amine (3.35 mL, 24.0 mmol), followed by a solution of N-(benzyloxycarbonyloxy)succinimide (5.23 g, 21.0 mmol) in dry CH$_2$Cl$_2$ (10 mL). The reaction mixture was stirred at room temperature overnight. The reaction mixture was diluted with CH$_2$Cl$_2$ (50 mL) and washed with 10% citric acid, sat'd NaHCO$_3$, brine and dried over anhydrous Na$_2$SO$_4$. Concentration under reduced pressure afforded 4.34 g of Compound 135A: (100%) as an oil. Analytical HPLC retention time=2.996 min. (Chromolith SpeedROD column 4.6×50 mm, 10–90% aqueous methanol containing 0.1% TFA over 4 minutes, 4 mL/min, monitoring at 254 nm). $^1$H-NMR (CDCl3): 7.20–7.35 (m, 5H), 5.88 (bs, 1H), 5.60–5.78 (m, 1H), 5.18 (s, 2H), 3.99 (t, J=2.64, 2H), 3.59 (t, J=5.69, 2H), 2.18 (m, 2H).

Compound 135B

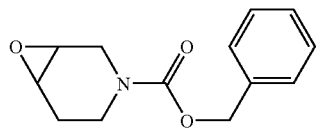

To a solution of Compound 135A (1.1 g, 5.0 mmol) in dry CH$_2$Cl$_2$ (10 mL) cooled at 0° C. was added a solution of 75% m-CPBA (1.38 g, 6.0 mmol) in dry CH$_2$Cl$_2$ (5 mL). The reaction mixture was stirred at 0° C. for 15 min, then at room temperature for 3 hrs. The reaction mixture was diluted with CH$_2$Cl$_2$ (20 mL) and washed with sat'd Na$_2$S2O$_3$, sat'd NaHCO$_3$, brine and dried over anhydrous Na$_2$SO$_4$. Concentration under reduced pressure gave 1.14 g (98%) of Compound 135B as an oil. Analytical HPLC retention time=2.279 min. (Chromolith SpeedROD column 4.6×50 mm, 10–90% aqueous methanol containing 0.1% TFA over 4 minutes, 4 mL/min, monitoring at 254 nm). $^1$H-NMR (CDCl$_3$): 7.20–7.36 (m, 5H), 5.05 (s, 2H), 3.80–3.96 (m, 1H), 3.70 (m, 1H), 3.47 (m, 1H), 3.22 (bs, 1H), 3.07–3.20 (m, 2H)2.00 (m, 1H), 1.87 (m, 1H).

Compounds 135C and 135D:

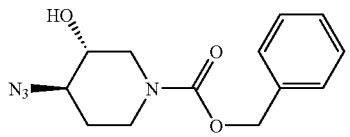

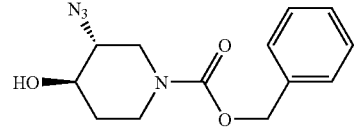

To a solution of Compound 135B (233 mg, 1.0 mmol) in dry DMF (2 mL) was added a solution of sodium azide (100 mg, 1.5 mmol) in a 2:1 mixture of acetone-water (2 mL). The reaction mixture was heated at 80° C. overnight. The solvents were removed under reduced pressure and the residue was taken into EtOAc (20 mL), washed with water, 10% LiCl and brine and dried over anhydrous Na$_2$SO$_4$. Concentration under reduced pressure gave an oil. Flash chromatography (hexane-ethyl acetate: 8:2 to 7:3) on silica gel afforded 180 mg of Compound 135C (early eluent, a major isomer) as an oil and 98 mg of Compound 135D (late eluent, minor isomer) as an oil.

Compound 135C: $^1$H-NMR (CDCl$_3$): 7.28–7.40 (m, 5H), 5.10 (s, 2H), 4.14 (dd, J1=4.03, J2=13.44, 1H), 4.02 (m, 1H), 3.50 (m, 1H), 3.38 (m, 1H), 3.00 (m, 1H), 2.88 (m, 1H), 2.70 and 2.40 (partial m, 1H), 2.00 (m, 1H), 1.50 (m, 1H).

Compound 135D: $^1$H-NMR (CDCl$_3$): 7.20–7.35 (m, 5H), 5.06 (s, 2H), 4.25 and 4.10 (partial m, 1H), 3.99 (d, J=13.44, 1H), 3.50 (m, 1H), 3.22 (m, 1H), 2.85 (t, J=2.69, 1H), 2.73 (m, 1H), 2.40 (m, 1H), 1.90 (m, 1H), 1.45 (m, 1H).

Compound 135E

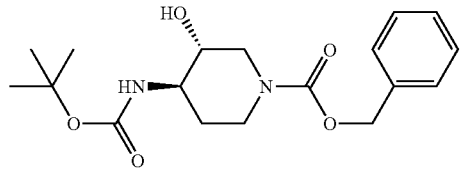

To a solution of Compound 135C (180 mg, 0.65 mmol) in THF (5 mL) was added water (0.05 mL) and triphenylphosphine (340 mg, 1.3 mmol) and the reaction mixture was heated to reflux for 6 hrs. After cooling to room temperature, EtOAc (20 mL) was added to the reaction mixture. The organic layers were extracted with 1.0 N HCl (10 mL×2) and combined aqueous layers were back washed once with EtOAc (5 mL). 1.0 N NaOH was added to the aqueous layers to make it pH 10.0 and the mixture was extracted with EtOAc (20 mL×2). The combined organic layers were dried over anhydrous Na$_2$SO$_4$. Concentration under reduced pressure gave 165 mg of amine intermediate as a colorless oil.

To a solution of 165 mg of amine intermediate in dry CH$_2$Cl$_2$ (4 mL) was added triethylamine (0.11 mL, 0.78 mmol), followed by Boc2O (156 mg, 0.72 mmol). The mixture was stirred at room temperature overnight. The reaction mixture was diluted with CH$_2$Cl$_2$ and washed with sat'd NaHCO$_3$ and dried over anhydrous Na$_2$SO$_4$. Purification by flash chromatography (hexane-EtOAc: 9:1 to 8:2) on silica gel afforded 170 mg of Compound 135E as a white solid. Analytical HPLC retention time=2.859 min. (Chromolith SpeedROD column 4.6×50 mm, 10–90% aqueous methanol containing 0.1% TFA over 4 minutes, 4 mL/min, monitoring at 254 nm) and a LC/MS M$^+$+1=351$^+$. $^1$H-NMR (CDCl$_3$): 7.29–7.40 (m, 5H), 5.10 (s, 2H), 4.61 (bs, 1H), 4.32 (bs, 1H), 3.90–4.30 (m, 1H), 3.30–3.60 (m, 2H), 2.80 (m, 1H), 2.66 (m, 1H), 1.90 (m, 1H), 1.45 (s, 9H), 1.40 (m, 1H).

Compound 135F

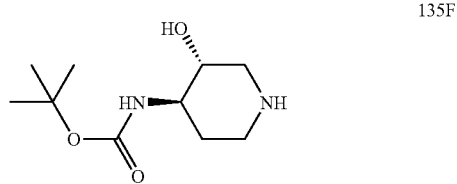

135F

A solution of Compound 135E (170 mg) in 5 mL of MeOH containing 10 mg of Pd(OH)2 was stirred under hydrogen atmosphere (balloon) overnight. The catalyst was removed by filtration and rinsed with MeOH. The combined filtrates were concentrated under reduced pressure to give 138 mg of Compound 135F as an oil. Analytical HPLC retention time=1.270 min. (Chromolith SpeedROD column 4.6×50 mm, 10–90% aqueous methanol containing 0.1% TFA over 4 minutes, 4 mL/min, monitoring at 220 nm) and a LC/MS M$^+$+1=217$^+$.

Compound 135G

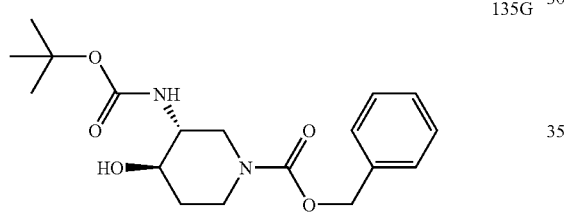

135G

Compound 135G was prepared from Compound 135D in a similar procedure as Compound 135E. Analytical HPLC retention time=2.849 min. (Chromolith SpeedROD column 4.6×50 mm, 10–90% aqueous methanol containing 0.1% TFA over 4 minutes, 4 mL/min, monitoring at 254 nm). $^1$H-NMR (CDCl$_3$): 7.40–7.52 (m, 5H), 5.20 (s, 2H), 4.30 (m, 2H), 3.40 (m, 1H), 2.95 (m, 1H), 2.67 (m, 2H), 2.08 (m, 1H), 1.45–1.96 (m, 3H), 1.45 (s, 9H).

Compound 135H

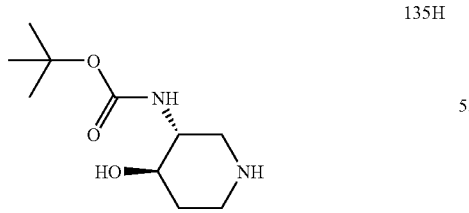

135H

Compound 135H was prepared from Compound 135G in a similar procedure as Compound 135F. Analytical HPLC retention time=1.380 min. (Chromolith SpeedROD column 4.6×50 mm, 10–90% aqueous methanol containing 0.1% TFA over 4 minutes, 4 mL/min, monitoring at 220 nm).

Compound 135 was prepared in a similar manner as Example 1 using Compound 135F and 1E. Compound 135 is a solid with an analytical HPLC retention time=1.666 min. (Chromolith SpeedROD column 4.6×50 mm, 10–90% aqueous methanol containing 0.1 S% TFA over 4 minutes, 4 mL/min, monitoring at 254 nm) and a LC/MS M$^+$+1=391$^+$. $^1$H-NMR (CDCl$_3$): 11.62 (s, 1H), 7.94 (s, 1H), 7.89 (dd, J$_1$=2.60, J$_2$=6.61, 1H), 7.48 (d, J=2.60, 1H), 7.45 (m, 1H), 7.15 (t, J=8.72, 1H), 6.51 (d, J=2.60, 1H), 3.82 (AB, J=13.60, Δv=26.94, 2H), 3.33 (m, 1H), 3.25 (m, 1H), 3.08 (d, J=12.09, 1H), 2.57 (m, 1H), 2.22 (t, J=12.03, 1H), 2.05 (m, 1H), 1.97 (m, 1H), 1.43 (m, 1H).

Alternatively, Compound 135 can be prepared as shown below.

Preparation of Compound 135J

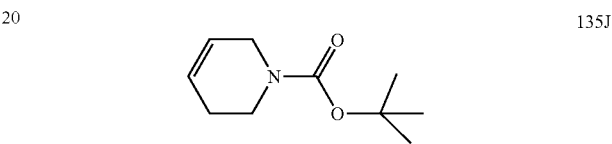

135J

Compound 135J was prepared according to a published literature procedure: Jacob Szmuszkovicz et al., *Heterocycles*, 1994, 39 (1), 163–170.

Preparation of Compound 135K:

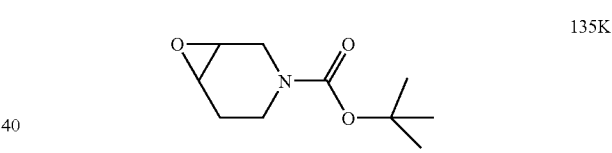

135K

Compound 135K was prepared according to a published literature procedure: Jacob Szmuszkovicz et al., *Heterocycles*, 1994, 39 (1), 163–170.

Preparation of Compound 135L:

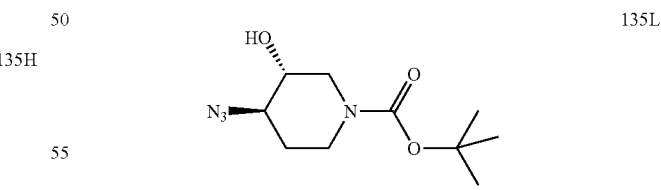

135L

Compound 135L was prepared from Compound 135K in a similar way as Compound 1C. Analytical HPLC retention time=2.323 min. (Chromolith SpeedROD column 4.6×50 mm, 10–90% aqueous methanol containing 0.1% TFA over 4 minutes, 4 mL/min, monitoring at 220 nm). $^1$H-NMR (CDCl3): 4.11 (dd, J1=3.09, J2=13.29, 1H), 3.95 (m, 1H), 3.50 (m, 1H), 3.38 (m, 1H), 2.90 (m, 1H), 2.79 (dd, J1=9.27, J2=13.29, 1H), 2.45 (m, 1H), 2.00 (m, 1H), 1.55 (m, 1H), 1.46 (s, 9H).

Preparation of Compound 135M:

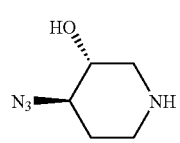

To a solution of Compound 135L (0.6 g, 2.48 mmol) in dry CH$_2$Cl$_2$ cooled at 0° C., was added trifluoroacetic acid (5 mL). The reaction mixture was stirred at 0° C. for 15 min, then warmed to room temperature and stirred for 3 hrs. The solvent and TFA were removed under reduced pressure and the residue was taken into CH$_2$Cl$_2$ (20 mL). The organic layer was washed with sat'd NaHCO$_3$ and the aqueous layer was supersaturated with solid NaCl, and back extracted with EtOAc (15 mL×10). The combined organic extracts were dried over anhydrous Na2SO4. Concentration in vacuo gave 350 mg of Compound 135M as an oil. $^1$H-NMR (CDCl$_3$+CD$_3$OD): 3.55 (m, 1H), 3.43 (m, 1H), 3.18 (dd, J1=3.95, J2=12.63, 1H), 3.07 (d of t, J1=12.90, J2=4.78, 1H), 2.74 (m, 1H), 2.63 (dd, J1=8.28, J2=12.58, 1H), 2.10 (m, 1H), 1.57 (m, 1H).

Preparation of Compound 135N:

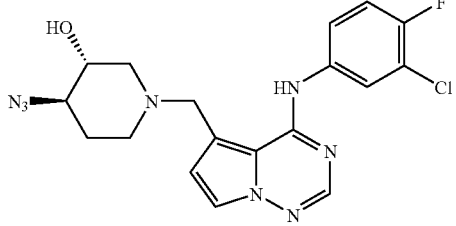

Compound 135N was prepared in a similar way as Compound 1F (using Method Two) in Example 1 starting from Compound 135M and 1E of Example 1. Compound 135N is a solid and has an analytical HPLC retention time=2.099 min. (Chromolith SpeedROD column 4.6×50 mm, 10–90% aqueous methanol containing 0.1% TFA over 4 minutes, 4 mL/min, monitoring at 254 nm) and a LC/MS M$^+$+1=417$^+$.

To a solution of above prepared Compound 135N (0.5 mmol) in a mixture of THF (5 mL) and water (0.05 mL) was added triphenylphosphine (262 mg, 1.0 mmol). The reaction mixture was heated to reflux for 8 hrs. After cooling to room temperature, the solvent was evaporated under reduced pressure and the residue was directly purified by flash chromatography (CH$_2$Cl$_2$—MeOH—NH$_4$OH: 95:5:0.5) on silica gel to give 166 mg of Compound 135 as a solid.

EXAMPLE 136

3-Amino-1-[[4-[(3-chloro-4-fluorophenyl)amino]pyrrolo[2,1-f][1,2,4]triazin-5-yl]methyl]-(3R,4R)-rel-4-piperidinol

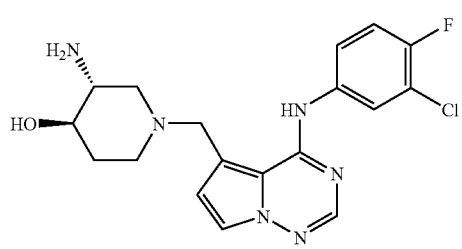

Compound 136 was prepared in a similar manner as Example 1 using Compound 135H and 1E. Compound 136 is a solid, with an analytical HPLC retention time=1.953 min. (Chromolith SpeedROD column 4.6×50 mm, 10–90% aqueous methanol containing 0.1% TFA over 4 minutes, 4 mL/min, monitoring at 254 nm) and a LC/MS M$^+$+1=391$^+$.

EXAMPLE 137

4-Amino-1-[[4-[(3-chloro-4-fluorophenyl)amino]pyrrolo[2,1-f][1,2,4]triazin-5-yl]methyl]-(3R,4R)-(+)-rel-3-piperidinol

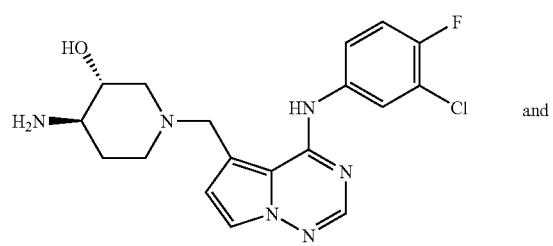

EXAMPLE 138

4-Amino-1-[[4-[(3-chloro-4-fluorophenyl)amino]pyrrolo[2,1-f][1,2,4]triazin-5-yl]methyl]-(3R,4R)-(−)-rel-3-piperidinol

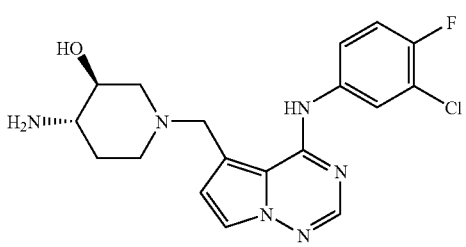

The racemic Compound 135 was resolved using a normal phase chiral preparative HPLC (Chiralpak AD) using hexane-isopropyl alcohol-diethylamine (80:20:0.05) as mobil phase. Compound 137 (Eanatiomer A) and Compound 138 (Enantiomer B) were obtained as single enantiomers with >99% ee.

EXAMPLE 139

N-(3-Chloro-4-fluorophenyl)-5-[[4-[(2,2-dimethyl-propyl)amino]-1-piperidinyl]methyl]pyrrolo[2,1-f][1,2,4]triazin-4-amine

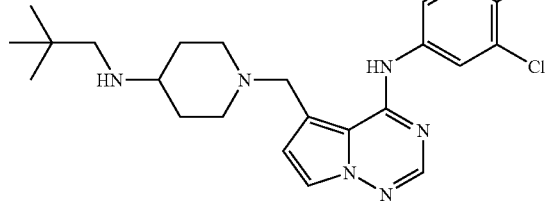

To a solution of the compound of Example 1 (19 mg, 0.05 mmol) in CH$_2$Cl$_2$ (1 mL) was added glacial acidic acid (0.05 mL), followed by 3,3-dimethylbutyraldehyde (0.008 mL, 0.073 mmol) and sodium triacetoxyborohydride (25 mg, 0.12 mol). The mixture was stirred at room temperature for 30 hrs. The reaction mixture was diluted with CH$_2$Cl$_2$, washed with water, sat'd NaHCO$_3$, brine and dried over anhydrous Na$_2$SO$_4$. Concentration in vacuo followed by flash chromatography (CH$_2$Cl$_2$—MeOH—NH$_4$OH: 98:2:0.2 to 98:5:0.5) on silica gel gave Compound 139 as an oil. Analytical HPLC retention time=1.976 min. (Chromolith SpeedROD column 4.6×50 mm, 10–90% aqueous methanol containing 0.1% TFA over 4 minutes, 4 mL/min, monitoring at 254 nm) and a LC/MS M$^+$+1=445$^+$.

EXAMPLE 140

N-(3-Chloro-4-fluorophenyl)-5-[[4-(propylamino)-1-piperidinyl]methyl]-pyrrolo[2,1-f][1,2,4]triazin-4-amine

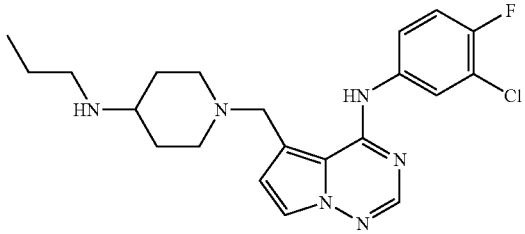

Compound 140 was prepared in a similar way as Compound 139 from Compound 1. Compound 140 is a solid and has an analytical HPLC retention time=1.689 min. (Chromolith SpeedROD column 4.6×50 mm, 10–90% aqueous methanol containing 0.1% TFA over 4 minutes, 4 mL/min, monitoring at 254 nm) and a LC/MS M$^+$+1=417$^+$.

EXAMPLE 141

1-[[4-[(3-Chloro-4-fluorophenyl)amino]pyrrolo[2,1-f][1,2,4]triazin-5-yl]methyl]-4-piperidinol

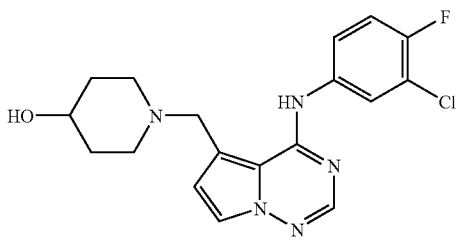

Compound 141 was prepared in a similar way as Compound 1 from 1E of Example 1. Compound 141 is a solid and had an analytical HPLC retention time=1.803 min. (Chromolith SpeedROD column 4.6×50 mm, 10–90% aqueous methanol containing 0.1% TFA over 4 minutes, 4 mL/min, monitoring at 254 nm) and a LC/MS M$^+$+1=376$^+$.

EXAMPLE 142 trans-4-[4-(3-Chloro-4-fluoro-phenylamino)-pyrrolo[2,1-f][1,2,4]triazin-5-ylmethyl]-cyclohexanol

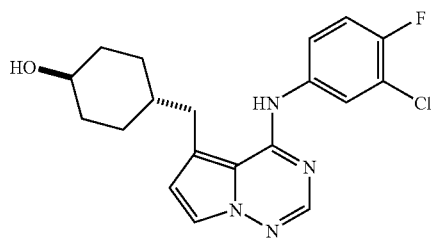

A. Preparation of 4-Chloro-pyrrolo[2,1-f][1,2,4]triazine-5-carbaldehyde

A solution of 4-chloro-5-methyl-pyrrolo[2,1-f][1,2,4]triazine (1.68 g, 10 m mole) in CCl$_4$ was sparged with N$_2$ for 20 min and then NBS (3.74 g, 21 mmole) followed by benzoyl peroxide (242 mg, 1 mmole) were added. The reaction mixture was put into a 100° C. oil bath and refluxed for 3 h. After cooling to RT, this was filtered and the solvent removed. The residue was suspended in CH$_3$OH (100 ml) and solid NaHCO$_3$ (5 g) was added. The reaction mixture was stirred vigorously for 1 h, filtered, and the solvent removed. The residue oil was resuspended in DCM, filtered, and concentrated to afford the crude dimethyl acetal which was treated with DCM (20 ml)/H$_2$O (20 ml)/TFA (1 ml). After stirring vigorously for 1.5 hours, this was neutralized with aqueous saturated NaHCO$_3$ and extracted with DCM. The combined extracts were dried (Na$_2$SO$_4$), concentrated and chromatographed (3×15 cm silica gel column eluted with DCM) to afford the title compound (1.02 g, 56%) as a solid. MS: 182 (M+H)$^+$; HPLC Ret Time: 0.79 min (Xterra 3.0×50 mm S7 column, 2 min gradient, 5 mL/min);

B. Preparation of [4-(tert-Butyl-dimethyl-silanyloxy)-cyclohexyl]-(4-chloro-pyrrolo[2,1-f][1,2,4]triazin-5-yl)-methanol

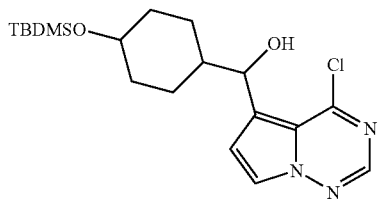

A solution of trans-4-tertbutyldimethylsilyoxy-cyclohexylmagnesium bromide (Bioorg. and Med. Chem., 1996, 6, 201) in THF (4 equiv) was added slowly to an ice-cooled solution of 4-chloro-pyrrolo[2,1-f][1,2,4]triazine-5-carbaldehyde (1.05 g, 5.8 mmole) in THF (15 mL). After 1 h, a saturated aqueous solution of NH$_4$Cl (15 mL) was added and the aqueous layer was extracted with EtOAc/hexane (1:1) (50 mL×2). The combined organic extracts were dried over Na$_2$SO$_4$ and concentrated in vacuo. The crude material was purified via radial chromatography (4 mm silica gel plate, gradient elution with 0 to 15% EtOAc in DCM) to afford the title compound: 189 mg of cis-isomer, 496 mg of tran-isomer and 415 mg of mixture (total yield 48%, the ratio of cis:trans is about 1:4). cis-isomer: MS: 396 (M+H)$^+$; HPLC Ret Time: 2.10 min (Xterra 3.0×50 mm S7 column, 2 min gradient, 5 mL/min); trans-isomer: MS: 396 (M+H)+; HPLC Ret Time 2.08 min (Xterra 3.0×50 mm S7 column, 2 min gradient, 5 mL/min).

C. Preparation of [4-(3-Chloro-4-fluoro-phenylamino)-pyrrolo[2,1-f][1,2,4]triazin-5-yl]-[4-(1-methyl-1-trimethylsilanyl-ethoxy)-cyclohexyl]-methanol

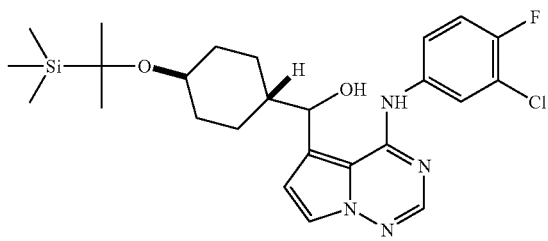

A mixture of trans-[4-(tert-butyldimethylsilanyloxy)-cyclohexyl]-(4-chloro-pyrrolo[2,1-f][1,2,4]triazin-5-yl)-methanol (840 mg, 2.13 mmole), 3-chloro-4-fluoro-phenylamine (309 mg, 2.13 mmole) and NaHCO$_3$ (536 mg, 6.39 mmole) in CH$_3$CN (10 mL) was heated at 70° C. overnight. The solvent was removed and the residue was suspended in DCM, washed with water, and dried over Na$_2$SO$_4$. Removal of the solvent followed by radial chromatography (4 mm silica gel plate, gradient elution with 0 to 2% NH$_3$ in MeOH (2N) in DCM) afforded the title compound (612 mg, 57%) as a solid: MS: 506 (M+H)$^+$; HPLC Ret Time: 2.29 min (Xterra 3.0×50 mm S7 column, 2 min gradient, 5 mL/min).

D. Preparation of trans-4-[4-(3-Chloro-4-fluoro-phenylamino)-pyrrolo[2,1-f][1,2,4]triazin-5-ylmethyl]-cyclohexanol A mixture of [4-(3-chloro-4-fluoro-phenylamino)-pyrrolo [2,1-f][1,2,4]triazin-5-yl]-[4-(1-methyl-1-trimethylsilanyl-ethoxy)-cyclohexyl]-methanol (448 mg, 0.887 mmole) triethylsilane (1.03 g, 8.87 mmole) in TFA (8 mL) under N$_2$ in a pressure flask was heated at 75° C. overnight. The solvents were removed and the residue was dissolved in CH$_3$OH (10 ml) and solid Na$_2$CO$_3$ (2.0 g) was added. After stirring vigorously for 1 h, the solvent was removed and the residue was partitioned between DCM (200 ml) and H$_2$O (50 ml). The organic phase was separated, dried over Na$_2$SO$_4$, and the solvent was removed. Purification via radial chromatography (2 mm silica gel plate, gradient elution with 0 to 4% NH$_3$ in MeOH (2N) in DCM) afforded the title compound (209 mg, 63%) as a solid: MS: 375 (M+H)$^+$; HPLC Ret Time: 1.49 min (Xterra 3.0×50 mm S7 column, 2 min gradient, 5 mL/min).

EXAMPLE 143 cis-4-[4-(3-Chloro-4-fluoro-phenylamino)-pyrrolo[2,1-f][1,2,4]triazin-5-ylmethyl]-cyclohexanol

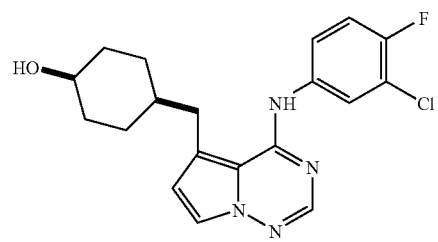

Similarly, the title compound was prepared from cis-[4-(tert-butyldimethylsilanyloxy)-cyclohexyl]-(4-chloro-pyrrolo[2,1-f][1,2,4]triazin-5-yl)-methanol: 375 (M+H)$^+$; HPLC Ret Time: 1.56 min (Xterra 3.0×50 mm S7 column, 2 min gradient, 5 mL/min).

EXAMPLE 144

4-[4-(3-Chloro-4-fluoro-phenylamino)-pyrrolo[2,1-f][1,2,4]triazin-5-ylmethyl]-cyclohexanone

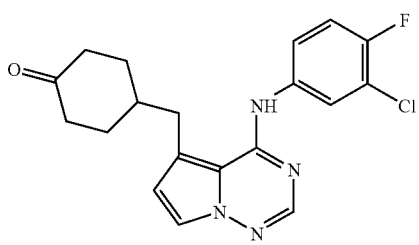

A solution of cis[4-(tert-butyldimethylsilanyloxy)-cyclohexyl]-(4-chloro-pyrrolo[2,1-f][1,2,4]triazin-5-yl)-methanol: (53 mg, 0.14 m mole), 4-methylmorpholine N-oxide (25 mg, 0.21 mmole), TPAP (5 mg, 0.1 eq) and powered 4A molecular sieves (100 mg) in DCM (3 ml) under N$_2$ was stirred at RT. After 5 h, this was filtered and the solvent removed. Radial chromatography (1 mm silica gel plate, gradient elution with 0 to 5% NH$_3$ in MeOH (2 N) in DCM ) afforded the title compound (25 mg, 47%) as a solid: MS: 373 (M+H)$^+$; HPLC Ret Time: 1.50 min (Xterra 3.0×50 mm S7 column, 2 min gradient, 5 mL/min).

EXAMPLE 145

4-Amino-1-[4-(3-chloro-4-fluoro-phenylamino)-pyrrolo[2,1-f][1,2,4]triazin-5-ylmethyl]-cyclohexanol

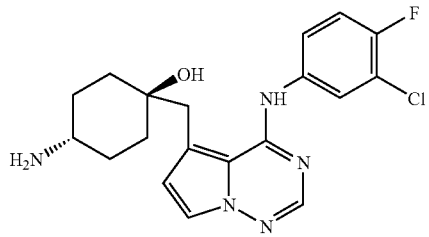

To a solution of 4-[4-(3-chloro-4-fluoro-phenylamino)-pyrrolo[2,1-f][1,2,4]triazin-5-ylmethyl]-4-hydroxy-cyclohexanone (24 mg, 0.06 mmole) in dry MeOH (0.5 mL) was added powdered 3A molecular sieves (24 mg), (10 eq) NH$_4$OAc (48 mg, 0.06 mmole), and NaCNBH$_3$ (4 mg, 0.06 mmole); the reaction stirred under nitrogen for 12 hr. The reaction mixture was filtered and a 15% NaOH solution was added. After 10 min, the mixture was diluted with DCM (50 mL) and washed with water. The organic phase was dried (Na$_2$SO$_4$) and the solvent was removed. The material was purified and separated by preparative HPLC to afford the title compound (3.5 mg, 15%) and the cis isomer (7.9 mg, 32%). The title compound: MS: 390 (M+H)$^+$; HPLC Ret Time: 2.070 min (XTERRA 4.6×50 mm S5 column, 3 min gradient, 4 mL/min). The cis isomer: MS: 390 (M+H)$^+$; HPLC Ret Time: 2.190 min (XTERRA 4.6×50 mm S5 column, 3 min gradient, 4 mL/min).

EXAMPLE 146

(3R,4R)-4-amino-1-[[4-[(3-methoxyphenyl)amino]pyrrolo[2,1-f][1,2,4]triazin-5-yl]methyl]piperidin-3-ol

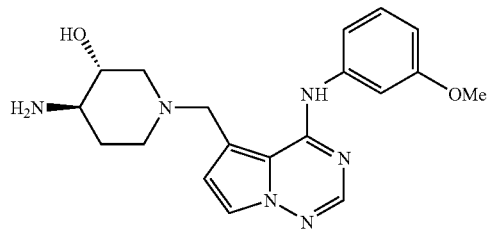

Preparation of Compounds 146A and 146B:

(3R,4R)-4-Azido-3-hydroxy-piperidine-1-carboxylic acid tert-butyl ester (146A):

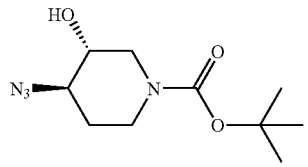

(3S,4S)-4-Azido-3-hydroxy-piperidine-1-carboxylic acid tert-butyl ester (146B):

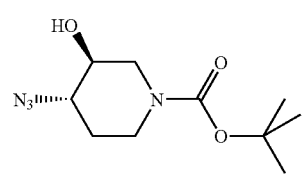

Compounds 146A and 146B were obtained from Compound 135L by optical resolution using a normal phase chiral preparative HPLC (Chiralpak AD) using MeOH-EtOH (50:50) as mobil phase. Compound 146A (first eluent) and Compound 146B (second eluent) were obtained as single enantiomers with >99% ee. The absolute stereochemistry of Compound 146A (3R, 4R) was determined by a single X-ray crystallographic analysis.

Preparation of Compound 146C:

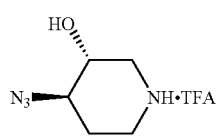

To a solution of Compound 146A (1.76 g, 7.26 mmol) in dry CH$_2$Cl$_2$ (15 mL) cooled at 0° C., was added trifluoroacetic acid (10 mL). The reaction mixture was stirred at 0° C. for 15 min, then warmed to room temperature and stirred for 3 hrs. The solvent and TFA were removed under reduced pressure and the residue was azeotropically evaporated several times with CH$_2$Cl$_2$ to give Compound 146C as a TFA salt.

Preparation of Compound 146D:

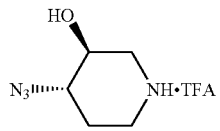

Compound 146D was prepared, as a TFA salt, in a similar manner as Compound 146C using Compound 146B.

Preparation of Compound 146E:

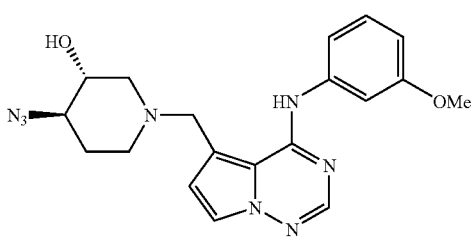

Compound 146E was prepared in a similar way as Example 105 (using Method One) replacing Compound 146C for piperidin-4-yl-carbamic acid tert-butyl ester. Compound 146E is a solid and has an analytical HPLC retention time=2.019 min. (Chromolith SpeedROD column 4.6×50 mm, 10–90% aqueous methanol containing 0.1% TFA over 4 minutes, 4 mL/min, monitoring at 254 nm) and a LC/MS $M^++1=395^+$.

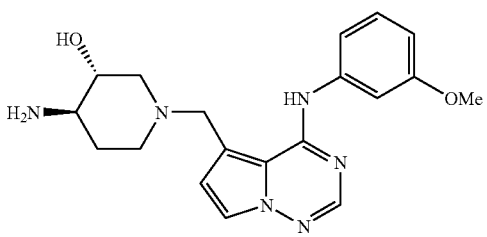

Compound 146 was prepared from Compound 146E in a similar way as Compound 135. Compound 146 is a solid, with an analytical HPLC retention time=1.213 min (Chromolith SpeedROD column 4.6×50 mm, 10–90% aqueous methanol containing 0.1% TFA over 4 minutes, 4 mL/min, monitoring at 254 nm) and a LC/MS $M^++1=369^+$. The enantiomeric excess (ee) of Compound 146 is >99% (Chiralpak AD, 250×4.6 mm 10 micron, EtOH-MeOH-Et2NH: 50:50:0.1).

Alternate preparation of Compuond 146

Preparation of Compound 146F:

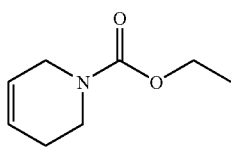

To a solution of 1-methyl-1,2,3,6-tetrahydropiperidine HCl salt (227 g) in 570 mL of water was added solid $K_2CO_3$ (235 g) and the mixture was stirred at room temperature for 30 min. The mixture was extracted with toluene (500 mL×3) and combined extracts were dried over anhydrous $MgSO_4$. Filtration to remove $MgSO_4$ and the filtrate was placed in a 3-L three-necked RB flask. $K_2CO_3$ (22.7 g) was added to the filtrate and the mixture was heated to gentle reflux (bath temperature 110° C.). Ethyl chloroformate (318 mL) was added slowly over 2.5 hrs via an additional funnel (the reaction is extremely exothermic so slow addition with magnetic stirring is highly recommended). Upon completion of addition, the mixture was refluxed for an additional 2.0 hrs and cooled to room temperature. The reaction mixture was washed with water, brine and dried over anhydrous $MgSO_4$. Filtration and concentration in vacuo afforded 188.6 g (72%) of Compound 146F as an oil. $^1$H-NMR (400 MHz, $CDCl_3$):

Preparation of Compound 146G (Racemic):

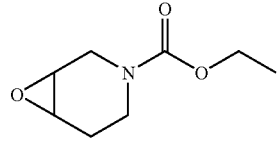

To a solution of Compound 146F (178.2 g, 1.15 mol) in 2 L of dry $CH_2Cl_2$ at 0° C. was added solid m-CPBA (386 g, 1.72 mol, 77% max) in small portions. The reaction mixture was stirred for 1.0 hr at 0° C. and then overnight at room temperature. The precipitate was removed by filtration and the filtration cake was rinsed with $CH_2Cl_2$. The combined filtrate and washes were washed with 20% $Na_2S_2O_3$ (3 L×3), saturated $NaHCO_3$ (3 L×3) and dried over anhydrous $Na_2SO_4$. Filtration followed by concentration in vacuo afforded 170 g of Compound 146G as an oil. This material was used directly in the next reaction step without further purification.

Preparation of Compound 146H (Chiral):

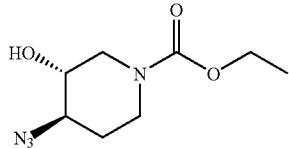

The mixture of Compound 146G (140 g, 0.818 mol), $NaN_3$ (68.9 g, 1.06 mol) and $NH_4Cl$ (56.7 g, 1.06 mol) in ethanol (600 mL) and water (150 mL) was heated at 70° C. overnight. Upon cooling to room temperature, the solid was removed by filtration and rinsed with ethanol. The combined filtrates were concentrated in vacuo to small volume (ca. 80 mL), then diluted with water (500 mL) and extracted with EtOAc (500 mL×4). The combined extracts were dried over anhydrous $Na_2SO_4$. Filtration followed by concentration in vacuo and purification by flash chromatography (hexane-EtOAc 7:3 to 6:4) on silica gel afforded Compound 146G in following fractions: 80.7 g of first fraction (AP: >98%), 22.7 g of second fraction (AP: 92–95%) and 15.8 g of third fraction (AP: <60%) as an oil. This material was used directly in next step reaction without further purification. The first and second fractions were combined and subjected to optical resolution using chiral preparatory HPLC with following conditions: Chiralpak AD column, eluted with MeOH-EtOH (1:1). The first eluted peak (Rt=5.605 min) was collected to give 47.52 g of Compound 146H, with >99% ee.

Preparation of Compound 146I (Chiral):

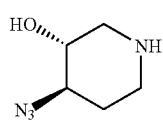

To a solution of Compound 146H (36.42 g, 0.17 mol) in 480 mL of EtOH was added a solution of KOH (112 g, 1.7 mol, 85%) in 240 mL of water. The mixture was heated to reflux for 9.0 hrs and the reaction progress was monitored by TLC. Upon cooling to room temperature, the mixture was concentrated in vacuo to give a paste. Solid NaCl was added and the mixture was extracted with EtOAc (500 mL×3). The combined organic layers were dried over anhydrous $Na_2SO_4$. Filtration followed by removal of solvent under reduced pressure afforded 23 g (77%) of crude Compound 146I as a solid. Trituration with ether (250 mL) gave 18.53 g of Compound 146I as a solid (AP: 99%). The mother liquid was concentrated in vacuo, solid NaCl was added and further extracted with more EtOAc (250 mL×4) to provide an additional 4.2 g of crude Compound 146I (AP: <85%).

Compound 146 was prepared from Compound 146I following the procedure used for the preparation of Compound 146E.

EXAMPLE 147

(3S,4S)-4-amino-1-[[4-[(3-methoxyphenyl)amino] pyrrolo[2,1-f][1,2,4]triazin-5-yl]methyl]3-piperidin-3-ol

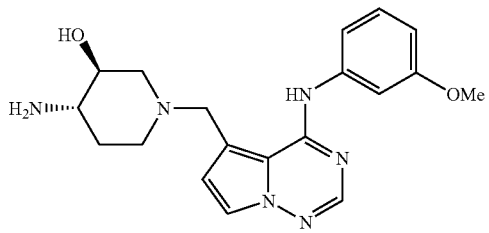

Preparation of Compound 147A:

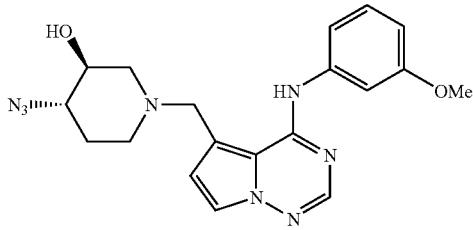

\Compound 147A was prepared in a similar way as Example 105 (using Method One) replacing Compound 130D for piperidin-4-yl-carbamic acid tert-butyl ester. Compound 147A is a solid and had an analytical HPLC retention time=? min. (Chromolith SpeedROD column 4.6×50 mm, 10–90% aqueous methanol containing 0.1% TFA over 4 minutes, 4 mL/min, monitoring at 254 nm) and a LC/MS $M^++1=395^+$.

Compound 147 was prepared from Compound 147A in a similar way as Compound 135. Compound 147 is a solid, with an analytical HPLC retention time=1.213 min (Chromolith SpeedROD column 4.6×50 mm, 10–90% aqueous methanol containing 0.1% TFA over 4 minutes, 4 mL/min, monitoring at 254 nm) and a LC/MS $M^++1=369^+$. The enantiomeric excess (ee) of Compound 147 is >99% (Chiralpak AD, 250×4.6 mm 10 micron, EtOH-MeOH-Et2NH: 50:50:0.1).

EXAMPLE 148

(3R,4R)-4-amino-1-[[4-[(3-methoxy-4-fluorophenyl) amino]pyrrolo[2,1-f][1,2,4]triazin-5-yl]methyl]piperidin-3-ol

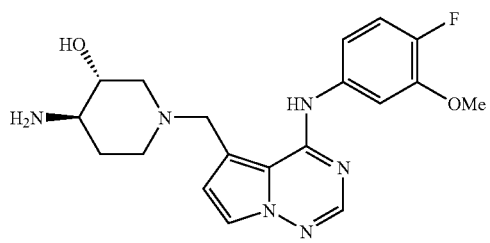

Compound 148 was prepared from Compound 146C in a similar way as Compound 135. Compound 148 is a solid, with an analytical HPLC retention time=1.187 min (Chromolith SpeedROD column 4.6×50 mm, 10–90% aqueous methanol containing 0.1% TFA over 4 minutes, 4 mL/min, monitoring at 254 nm) and a LC/MS $M^++1=387^+$. The enantiomeric excess (ee) of Compound 148 is >99% (Chiralpak AD, 250×4.6 mm 10 micron, EtOH-MeOH-Et2NH: 50:50:0.1).

EXAMPLE 149

(3S,4S)-4-amino-1-[[4-[(3-methoxy-4-fluorophenyl) amino]pyrrolo[2,1-f][1,2,4]triazin-5-yl]methyl]-piperidin-3-ol

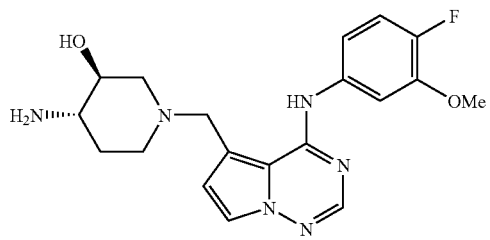

Compound 149 was prepared from Compound 146D in a similar way as Compound 135. Compound 149 is a solid, with an analytical HPLC retention time=1.187 min (Chromolith SpeedROD column 4.6×50 mm, 10–90% aqueous methanol containing 0.1% TFA over 4 minutes, 4 mL/min, monitoring at 254 nm) and a LC/MS $M^++1=387^+$. The enantiomeric excess (ee) of Compound 149 is >99% (Chiralpak AD, 250×4.6 mm 10 micron, EtOH-MeOH-Et2NH: 50:50:0.1).

EXAMPLES 150–200

Compounds 150–200 (with HPLC note (b)) were similarly prepared from 146I as Compound 146.

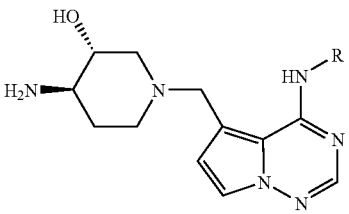

| Ex. | R | Compound Name | [M + H] | HPLC Ret Time (min) |
|---|---|---|---|---|
| 150 | 3-Cl-phenyl | (3R,4R)-4-amino-1-({4-[(3-chlorophenyl)amino]pyrrolo[2,1-f][1,2,4]triazin-5-yl}methyl)piperidin-3-ol | 373 | 1.508 |
| 151 | 3-CN-phenyl | 3-[(5-{[(3R,4R)-4-amino-3-hydroxypiperidin-1-yl]methyl}pyrrolo[2,1-f][1,2,4]triazin-4-yl)amino]benzonitrile | 364 | 1.348 |
| 152 | 4-F-3-Me-phenyl | (3R,4R)-4-amino-1-({4-[(4-fluoro-3-methylphenyl)amino]pyrrolo[2,1-f][1,2,4]triazin-5-yl}-methyl)piperidin-3-ol | 371 | 1.542 |
| 153 | 3-OCHF2-phenyl | (3R,4R)-4-amino-1-[(4-{[3-(difluoromethoxy)-phenyl]amino}pyrrolo[2,1-f][1,2,4]triazin-5-yl)-methyl]piperidin-3-ol | 405 | 1.610 |
| 154 | 3-ethynylphenyl | (3R,4R)-4-amino-1-({4-[(3-ethynylphenyl)-amino]pyrrolo[2,1-f]-[1,2,4]-triazin-5-yl}-methyl)piperidin-3-ol | 363 | 1.730 |
| 155 | 2-Cl-5-OMe-phenyl | (3R,4R)-4-amino-1-({4-[(2-chloro-5-methoxyphenyl)amino]pyrrolo[2,1-f][1,2,4]triazin-5-yl}-methyl)piperidin-3-ol | 403 | 1.300 |
| 156 | 4-Cl-3-OMe-phenyl | (3R,4R)-4-amino-1-({4-[(4-chloro-3-methoxyphenyl)amino]pyrrolo[2,1-f][1,2,4]triazin-5-yl}-methyl)piperidin-3-ol | 403 | 1.620 |

-continued

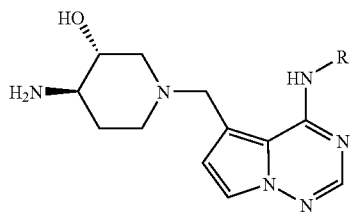

| Ex. | R | Compound Name | [M + H] | HPLC Ret Time (min) |
|---|---|---|---|---|
| 157 | 3-ethoxyphenyl | (3R,4R)-4-amino-1-({4-[(3-ethoxyphenyl)-amino]-pyrrolo[2,1-f]-[1,2,4]triazin-5-yl}-methyl)piperidin-3-ol | 383 | 1.540 |
| 158 | 3-isopropoxyphenyl | (3R,4R)-4-amino-1-({4-[(3-isopropoxyphenyl)-amino]pyrrolo[2,1-f][1,2,4]triazin-5-yl}methyl)-piperidin-3-ol | 397 | 1.820 |
| 159 | 3-(trifluoromethyl)phenyl | (3R,4R)-4-amino-1-[(4-{[3-(trifluoromethyl)-phenyl]amino}pyrrolo[2,1-f][1,2,4]triazin-5-yl)-methyl]piperidin-3-ol | 407 | 1.110[b] |
| 160 | 3-methylphenyl | (3R,4R)-4-amino-1-({4-[(3-methylphenyl)-amino]pyrrolo[2,1-f][1,2,4]triazin-5-yl}-methyl)piperidin-3-ol | 353 | 1.410 |
| 161 | phenyl | (3R,4R)-4-amino-1-[(4-anilinopyrrolo[2,1-f]-[1,2,4]triazin-5-yl)-methyl]piperidin-3-ol | 339 | 0.580[b] |
| 162 | 2-fluoro-5-methoxyphenyl | (3R,4R)-4-amino-1-({4-[(2-fluoro-5-methoxy-phenyl)amino]pyrrolo[2,1-f][1,2,4]triazin-5-yl}-methyl)piperidin-3-ol | 387 | 1.283 |
| 163 | 4-fluorophenyl | (3R,4R)-4-amino-1-({4-[(4-fluorophenyl)-amino]pyrrolo[2,1-f][1,2,4]triazin-5-yl}-methyl)piperidin-3-ol | 357 | 0.820[a] |
| 164 | 2-naphthyl | (3R,4R)-4-amino-1-{[4-(2-naphthylamino)-pyrrolo[2,1-f][1,2,4]-triazin-5-yl]methyl}-piperidin-3-ol | 389 | 1.130[a] |

-continued

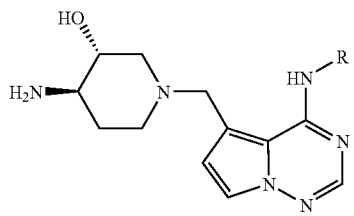

| Ex. | R | Compound Name | [M + H] | HPLC Ret Time (min) |
|---|---|---|---|---|
| 165 | 2-F, 5-Br phenyl | (3R,4R)-4-amino-1-({4-[(5-bromo-2-fluoro-phenyl)amino]pyrrolo[2,1-f][1,2,4]triazin-5-yl}-methyl)piperidin-3-ol | 435 | 2.100 |
| 166 | 3,4-diCl phenyl | (3R,4R)-4-amino-1-({4-[(3,4-dichlorophenyl)-amino]pyrrolo[2,1-f][1,2,4]triazin-5-yl}-methyl)piperidin-3-ol | 407 | 1.260[a] |
| 167 | 4-Br phenyl | (3R,4R)-4-amino-1-({4-[(4-bromophenyl)-amino]pyrrolo[2,1-f][1,2,4]triazin-5-yl}-methyl)piperidin-3-ol | 419 | 1.310[a] |
| 168 | 4-Br, 3-Cl phenyl | (3R,4R)-4-amino-1-({4-[(4-bromo-3-chloro-phenyl)amino]pyrrolo[2,1-f][1,2,4]triazin-5-yl}-methyl)piperidin-3-ol | 453 | 1.670[a] |
| 169 | 3,4-diMe phenyl | (3R,4R)-4-amino-1-({4-[(3,4-dimethylphenyl)-amino]pyrrolo[2,1-f][1,2,4]triazin-5-yl}-methyl)piperidin-3-ol | 367 | 1.200[a] |
| 170 | 3-Cl, 4-Me phenyl | (3R,4R)-4-amino-1-({4-[(3-chloro-4-methyl-phenyl)amino]pyrrolo[2,1-f][1,2,4]triazin-5-yl}-methyl)piperidin-3-ol | 387 | 1.460[a] |
| 171 | 3-acetamido phenyl | N-{3-[(5-({(3R,4R)-4-amino-3-hydroxy-piperidin-1-yl}methyl}-pyrrolo[2,1-f][1,2,4]-triazin-4-yl)amino]-phenyl}acetamide | 396 | 0.900[a] |
| 172 | 4-Me phenyl | (3R,4R)-4-amino-1-({4-[(4-methylphenyl)-amino]pyrrolo[2,1-f][1,2,4]triazin-5-yl}-methyl)piperidin-3-ol | 353 | 1.040[a] |

-continued

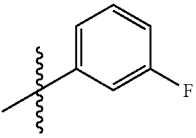

| Ex. | R | Compound Name | [M + H] | HPLC Ret Time (min) |
|---|---|---|---|---|
| 173 | 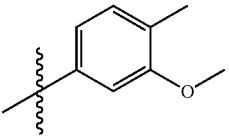 | (3R,4R)-4-amino-1-({4-[(3-fluorophenyl)amino]pyrrolo[2,1-f][1,2,4]triazin-5-yl}methyl)-piperidin-3-ol | 357 | 1.160[a] |
| 174 | 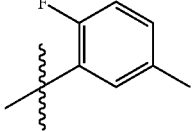 | (3R,4R)-4-amino-1-({4-[(3-methoxy-4-methyl-phenyl)amino]pyrrolo[2,1-f][1,2,4]triazin-5-yl}-methyl)piperidin-3-ol | 383 | 1.160[a] |
| 175 | 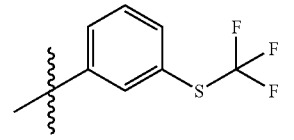 | (3R,4R)-4-amino-1-({4-[(2-fluoro-5-methyl-phenyl)amino]pyrrolo[2,1-f][1,2,4]triazin-5-yl}-methyl)piperidin-3-ol | 371 | 1.120[a] |
| 176 | 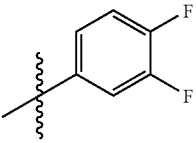 | (3R,4R)-4-amino-1-{[4-({3-[(trifluoromethyl)-thio]phenyl}amino)pyrrolo[2,1-f][1,2,4]triazin-5-yl]methyl}piperidin-3-ol | 439 | 1.770[a] |
| 177 | 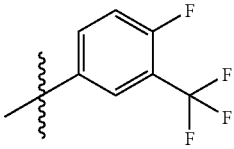 | (3R,4R)-4-amino-1-({4-[(3,4-difluorophenyl)-amino]pyrrolo[2,1-f][1,2,4]triazin-5-yl-methyl)-piperidin-3-ol | 375 | 1.080[a] |
| 178 | 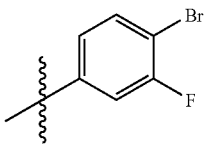 | (3R,4R)-4-amino-1-[(4-{[4-fluoro-3-(trifluoro-methyl)phenyl]amino}pyrrolo[2,1-f][1,2,4]-triazin-5-yl)methyl]piperi-din-3-ol | 425 | 1.230[a] |
| 179 | 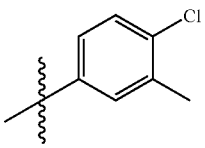 | (3R,4R)-4-amino-1-({4-[(4-bromo-3-fluoro-phenyl)amino]pyrrolo[2,1-f][1,2,4]triazin-5-yl}-methyl)piperidin-3-ol | 435 | 1.480[a] |
| 180 | | (3R,4R)-4-amino-1-({4-[(4-chloro-3-methyl-phenyl)amino]pyrrolo[2,1-f][1,2,4]triazin-5-yl}-methyl)piperidin-3-ol | 387 | 1.430[a] |

-continued

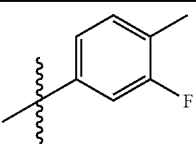

| Ex. | R | Compound Name | [M + H] | HPLC Ret Time (min) |
|---|---|---|---|---|
| 181 | 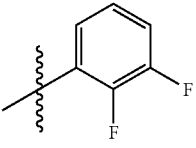 | (3R,4R)-4-amino-1-({4-[(3-fluoro-4-methyl-phenyl)amino]pyrrolo[2,1-f][1,2,4]triazin-5-yl}-methyl)piperidin-3-ol | 371 | 1.240[a] |
| 182 | 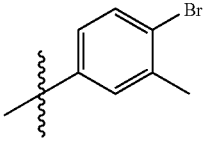 | (3R,4R)-4-amino-1-({4-[(2,3-difluorophenyl)-amino]pyrrolo[2,1-f][1,2,4]triazin-5-yl}-methyl)-piperidin-3-ol | 375 | 0.880[a] |
| 183 | 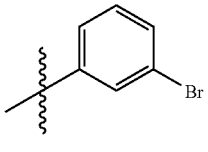 | (3R,4R)-4-amino-1-({4-[(4-bromo-3-methyl-phenyl)amino]pyrrolo[2,1-f][1,2,4]triazin-5-yl}-methyl)piperidin-3-ol | 431 | 1.520[a] |
| 184 | 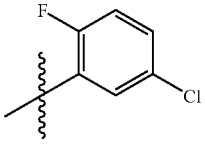 | (3R,4R)-4-amino-1-({4-[(3-bromophenyl)amino]pyrrolo[2,1-f][1,2,4]-triazin-5-yl}methyl)-piperidin-3-ol | 419 | 1.260[a] |
| 185 | 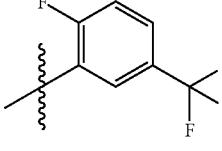 | (3R,4R)-4-amino-1-({4-[(5-chloro-2-fluoro-phenyl)amino]pyrrolo[2,-f][1,2,4]triazin-5-yl}-methyl)piperidin-3-ol | 391 | 1.060[a] |
| 186 | 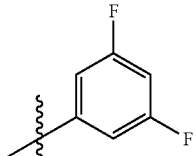 | (3R,4R)-4-amino-1-[(4-{[2-fluoro-5-(trifluoro-methyl)phenyl]amino}pyrrolo[2,1-f][1,2,4]triazin-5-yl)methyl]piperidin-3-ol | 425 | 1.200[a] |
| 187 | 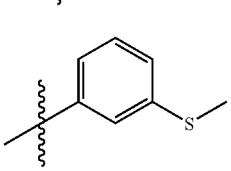 | (3R,4R)-4-amino-1-({4-[(3,5-difluorophenyl)-amino]pyrrolo[2,1-f][1,2,4]triazin-5-yl}-methyl)-piperidin-3-ol | 375 | 1.120[a] |
| 188 |  | (3R,4R)-4-amino-1-[(4-{[3-(methylthio)phenyl]amino}pyrrolo[2,1-f][1,2,4]triazin-5-yl)-methyl]piperidin-3-ol | 385 | 1.200[a] |

-continued

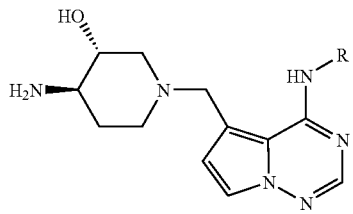

| Ex. | R | Compound Name | [M + H] | HPLC Ret Time (min) |
|---|---|---|---|---|
| 189 | 3-ethylphenyl with CH3 | (3R,4R)-4-amino-1-({4-[(3-ethylphenyl)amino]pyrrolo[2,1-f][1,2,4]triazin-5-yl}methyl)piperidin-3-ol | 367 | 1.870[a] |
| 190 | 4-F, 3-OH phenyl | (3R,4R)-4-amino-1-({4-[(4-fluoro-3-hydroxyphenyl)amino]pyrrolo[2,1-f][1,2,4]triazin-5-yl}-methyl)piperidin-3-ol | 373 | 0.876 |
| 191 | 3-OH phenyl | (3R,4R)-4-amino-1-({4-[(3-hydroxyphenyl)-amino]pyrrolo[2,1-f][1,2,4]triazin-5-yl}methyl)piperidin-3-ol | 355 | 0.915 |
| 192 | 4-OH, 3-OMe phenyl | (3R,4R)-4-amino-1-({4-[(4-hydroxy-3-methoxyphenyl)amino]pyrrolo[2,1-f][1,2,4]triazin-5-yl}-methyl)piperidin-3-ol | 385 | 0.850 |
| 193 | 3-Cl, 5-methyl phenyl | (3R,4R)-4-amino-1-({4-[(3-chloro-5-methylphenyl)amino]pyrrolo[2,1-f][1,2,4]triazin-5-yl}-methyl)piperidin-3-ol | 387 | 1.717 |
| 194 | 3-F, 5-OMe phenyl | (3R,4R)-4-amino-1-({4-[(3-fluoro-5-methoxyphenyl)amino]pyrrolo[2,1-f][1,2,4]triazin-5-yl}-methyl)piperidin-3-ol | 387 | 1.346 |
| 195 | quinolin-6-yl | (3R,4R)-4-amino-1-{[4-(quinolin-6-ylamino)-pyrrolo[2,1-f][1,2,4]triazin-5-yl]methyl}piperidin-3-ol | 390 | 0.870 |

-continued

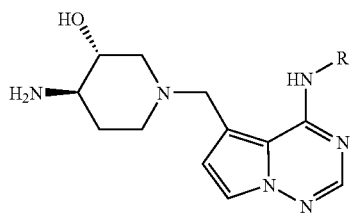

| Ex. | R | Compound Name | [M + H] | HPLC Ret Time (min) |
|---|---|---|---|---|
| 196 | 3-bromo-5-methoxyphenyl | (3R,4R)-4-amino-1-({4-[(3-bromo-5-methoxyphenyl)amino]pyrrolo[2,1-f][1,2,4-triazin-5-yl}-methyl)piperidin-3-ol | 447 | 1.709 |
| 197 | 3-(trifluoromethoxy)phenyl | (3R,4R)-4-amino-1-[(4-{[3-(trifluoromethoxy)-phenyl]amino}pyrrolo[2,1-f][1,2,4]triazin-5-yl)-methyl]piperidin-3-ol | 423 | 1.200[b] |
| 198 | 1,3-benzothiazol-6-yl | (3R,4R)-4-amino-1-{[4-(1,3-benzothiazol-6-yl-amino)pyrrolo[2,1-f][1,2,4]triazin-5-yl]methyl}piperidin-3-ol | 396 | 0.840[a] |
| 199 | 3-(cyanomethyl)phenyl | {3-[(5-{[(3R,4R)-4-amino-3-hydroxypiperi-din-1-yl]methyl}pyrro-lo[2,1-f][1,2,4]triazin-4-yl)amino]phenyl}aceto-nitrile | 378 | 0.790[a] |
| 200 | 3-(1,3-oxazol-5-yl)phenyl | (3R,4R)-4-amino-1-[(4-{[3-(1,3-oxazol-5-yl)-phenyl]amino}pyrrolo[2,1-f][1,2,4]triazin-5-yl)-methyl]piperidin-3-ol | 406 | 0.910[a] |

[a] 2 min gradient time for HPLC.
[b] 2 min gradient time for HPLC (Phenom-prime S5 C18 4.6 × 30 mm column.

EXAMPLE 201 rac-(3S,4R)-4-amino-1-({4-[(3-methoxyphenyl)amino]pyrrolo[2,1-f][1,2,4]triazin-5-yl}methyl)piperidin-3-ol

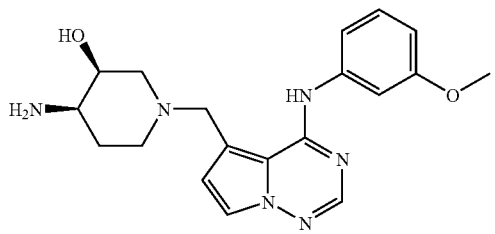

201A. Preparation of (±)-tert-butyl 4-azido-3-oxopiperidine-1-carboxylate

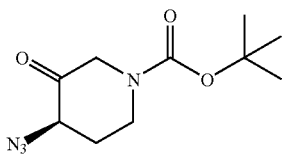

201A

Anhydrous DMSO (0.28 mL, 3.79 mmol) was added to a stirred solution of oxalyl chloride (0.172 mL, 1.96 mmol) in 6 mL of dry $CH_2Cl_2$ at −78° C. under argon. After 10 min, a solution of Compound 135L (396 mg, 1.63 mmol) in 4.5 mL of dry $CH_2Cl_2$ was added dropwise, and the reaction mixture was stirred at −78° C. for 30 min. Triethylamine (1.38 mL, 10.0 mmol) was added and the reaction mixture was allowed to warm to room temperature. 2.0 mL of pH 7.0 buffer solution was added and the mixture was extracted with $CH_2Cl_2$ (×3). The combined organic layers were washed with brine and dried over anhydrous $Na_2SO_4$. Concentration in vacuo afforded crude 201A as an oil which was used immediately in the next reaction step. $^1$H-NMR (400 MHz, $CDCl_3$): 4.30 (d, J=17.84, 1H), 4.05 (m, 1H), 3.90–4.00 (m 1H), 3.45 (m, 1H), 2.85 (m, 1H), 2.33 (m, 1H), 1.86 (m, 1H), 1.47 (s, 9H).

201B. Preparation of (±)-tert-butyl 4-azido-3-hydroxypiperidine-1-carboxylate

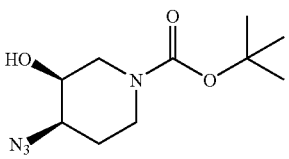

201B

To a solution of Compound 201A prepared above in dry THF (2 mL) cooled at −78° C. was added L-Selectride (1.0 M in THF, 0.98 mL, 0.98 mmol). The mixture was stirred at −78° C. for 2.0 hrs. Saturated $NH_4Cl$ (2 mL) was added and the reaction mixture was allowed to warm to room temperature. The mixture was diluted with water and extracted with EtOAc (3×). The combined organic layers were washed once with brine and dried over anhydrous $Na_2SO_4$. Concentration in vacuo followed by flash chromatography (hexane-EtOAc 4:1) on silica gel gave 44 mg of Compound 201B as an oil. $^1$H-NMR (400 MHz, $CDCl_3$): 3.84 (m, 1H), 3.69 (m, 1H), 3.58 (m, 2H), 3.40 (m, 1H), 3.30 (m, 1H), 1.96 (m, 1H), 1.73 (m, 1H), 1.46 (s, 9H).

201C. Preparation of (±)-4-azidopiperidin-3-ol

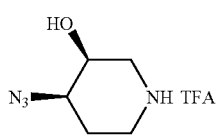

201C

Compound 201B (44 mg, 0.18 mmol) was treated with a mixture of $CH_2Cl_2$ and TFA (1:1, 2 mL) for 30 min. The volatiles were removed under reduced pressure and the residue was azeotropically evaporated with heptane-$CH_2Cl_2$ three times to give a TFA salt of Compound 201C, which was used immediately in the next reaction without step further purification.

Preparation of 201D:

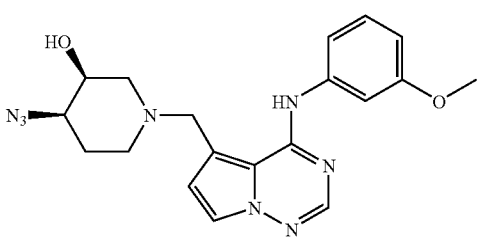

201D

Compounds 201D was prepared as a solid from Compound 201C in a similar way as Compound 146E. It had an analytical HPLC retention time=1.795 min. (Chromolith SpeedROD 4.6×50 mm, 10–90% aqueous methanol over 4 minutes containing 0.1% TFA, 4 ml/min, monitoring at 220 nm) and a LC/MS $M^+$=395.

Compound 201 was prepared from Compound 201D in a similar way as Compound 146. It had an analytical HPLC retention time=1.169 min. (Chromolith SpeedROD 4.6×50 mm, 10–90% aqueous methanol over 4 minutes containing 0.1% TFA, 4 ml/min, monitoring at 220 nm) and a LC/MS $M^+$=369.

EXAMPLE 202A AND 202B (3S,4R)-4-amino-1-({4-[(3-methoxyphenyl)amino]pyrrolo[2,1-f][1,2,4]triazin-5-yl}methyl)piperidin-3-ol (Enantiomer A, Chiral)

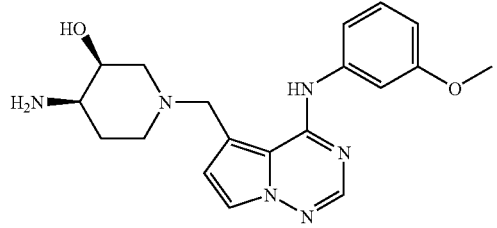
202A (3R,4S)-4-amino-1-({4-[(3-methoxyphenyl)amino]pyrrolo[2,1-f][1,2,4]triazin-5-yl}methyl)piperidin-3-ol (Enantiomer B, Chiral)

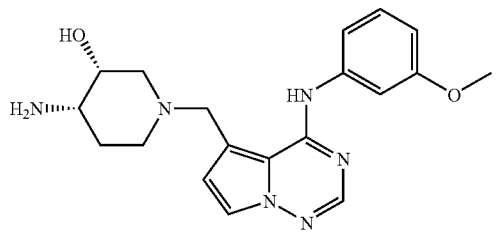
202B

Compound 202A (15 mg) and compound 202B (15 mg) were obtained by optical resolution of Compound 201 (30 mg) using the following method: Chiralpak AD chiral preparatory column eluted with hexane-isopropyl alcohol-diethylamine (50:50:0.1) using gradient of 6.0 ml/min flow rate and detected at 220 nm. The first eluted peak corresponds to Compound 202A (retention time=4.337 min) with ee %≧98%; the second eluted peak corresponds to Compound 202B (retention time=6.050 min) with ee % ≧98%.

EXAMPLE 203

(3S,4R)-4-amino-1-({4-[(3-methylphenyl)amino]pyrrolo[2,1-f][1,2,4]triazin-5-yl}methyl)piperidin-3-ol (Chiral)

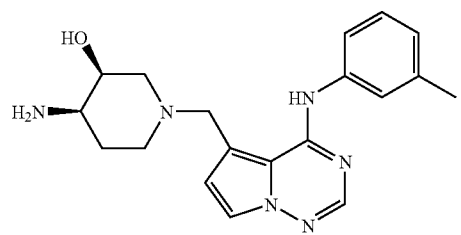
203

Preparation of Compound 203A and 203B (Chiral):

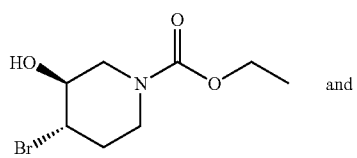
203A

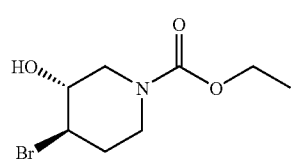
203B

To a solution of Compound 146G (100 g, 0.585 mol) in 2 L of chloroform cooled at −60° C. was added, dropwise via an additional funnel, 196.5 mL of 48% HBr while the internal temperature was kept below −60° C. Upon completion of addition, the reaction mixture was stirred for another 1.0 hr at −60° C. The reaction mixture was warmed to room temperature and washed with water (1 L×2), brine (1 L) and dried over anhydrous MgSO4. Filtration followed by concentration in vacuo afforded 134.2 g (91%) of crude compound (racemic mixture of 203A and 203B) as an oil. $^1$H-NMR (400 MHz, CDCl$_3$): 4.25 (m, 1H), 4.15 (q, J=7.10, 2H), 4.00 (m, 1H), 3.90 (bs, 1H), 3.75 (m, 1H), 2.85–3.15 (m, 2H), 2.32 (m, 1H), 2.00 (m, 1H), 1.28 (t, J=7.10, 3H).

Compounds 203A and 203B were obtained from optical resolution of the above racemic mixture by a normal phase chiral preparative HPLC (Chirlapak AD) using CH$_3$CN as a mobil phase. 54.77 g of Compound 203B (first eluent, Rt=5.861 min) and 53.71 g of Compound 203A (second eluent, Rt=8.719 min) were obtained as single enantiomers with >99% ee. The absolute stereochemistry of Compound 203B (3R,4S) was assigned based on the a single x-ray crystallographic analysis of Compound 203.

Preparation of Compound 203C (Chiral):

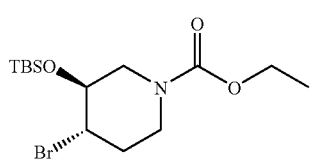
203C

To a solution of Compound 203A (53.7 g, 0.213 mol) in 250 mL of DMF, was added imidazole (21.8 g, 0.32 mol), followed by t-butyldimethylsilyl chloride (38.5 g, 0.258 mol) at 0° C. The reaction mixture was stirred at ambient temperature overnight. Ether (1 L) was added to the reaction mixture, followed by water (1 L) at 0° C. The organic layer was separated. The aqueous layer was extracted with ether (1 L×2) and combined organic layers were washed with 10% LiCl (750 mL×3), dried over anhydrous MgSO$_4$. Filtration followed by concentration in vacuo afforded crude Compound 203C as an oil, which was used immediately without further purification.

Preparation of Compound 203D (Chiral):

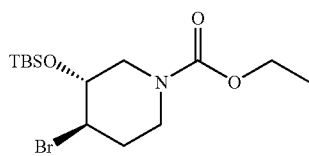

Compound 203D was prepared from Compound 203B in a similar way as Compound 203C.

Preparation of Compound 203E (Chiral):

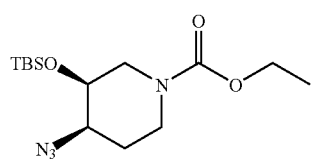

To a solution of Compound 203C (0.213 mol) in 300 mL of DMSO was added $NaN_3$ (15.3 g, 0.234 mol) and the mixture was heated at 85° C. for 12 hrs. Additional $NaN_3$ (15.0 g, 0.230 mol) was added and the reaction mixture was heated overnight. Upon cooling to room temperature, ice water was added to the reaction mixture and extracted with ether (1 L×3). The combined organic layers were washed once with brine (1 L) and dried over anhydrous $MgSO_4$. Filtration followed by concentration in vacuo afforded 69.5 g of crude Compound 203E as an oil, which was used immediately without further purification.

Preparation of Compound 203F (Chiral):

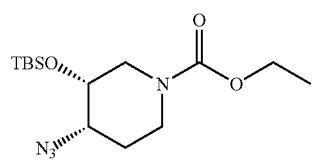

Compound 203F was prepared from Compound 203D in a similar way as Compound 203E.

Preparation of Compound 203G (Chiral):

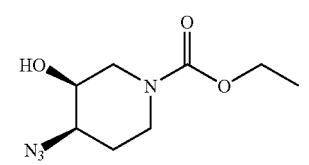

The mixture of Compound 203E (0.213 mol) prepared above and TBAF×$H_2O$ (67 g, 0.255 mol) in 200 mL of THF was stirred at room temperature for 3.0 hrs. Ether (1 L) was added and the mixture was washed with water (1 L). The aqueous phase was extracted with ether (1 L×2). The combined organic layers were washed once with water (1 L) and dried over anhydrous $MgSO_4$. Concentration in vacuo followed by flash chromatography ($CH_2Cl_2$-EtOAc: 4:1) on silica gel afforded 29.8 g of Compound 203G as an oil. Second flash chromatography (hexane-EtOAc: 6.5:3.5) on silica gel gave 20 g (44%) of Compound 203G as an oil. $^1$H-NMR (400 MHz, $CDCl_3$): 4.15 (q, J=7.10, 2H), 3.86 (bs, 1H), 3.70 (bs, 1H), 3.65 (m, 1H), 3.47 (dd, J=3.20, J=13.62, 1H), 3.35 (m, 1H), 2.02 (m, 1H), 1.79 (bs, 1H), 1.28 (t, J=7.10, 3H).

Preparation of Compound 203H (Chiral):

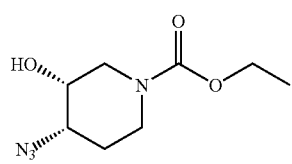

Compound 203H was prepared from Compound 203F in a similar way as Compound 203G.

Preparation of Compound 203I (Chiral):

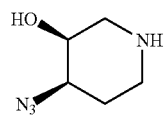

Compound 203I was prepared from Compound 203G in a similar way as Compound 146I. Compound 203I is a solid with ≧99ee %. $^1$H-NMR (400 MHz, $CDCl_3$): 3.80 (m, 1H), 3.44 (m, 1H), 3.04 (m, 2H), 2.72 (m, 1H), 2.69 (m, 1H), 1.90 (m, 1H), 1.75 (m, 1H).

Preparation of Compound 203J (Chiral):

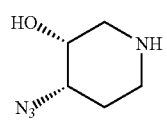

Compound 203J was prepared from Compound 203H in a similar way as Compound 146I. Compound 203J is a solid with >99ee %.

Compound 203 was prepared from Compound 1B, meta-methylaniline and Compound 203I in a similar way as Compound 146. It had an analytical HPLC retention time=1.278 min. (Chromolith SpeedROD 4.6×50 mm column, 10–90% aqueous methanol over 4 minutes containing 0.1% TFA, 4 ml/min, monitoring at 220 nm) and a LC/MS $M^++1=353$.

EXAMPLES 204–211

Compounds 204–211 (with HPLC note (b)) were similarly prepared from Compound 1B, the corresponding anilines and Compound 203I, as used for Compound 146.

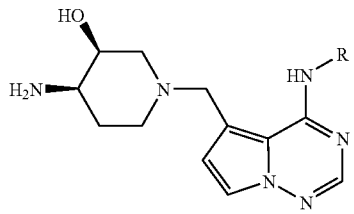

| Ex. | R | Compound Name | [M + H] | HPLC Ret Time (min) |
|---|---|---|---|---|
| 204 | 3-chlorophenyl | (3S,4R)-4-amino-1-({4-[(3-chlorophenyl)amino]pyrrolo[2,1-f][1,2,4]-triazin-5-yl}methyl)-piperidin-3-ol | 373 | 1.356 |
| 205 | 3-cyanophenyl | 3-[(5-{[(3S,4R)-4-amino-3-hydroxypiperidin-1-yl]methyl}pyrrolo[2,1-f][1,2,4]triazin-4-yl)amino]benzonitrile | 364 | 0.948 |
| 206 | 3-chloro-4-fluorophenyl | (3S,4R)-4-amino-1-({4-[(3-chloro-4-fluorophenyl)amino]pyrrolo[2,1-f][1,2,4]triazin-5-yl}-methyl)piperidin-3-ol | 391 | 1.394 |
| 207 | 4-fluoro-3-methoxyphenyl | (3S,4R)-4-amino-1-({4-[(4-fluoro-3-methoxyphenyl)amino]pyrrolo[2,1-f][1,2,4]triazin-5-yl}-methyl)piperidin-3-ol | 387 | 1.092 |
| 208 | 3-(difluoromethoxy)phenyl | (3S,4R)-4-amino-1-[(4-{[3-(difluoromethoxy)-phenyl]amino}pyrrolo[2,1-f][1,2,4]triazin-5-yl)-methyl]piperidin-3-ol | 405 | 1.312 |
| 209 | 3-ethynylphenyl | (3S,4R)-4-amino-1-({4-[(3-ethynylphenyl)amino]pyrrolo[2,1-f][1,2,4]triazin-5-yl}methyl)piperidin-3-ol | 363 | 1.224 |
| 210 | 4-fluoro-3-methylphenyl | (3S,4R)-4-amino-1-({4-[(4-fluoro-3-methylphenyl)amino]pyrrolo[2,1-f][1,2,4]triazin-5-yl}-methyl)piperidin-3-ol | 371 | 1.346 |
| 211 | 2-fluoro-5-methoxyphenyl | (3S,4R)-4-amino-1-({4-[(2-fluoro-5-methoxyphenyl)amino]pyrrolo[2,1-f][1,2,4]triazin-5-yl-methyl)piperidin-3-ol | 387 | 1.182 |

EXAMPLES 212–219

Compounds 212–219 (with HPLC note (b)) were similarly prepared from Compound 1B, the corresponding anilines and Compound 203J, as used for Compound 146.

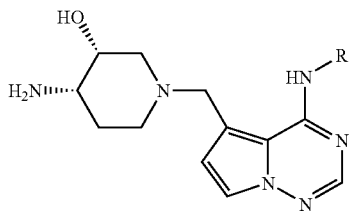

| BMS# | Ex. | R | Compound Name | [M + H] | HPLC Ret Time (min) |
|---|---|---|---|---|---|
| | 212 | 4-F, 3-methyl phenyl | (3R,4S)-4-amino-1-({4-[(4-fluoro-3-methyl-phenyl)amino]pyrrolo[2,1-f][1,2,4]triazin-5-yl}-methyl)piperidin-3-ol | 371 | 1.298 |
| | 213 | 3-ethynyl phenyl | (3R,4S)-4-amino-1-({4-[(3-ethynylphenyl)-amino]pyrrolo[2,1-f][1,2,4]triazin-5-yl}methyl)piperidin-3-ol | 363 | 1.218 |
| | 214 | 3-methyl phenyl | (3R,4S)-4-amino-1-({4-[(3-methylphenyl)-amino]pyrrolo[2,1-f][1,2,4]triazin-5-yl}methyl)piperidin-3-ol | 353 | 1.253 |
| | 215 | 4-F, 3-Cl phenyl | (3R,4S)-4-amino-1-({4-[(3-chloro-4-fluoro-phenyl)amino]pyrrolo[2,1-f][1,2,4]triazin-5-yl}-methyl)piperidin-3-ol | 391 | 1.354 |
| | 216 | 3-Cl phenyl | (3R,4S)-4-amino-1-({4-[(3-chlorophenyl)amino]pyrrolo[2,1-f][1,2,4]-triazin-5-yl}methyl)-piperidin-3-ol | 373 | 1.304 |
| | 217 | 4-F, 3-OMe phenyl | (3R,4S)-4-amino-1-({4-[(4-fluoro-3-methoxy-phenyl)amino]pyrrolo[2,1-f][1,2,4]triazin-5-yl}-methyl)piperidin-3-ol | 387 | 1.086 |
| | 218 | 3-cyano phenyl | 3-[(5-{[(3R,4S)-4-amino-3-hydroxypiperidin-1-yl]methyl}pyrrolo[2,1-f][1,2,4]triazin-4-yl)amino]benzonitrile | 364 | 0.932 |

-continued

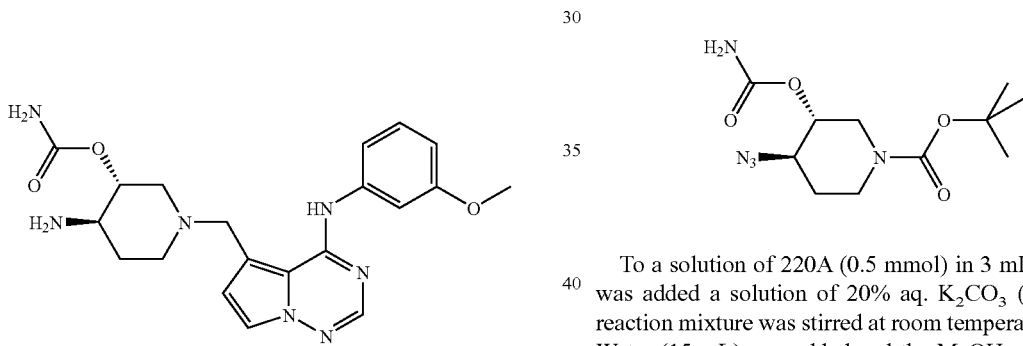

| BMS# | Ex. | R | Compound Name | [M + H] | HPLC Ret Time (min) |
|---|---|---|---|---|---|
| | 219 | 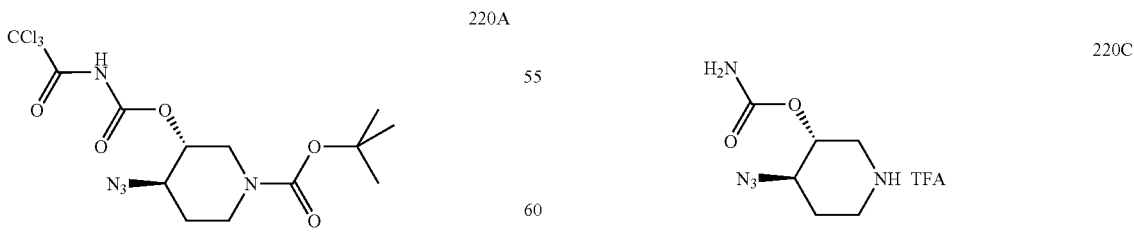 | (3R,4S)-4-amino-1-[(4-{[3-(difluoromethoxy)-phenyl]amino}pyrrolo[2,1-f][1,2,4]triazin-5-yl)-methyl]piperidin-3-ol | 405 | 1.318 |

EXAMPLE 220

(3R,4R)-4-amino-1-({4-[(3-methoxyphenyl)amino]pyrrolo[2,1-f][1,2,4]triazin-5-yl}methyl)piperidin-3-yl carbamate Preparation of Compound 220A (Chiral):

To a solution of Compound 146A (121 mg, 0.5 mmol) in 1 mL of dry $CH_2Cl_2$ cooled at 0° C., was added trichloroacetylisocyanate (0.075 mL, 0.6 mmol). The reaction mixture was stirred at 0° C. for 1.0 hr. MeOH (0.5 mL) was added and the reaction mixture was concentrated in vacuo to give crude Compound 220A as a foam. $^1$H-NMR (400 MHz, $CDCl_3$): 8.35 (bs, 1H), 4.67 (bs, 1H), 3.90 (m, 1H), 3.65 (m, 2H), 3.25 (m, 2H), 2.02 (m, 1H), 1.60 (m, 1H), 1.38 (s, 9H).

Preparation of Compound 220B (Chiral):

To a solution of 220A (0.5 mmol) in 3 mL of dry MeOH was added a solution of 20% aq. $K_2CO_3$ (2 mL) and the reaction mixture was stirred at room temperature for 2.0 hrs. Water (15 mL) was added and the MeOH was removed by rotary evaporation. The mixture was extracted with EtOAc (×2) and dried over anhydrous $Na_2SO_4$. Concentration in vacuo afforded crude 220B as an oil. $^1$H-NMR (400 MHz, $CDCl_3$): 4.70 (bs, 2H), 4.50 (m, 1H), 3.90 (bs, 1H), 3.68 (m, 1H), 3.50 (m, 1H), 3.03 (m, 1H), 1.90 (m, 1H), 1.50 (m, 1H), 1.38 (s, 9H).

Preparation of Compound 220C (Chiral):

A mixture of 220B (0.5 mmol) in 5 mL of dry $CH_2Cl_2$ and 5 mL of TFA was stirred at 0° C. for 1.0 hr. The mixture was concentrated in vacuo, azeotropically evaporated several times with $CH_2Cl_2$-MeOH-hexane and dried under high vacuum to afforded crude 220C as an oil.

Preparation of Compound 220D (Chiral):

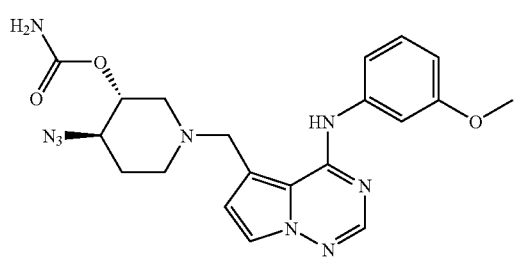

220D

Compound 220D was prepared from Compound 220C in a similar way as Compound 146E. It had an analytical HPLC retention time=1.793 min. (Chromolith SpeedROD 4.6×50 mm, 10–90% aqueous methanol over 4 minutes containing 0.1% TFA, 4 ml/min, monitoring at 220 nm) and a LC/MS M$^+$=438.

Compound 220 was prepared from Compound 220D in a similar way as Compound 146. It had an analytical HPLC retention time=1.310 min. (Chromolith SpeedROD 4.6×50 mm, 10–90% aqueous methanol over 4 minutes containing 0.1% TFA, 4 ml/min, monitoring at 220 nm) and a LC/MS M$^+$=412.

EXAMPLES 221–227

Compounds 221–227 (with HPLC note (b)) were similarly prepared from Compound 1B, corresponding anilines and Compound 220C as Compound 146.

| Ex. | R | Compound Name | [M + H] | HPLC Ret Time (min) |
|---|---|---|---|---|
| 221 | 4-cyano-2-fluorophenyl | (3R,4R)-4-amino-1-({4-[(5-cyano-2-fluorophenyl)amino]pyrrolo[2,1-f][1,2,4]triazin-5-yl}-methyl)piperidin-3-yl carbamate | 425 | 1.545 |
| 222 | 3-ethynylphenyl | (3R,4R)-4-amino-1-({4-[(3-ethynylphenyl)-amino]pyrrolo[2,1-f][1,2,4]triazin-5-yl}-methyl)piperidin-3-yl carbamate | 406 | 1.562 |
| 223 | 3-methylphenyl | (3R,4R)-4-amino-1-({4-[(3-methylphenyl)-amino]pyrrolo[2,1-f][1,2,4]triazin-5-yl}-methyl)piperidin-3-yl carbamate | 396 | 1.381 |
| 224 | 4-fluoro-3-methoxyphenyl | (3R,4R)-4-amino-1-({4-[(4-fluoro-3-methoxy-phenyl)amino]pyrrolo[2,1-f][1,2,4]triazin-5-yl}methyl)piperidin-3-yl carbamate | 430 | 1.236 |
| 225 | 3-chlorophenyl | (3R,4R)-4-amino-1-({4-[(3-chlorophenyl)-amino]pyrrolo[2,1-f][1,2,4]triazin-5-yl}methyl) piperidin-3-ylcarbamate | 416 | 1.782 |

-continued

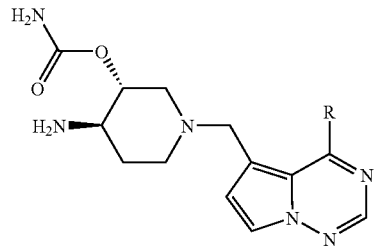

| Ex. | R | Compound Name | [M + H] | HPLC Ret Time (min) |
|---|---|---|---|---|
| 226 | ![F,Cl phenyl] | (3R,4R)-4-amino-1-({4-[(3-chloro-4-fluoro-phenyl)amino]pyrrolo[2,1-f][1,2,4]triazin-5-yl}-methyl)piperidin-3-yl carbamate | 434 | 1.849 |
| 227 | ![cyanophenyl] | (3R,4R)-4-amino-1-({4-[(3-cyanophenyl)-amino]pyrrolo[2,1-f][1,2,4]triazin-5-yl}methyl)piperidin-3-yl carbamate | 407 | 1.486 |

EXAMPLE 229

(3R,4S)-4-amino-1-({4-[(3-methoxyphenyl)amino]pyrrolo[2,1-f][1,2,4]triazin-5-yl}methyl)piperidin-3-yl carbamate

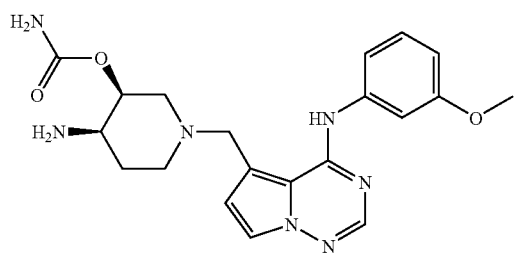

229A. Preparation of Compound 229A (Chiral):

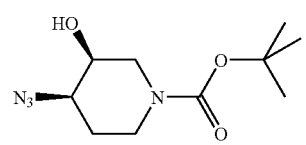

Compound 229A was prepared from Compound 203I in a similar way as Compound 135E, step 2.

229B. Preparation of Compound 229B (Chiral):

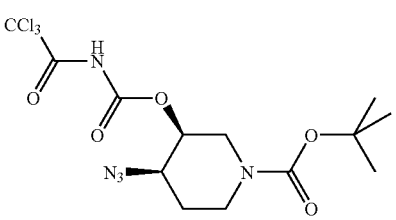

Compound 229B was prepared from Compound 229A in a similar way as Compound 220A.

229C. Preparation of Compound 229C (Chiral):

Compound 229C was prepared from Compound 229B in a similar way as Compound 220B.

229D. Preparation of Compound 229D:

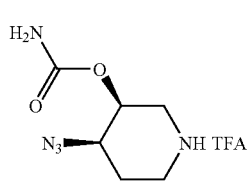

Compound 229D was prepared from Compound 229C in a similar way as Compound 220C.

Compound 229 was prepared from Compound 229D in a similar way as Compound 146. It had an analytical HPLC retention time=1.229 min. (Chromolith SpeedROD 4.6×50 mm, 10–90% aqueous methanol over 4 minutes containing 0.1% TFA, 4 ml/min, monitoring at 220 nm) and a LC/MS M$^+$=412.

EXAMPLES 230–236

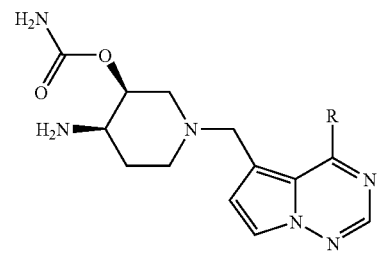

Compounds 230–236 (with HPLC note (b)) were similarly prepared from Compound 1B, corresponding anilines and Compound 229D as Compound 146.

| Ex. | R | Compound Name | [M + H] | HPLC Ret Time (min) |
|---|---|---|---|---|
| 230 | 3-chlorophenyl | (3S,4R)-4-amino-1-({4-[(3-chlorophenyl)amino]pyrrolo[2,1-f][1,2,4]triazin-5-yl}methyl)-piperidin-3-yl carbamate | 416 | 1.506 |
| 231 | 3-chloro-4-fluorophenyl | (3S,4R)-4-amino-1-({4-[(3-chloro-4-fluorophenyl)amino]pyrrolo[2,1-f][1,2,4]triazin-5-yl}-methyl)piperidin-3-yl carbamate | 434 | 1.573 |
| 232 | 3-cyanophenyl | (3S,4R)-4-amino-1-({4-[(3-cyanophenyl)amino]pyrrolo[2,1-f][1,2,4]triazin-5-yl}methyl)-piperidin-3-yl carbamate | 407 | 1.211 |
| 233 | 3-ethynylphenyl | (3S,4R)-4-amino-1-({4-[(3-ethynylphenyl)-amino]pyrrolo[2,1-f][1,2,4]triazin-5-yl}-methyl)piperidin-3-yl carbamate | 406 | 1.396 |
| 234 | 3-methylphenyl | (3S,4R)-4-amino-1-({4-[(3-methylphenyl)-amino]pyrrolo[2,1-f][1,2,4]triazin-5-yl}-methyl)piperidin-3-yl carbamate | 396 | 1.273 |
| 235 | 4-fluoro-3-methoxyphenyl | (3S,4R)-4-amino-1-({4-[(4-fluoro-3-methoxy-phenyl)amino]pyrrolo[2,1-f][1,2,4]triazin-5-yl}-methyl)piperidin-3-yl carbamate | 430 | 1.173 |

| Ex. | R | Compound Name | [M + H] | HPLC Ret Time (min) |
|---|---|---|---|---|
| 236 | ![F-phenyl-CN] | (3S,4R)-4-amino-1-({4-[(5-cyano-2-fluoro-phenyl)amino]pyrrolo[2,1-f][1,2,4]triazin-5-yl}-methyl)piperidin-3-yl carbamate | 425 | 1.230 |

EXAMPLE 237

(3R,4R)-4-amino-1-({4-[(3-methoxyphenyl)amino]pyrrolo[2,1-f][1,2,4]triazin-5-yl}methyl)-3-methylpiperidin-3-ol (Chiral, Enantiomer A)

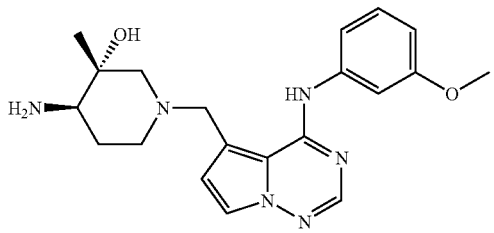

237

Preparation of Compound 237A (Racemic):

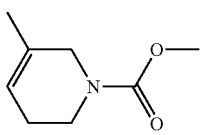

237A

To a solution of N-benzyltetrahydropyridine (100 mmol) in 150 mL of benzene was added solid NaHCO₃ (4.2 g, 49 mmol), followed by methyl chloroformate (9.3 mL, 120 mmol) dropwise via a syringe at room temperature. The reaction mixture was heated to reflux for 3 hrs. After cooling to room temperature, the volatiles were removed by evaporation under reduced pressure and the residue was dissolved in EtOAc (100 mL) and washed with water (20 ml×2), 0.5 M HCl (20 mL) and brine (20 mL), and dried over anhydrous MgSO₄. The reaction mixture was concentrated in vacuo and the residual benzyl chloride was further removed under high vacuum (bp. 42–50° C./2 mmHg, bath temperature: 75–80° C.) to give Compound 237A as a viscous syrup. Flash chromatography (hexane-EtOAc: 9.5:0.5 to 9:1) on silica gel afforded 11.77 g (Yield: 76%) of Compound 237A as an oil. ¹H-NMR (400 MHz, CDCl₃): 5.52 (bs, 1H), 3.78 (m, 2H), 3.70 (s, 3H), 3.46 (m, 2H), 2.08 (m, 2H), 1.68 (s, 3H).

Preparation of Compound 237B (Racemic):

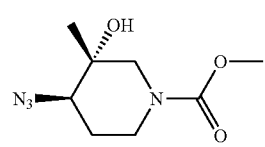

237B

The mixture of Compound 237A (775 mg, 5.0 mmol) and m-CPBA (1.21 g, 7.0 mmol, 77% max) in 10 mL of dry CH₂Cl₂ was stirred overnight at room temperature. The precipitate was removed by filtration and the filtrate was washed by 10% Na₂S₂O₃, sat'd NaHCO₃ and brine, and dried over anhydrous MgSO₄.

Concentration in vacuo afforded crude Compound 237B as an oil. ¹H-NMR (400 MHz, CDCl₃): 3.65–3.75 (m, 2H), 3.68 (s, 3H), 3.60 (m, 1H), 3.33 (m, 2H), 3.12 (m, 1H), 2.07 (m, 1H), 1.92 (m, 1H), 1.35 (s, 3H).

Preparation of Compound 237C (Racemic):

237C

To a solution of Compound 237B (5.0 mmol) in 10 mL of DMF was added NaN₃ (810 mg, 12.4 mmol) in a 2:1 mixture of 10 mL of acetone-H2O and the mixture was heated at 80° C. overnight. After cooling to room temperature, EtOAc was added and the mixture was washed by water, 10% LiCl aq. solution and dried over anhydrous Na₂SO₄. Concentration in vacuo afforded 1.09 g of Compound 237C as an oil. ¹H-NMR (400 MHz, CDCl₃): 3.70 (s, 3H), 3.72 (m, 1H), 3.50 (m, 2H), 3.35 (m, 1H), 3.20 (bs, 1H), 2.03 (m, 1H), 1.63 (m, 1H), 1.20 (s, 3H).

Preparation of Compound 237D (Racemic):

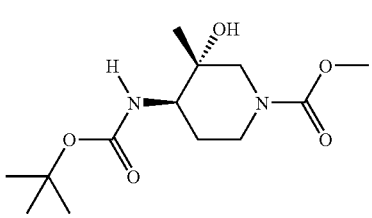

237D

The mixture of Compound 237C (428 mg, 2.0 mmol) and 150 mg of Pd(OH)2 in 10 mL of MeOH was stirred under hydrogen atmosphere (balloon) for 4.0 hrs. The catalyst was removed by filtration and the filtrate was concentrated in vacuo to give a crude residue.

The residue was taken into 5 mL of dry $CH_2Cl_2$ and to this was added $Boc_2O$ (460 mg, 2.10 mmol) and triethylamine (0.334 mL, 2.40 mmol). After stirring at room temperature overnight, the reaction mixture was diluted with was $CH_2Cl_2$ and washed with 10% citric acid, sat'd $NaHCO_3$ and dried ($Na_2SO_4$). Concentration in vacuo followed by flash chromatography (hexane-EtOAc: 7:3 to 1:1) on silica gel gave 330 mg of 237D as an oil. $^1$H-NMR (400 MHz, $CDCl_3$): 4.78 (m, 1H), 3.90–4.40 (m, 3H), 3.70 (s, 3H), 3.60 (m, 1H), 2.70–3.00 (m, 2H), 1.80 (m, 1H), 1.45 (s, 9H), 1.40 (m, 1H), 1.10 (s, 3H).

Preparation of Compound 237E (Racemic):

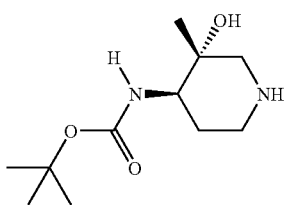

Compound 237E was prepared from Compound 237D in a similar way as Compound 146I.

Preparation of Compound 237F (Racemic):

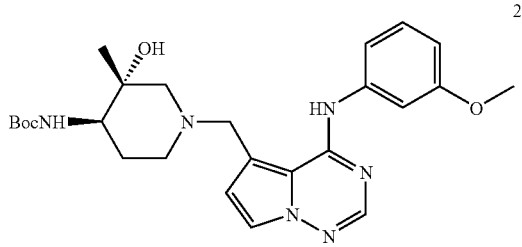

237F

Compound 237F was prepared from Compound 237E in a similar way as Compound 1D.

Preparation of Compound 237G (Racemic):

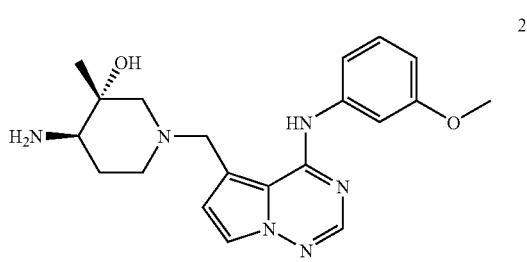

237G

Compound 237G was prepared from Compound 237F in a similar way as Compound 1E. It had an analytical HPLC retention time=1.262 min. (Chromolith SpeedROD 4.6×50 mm, 10–90% aqueous methanol over 4 minutes containing 0.1% TFA, 4 ml/min, monitoring at 220 nm) and a LC/MS $M^++1=383$.

Compound 237 was obtained from 237G by chiral preparative HPLC separation (Chiralpak AD, 250×4.6 mm, 10 micron, eluted by EtOH/MeOH/DEA 50:50:0.1) as the first peak (Rt=5.390 min) with ee % ≧99%. It had an analytical HPLC retention time=1.51 min. (Chromolith SpeedROD 4.6×50 mm column, 10–90% aqueous methanol over 4 minutes containing 0.1% TFA, 4 ml/min, monitoring at 220 nm) and a LC/MS $M^++1=383$.

EXAMPLE 238

(3S,4R)-4-amino-1-({4-[(3-methoxyphenyl)amino]pyrrolo[2,1-f][1,2,4]triazin-5-yl}methyl)-3-methylpiperidin-3-ol (Chiral, Enantiomer B)

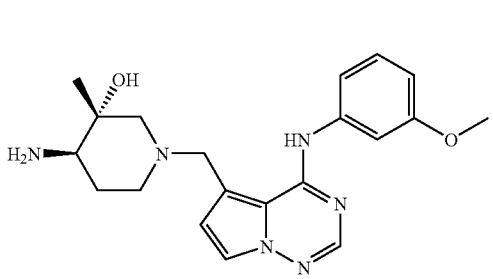

Compound 238 was obtained from 237G by chiral preparative HPLC separation (Chiralpak AD, 250×4.6 mm, 10 micron, eluted by EtOH/MeOH/DEA 50:50:0.1) as the second peak (Rt=8.523 min) with ee % ≧99%. It had an analytical HPLC retention time=1.51 min. (Chromolith SpeedROD 4.6×50 mm column, 10–90% aqueous methanol over 4 minutes containing 0.1% TFA, 4 ml/min, monitoring at 220 nm) and a LC/MS $M^++1=383$.

EXAMPLE 239

(3R,4r,5S)-4-amino-1-({4-[(3-methoxyphenyl)amino]pyrrolo[2,1-f][1,2,4]triazin-5-yl}methyl)piperidine-3,5-diol

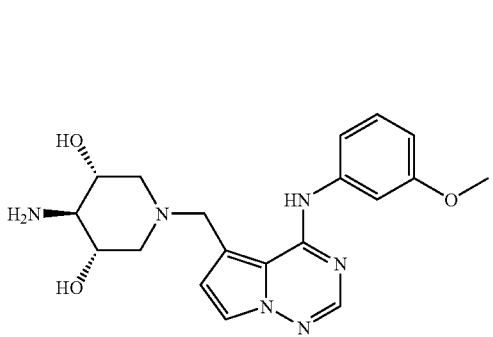

239A. Preparation of (±)-ethyl 3-acetoxy-4-bromopiperidine-1-carboxylate

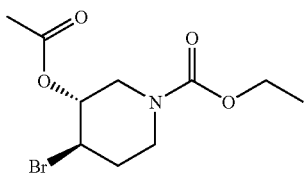

239A

A mixture of Compound 203A/B (racemic mixture) (107 g, 371 mmol) and acetic anhydride (101 mL) in 165 mL of dry pyridine was stirred at room temperature for 2.0 hrs. The solvent was removed under reduced pressure and the residue was diluted with water and made basic with $K_2CO_3$. The mixture was extracted with chloroform (250 mL×3) and the combined extracts were washed with water and dried over anhydrous $MgSO_4$. Concentration in vacuo afforded crude 239A as an oil. $^1$H-NMR (400 MHz, $CDCl_3$): 4.90 (bs, 1H), 4.13 (q, J=7.08, 2H), 4.10 (m, 1H), 3.89 (m, 1H), 3.60 (m, 1H), 3.50 (m, 2H), 2.34 (m, 1H), 2.08 (s 3H), 1.93 (m, 1H), 1.27 (t, J=7.80, 3H).

239B. Preparation of (±)-ethyl 5-acetoxy-5,6-dihydropyridine-1(2H)-carboxylate

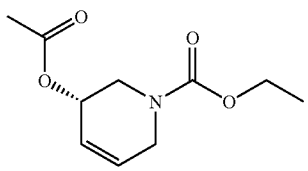

239B

A mixture of Compound 239A (371 mmol) and DBU (92 g, 604 mmol) was heated to 90–110° C. for 30 min. After cooling to room temperature, the mixture was diluted with toluene and stirred for an additional 30 min. The precipitate was removed by filtration and rinsed with toluene. Combined filtrates were washed with 1.0 N HCl, water and dried over anhydrous anhydrous $MgSO_4$. Concentration in vacuo afforded 67.56 g (yield: 85.4%) of 239B as an oil. $^1$H-NMR (400 MHz, $CDCl_3$): 6.00 (bs, 1H), 5.90 (bs, 1H), 5.20 (m, 1H), 4.20 (q, J=7.08, 2H), 4.19 (m, 1H), 3.85 (m, 1H), 3.80 (m, 1H), 3.55 (m, 1H), 2.08 (s, 3H), 1.28 (t, J=7.08, 3H).

239C. Preparation of (±)-ethyl 5-hydroxy-5,6-dihydropyridine-1(2H)-carboxylate

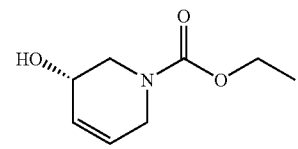

239C

To a solution of Compound 239B (10.5 g, 49.2 mmol) in 30 mL of EtOH was added a solution of 0.2N NaOH in EtOH (65 mL) and the mixture was stirred at 0° C. for 30 min. After warming to room temperature, the reaction mixture was neutralized with glacial acetic acid. Concentration in vacuo afforded 8.5 g of 239C as an oil. $^1$H-NMR (400 MHz, $CDCl_3$): 5.90 (m, 1H), 5.82 (bs, 1H), 4.20 (bs, 1H), 4.18 (q, J=7.08, 2H), 4.04 (m, 1H), 3.85 (m, 1H), 3.55 (m, 2H), 1.28 (t, J=7.08, 3H).

239D. Preparation of (±)-ethyl 5-(tert-butyldimethylsilyloxy)-5,6-dihydropyridine-1(2H)-carboxylate

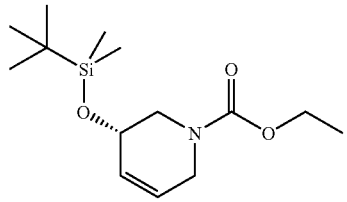

239D

To a solution of Compound 239C (16 g, 93.5 mmol) in 150 mL of dry $CH_2Cl_2$ at 0° C. was added imidazole (9.5 g, 140.0 mmol) and t-butyldimethylsilylchloride (15.5 g, 102.8 mmol) and the mixture was stirred at ambient temperature overnight. The reaction mixture was diluted with ether (500 mL) and water (1 L) at 0° C. The organic phase was separated and washed with 10% LiCl (150 mL×3), dried over anhydrous MgSO4. Concentration in vacuo followed by flash chromatography (hexane-EtOAc: 15:1 to 10:1) afforded 25.2 g (Yield: 94.4%) of 239D as an oil.

239E. Preparation of (±)-ethyl 5-hydroxy-7-oxa-3-aza-bicyclo[4.1.0]heptane-3-carboxylate

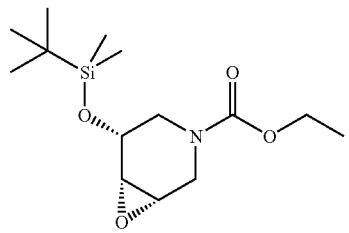

239E

To a solution of Compound 239D (25.2 g, 88.3 mmol) in 250 mL of $CH_2Cl_2$ at 0° C. was added solid m-CPBA (39.6 g, 176.6 mmol, 77% max) in small portions while the internal temperature was kept below 0° C. during the addition. The mixture was stirred at 0° C. for 30 min and then room temperature for 4.0 hrs. More solid m-CPBA (39.6 g, 176.6 mmol, 77% max) was added in small portions and the mixture was stirred at room temperature for three days. The precipitate was removed by filtration and the filtrate was washed with 20% $Na_2S_2O_3$ (500 mL×3), sat'd $NaHCO_3$ (500 mL×3) and brine (250 mL), dried over anhydrous $Na_2SO_4$. Purification by flash chromatography (hexane-EtOAc: 9.5:0.5 to 9:1) on silica gel afforded 4.33 g of 239E (lower Rf) as an oil.

239F. Preparation of (±)-ethyl 5-(tert-butyldimethylsilyloxy)-7-oxa-3-aza-bicyclo[4.1.0]heptane-3-carboxylate

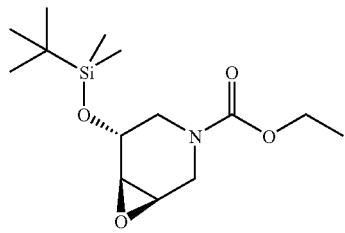

239F

Compound 239F was prepared from 239D in a same reaction as Compound 239E as an oil.

239G. Preparation of (±)-ethyl 5-hydroxy-7-oxa-3-aza-bicyclo[4.1.0]heptane-3-carboxylate

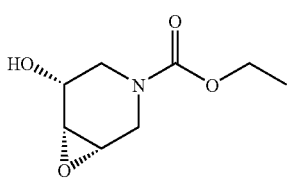

239G

To a solution of Compound 239E (4.33 g, 14.4 mmol) in 10 mL of dry THF was added a solution of TBAF (17.2 mL, 17.2 mmol) in THF. The mixture was stirred overnight at room temperature. Water was added and the reaction mixture was extracted with EtOAc (100 mL×3). The combined organic layers were washed with brine and dried over $Na_2SO_4$. Concentration in vacuo followed by flash chromatography (hexane-EtOAc: 1:1 to 1:2) on silica gel afforded 2.01 g (Yield: 74.5%) of 239G as an oil.

$^1$H-NMR (400 MHz, $CDCl_3$): 4.13 (q, J=7.08, 2H), 4.05 (m, 1H), 3.80 (m, 1H), 3.70 (d, J=10.15, 1H), 3.62 (m, 1H), 3.45 (m, 2H), 3.13 (dd, J=10.15, J=7.63, 1H), 2.40 and 2.25 (partial, 1H), 1.27 (t, J=7.08, 3H).

239H. Preparation of (±)-ethyl 5-hydroxy-7-oxa-3-aza-bicyclo[4.1.0]heptane-3-carboxylate

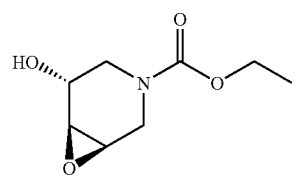

239H

To a solution of Compound 239F (13.6 g, 45.1 mmol) in 10 mL of dry THF was added a solution of TBAF (67.6 mL, 67.6 mmol) in THF. The mixture was stirred overnight at room temperature. Water was added and the reaction mixture was extracted with EtOAc (250 mL×3). The combined organic layers were washed with brine and dried over anhydrous $Na_2SO_4$. Concentration in vacuo followed by flash chromatography (hexane-EtOAc: 1:1 to 1:2) on silica gel afforded 6.03 g (Yield: 75%) of 239H as an oil. $^1$H-NMR (400 MHz, $CDCl_3$): 4.15 (m, 1H), 4.13 (q, J=7.08, 2H), 3.95 (m, 1H), 3.75 (m, 1H), 3.52 (m, 1H), 3.32 (m, 1H), 3.25 (m, 2H), 3.10 and 2.55 (partial, 1H), 1.27 (t, J=7.08, 3H).

239I. Preparation of (±)-ethyl 4-azido-3,5-dihydroxypiperidine-1-carboxylate

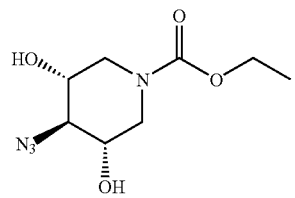

239I

To a solution of Compound 239G (2.0 g, 10.7 mmol) in 2-methoxyethanol (40 mL) was added $NaN_3$ (3.5 g, 53.4 mmol) and $NH_4Cl$ (2.3 g, 42.72 mmol). The reaction mixture was heated at 125° C. overnight. After cooling to room temperature, the solvent was removed under reduced pressure and the residue was taken into EtOAc (50 mL), washed with water (10 mL×2) and dried over anhydrous $Na_2SO_4$. Concentration in vacuo followed by flash chromatography (hexane-EtOAc: 1:1 to 1:2) on silica gel afforded 0.64 g of 239I (higher Rf) as a crystalline material. The stereochemistry was confirmed by a single x-ray crystallographic determination.

239J. Preparation of (±)-ethyl 4-azido-3,5-dihydroxypiperidine-1-carboxylate

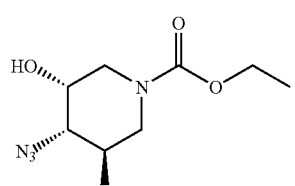

239J

Compound 239J was prepared from 239H in a similar reaction as Compound 239I as a crystalline material.

239K. Preparation of (meso)-4-azido-3,5-bis(methoxymethoxy)piperidine

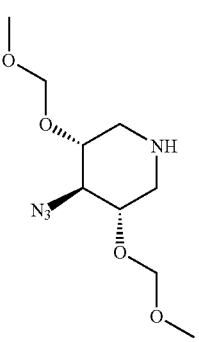

239K

To a solution of Compound 239I (640 mg, 2.78 mmol) in dry $CH_2Cl_2$ (5 mL) was added i-$Pr_2NEt$ (5.9 mL, 33.4 mmol), followed by MOMCl (1.69 mL, 22.2 mmol). The reaction mixture was heated at 60° C. overnight. After cooling to room temperature, the reaction was diluted with CH₂Cl₂, washed with 10% citric acid, sat'd NaHCO₃ and brine, and dried over anhydrous Na₂SO₄. Concentration in vacuo gave the crude intermediate as an oil, which was used immediately in the next reaction step without further purification.

The mixture of the above prepared intermediate and KOH (1.84 g, 85%) in 8 mL of EtOH and 4 mL of water was heated to reflux overnight. After cooling to room temperature, the solvent was removed under reduced pressure and the residue was diluted with water and extracted with CH₂Cl₂ (×2). The combined organic layers were dried over anhydrous Na₂SO₄. Concentration in vacuo afforded 662 mg of 239K as an oil. This material was used directly in the next reaction step without further purification.

¹H-NMR (400 MHz, CDCl₃): 4.73 (q, J=6.82 Hz, 4H), 3.41 (s, 6H), 3.20–3.40 (m 5H), 2.46 (m, 2H).

239L. Preparation of (±)-(3R,5R)-rel-4-azido-3,5-bis(methoxymethoxy)-piperidine

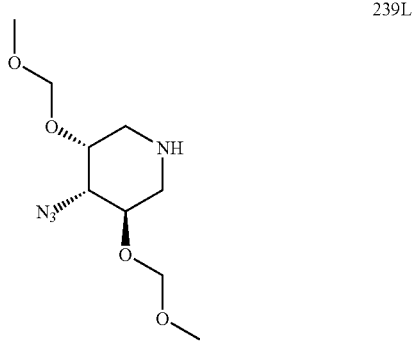

239L

Compound 239L was prepared from 239J in a similar reaction as Compound 239K as a crystalline material.

¹H-NMR (400 MHz, CDCl₃): 4.72 (q, J=6.82 Hz, 4H), 3.92 (m, 1H), 3.79 (m, 1H), 3.49 (m, 1H), 3.42 (s, 3H), 3.41 (s, 1H), 3.25 (m, 1H), 3.03 (m, 1H), 2.70 (m, 1H), 2.53 (m, 1H).

239M. Preparation of (±)-(3S,4r,5R)-rel-4-azido-1-((4-(3-methoxyphenylamino)-pyrrolo[1,2-f][1,2,4]triazin-5-yl)methyl)-3,5-bis(methoxymethoxy)piperidine

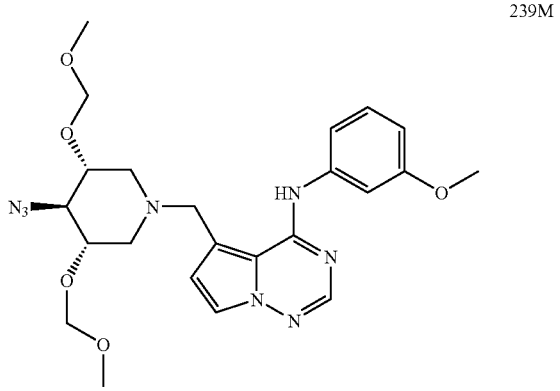

239M

Compound 239M was prepared from 239K in a same reaction as Compound 146E as a foam. Compound 239M had an analytical HPLC retention time=2.582 min. (Chromolith SpeedROD column 4.6×50 mm, 10–90% aqueous methanol containing 0.1% TFA over 4 minutes, 4 mL/min, monitoring at 254 nm) and a LC/MS M⁺+1=502⁺.

239N. Preparation of (3S,4r,5R)-rel-4-azido-1-((4-(3-methoxyphenylamino)pyrrolo[1,2-f][1,2,4]triazin-5-yl)methyl)piperidine-3,5-diol

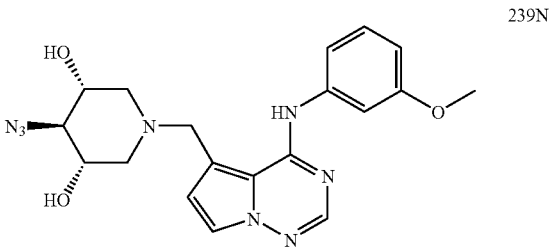

239N

The mixture of Compound 239M (0.65 mmol) and 6N HCl (2 mL) in 3 mL of THF was heated at 50° C. for 2 hrs. After cooling to room temperature, the mixture was made basic with NaOH, extracted with EtOAc and dried over anhydrous Na₂SO₄. Concentration in vacuo afforded 260 mg of 239N as a solid. Compound 239N had an analytical HPLC retention time=2.063 min. (Chromolith SpeedROD column 4.6×50 mm, 10–90% aqueous methanol containing 0.1% TFA over 4 minutes, 4 mL/min, monitoring at 254 nm) and a LC/MS M⁺+1=411⁺.

The mixture of Compound 239N (260 mg, 0.633 mmol) and Ph₃P (332 mg, 1.27 mmol) in THF (3 mL) and water (0.3 mL) was heated at 70° C. overnight. After cooling to room temperature, the mixture was diluted with water, acidified with 2N HCl and washed with EtOAc (2×). The aqueous layer was basified with 2N NaOH and extracted with EtOAc (2×). The combined organic layers were washed once with water and dried over anhydrous Na₂SO₄. Concentration in vacuo followed by trituration with ether afforded 180 mg of 239 as a solid. Compound 239 had an analytical HPLC retention time=1.211 min (Chromolith SpeedROD column 4.6×50 mm, 10–90% aqueous methanol containing 0.1% TFA over 4 minutes, 4 mL/min, monitoring at 254 nm) and a LC/MS M⁺+1=385⁺.

EXAMPLE 240

(3R/S,5R/S)-4-amino-1-({4-[(3-methoxyphenyl)amino]pyrrolo[2,1-f][1,2,4]triazin-5-yl}methyl)piperidine-3,5-diol

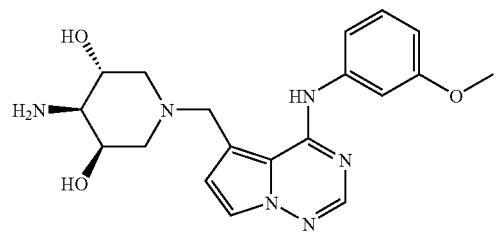

Compound 240 was prepared from 239L in a similar way as Compound 239.

Compound 240 is a solid and had an analytical HPLC retention time=1.045 min. (Chromolith SpeedROD column 4.6×50 mm, 10–90% aqueous methanol containing 0.1% TFA over 4 minutes, 4 mL/min, monitoring at 254 nm) and a LC/MS M++1=384+.

EXAMPLE 241A (3S,5S)-4-amino-1-({4-[(3-methoxyphenyl)amino]pyrrolo[2,1-f][1,2,4]triazin-5-yl}methyl)piperidine-3,5-diol (Enantiomer A, Chiral)

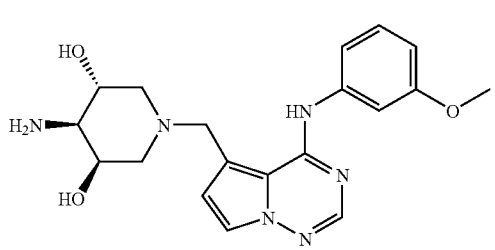

Compound 241A (Enantiomer A) was prepared from 240 by chiral preparative HPLC separation (using Chiralpak AD, eluted with EtOH/DEA: 100/0.1), as the first peak (Rt=5.827 min) with ee≧99%.

Compound 241A is a solid and had an analytical HPLC retention time=1.044 min. (Chromolith SpeedROD column 4.6×50 mm, 10–90% aqueous methanol containing 0.1% TFA over 4 minutes, 4 mL/min, monitoring at 254 nm) and a LC/MS M++1=384+.

EXAMPLE 241B (3R,5R)-4-amino-1-({4-[(3-methoxyphenyl)amino]pyrrolo[2,1-f][1,2,4]triazin-5-yl}methyl)piperidine-3,5-diol (Enantiomer B, Chiral)

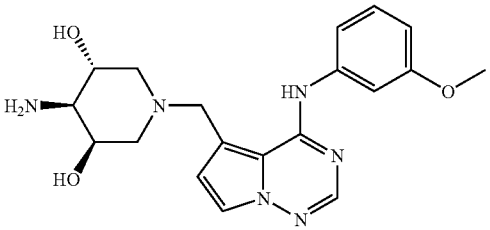

Compound 241B (Enantiomer B) was obtained from 240 by chiral preparative HPLC separation (using Chiralpak AD, eluted with EtOH/DEA: 100/0.1), as the second peak (Rt=8.430 min) with ee≧96%.

EXAMPLES 242–246

Compounds 242–246 (with HPLC note (b)) were prepared from either 239L in a similar process as Compound 239.

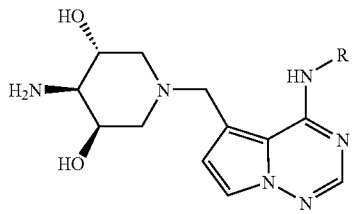

| Ex. | R | Compound Name | [M + H] | HPLC Ret Time (min) |
|---|---|---|---|---|
| 242 | ![F, 4-fluoro-3-methoxyphenyl group] Enantiomer A | (3S,5S)-4-amino-1-({4-[(4-fluoro-3-methoxyphenyl)amino]pyrrolo[2,1-f][1,2,4]triazin-5-yl}-methyl)piperidine-3,5-diol | 403 | 0.958 (4.565a) |
| 243 | ![F, 4-fluoro-3-methoxyphenyl group] Enantiomer B | (3R,5R)-4-amino-1-({4-[(4-fluoro-3-methoxyphenyl)amino]pyrrolo[2,1-f][1,2,4]triazin-5-yl}-methyl)piperidine-3,5-diol | 403 | 0.958 (5.395a) |

-continued

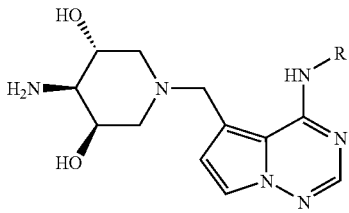

| Ex. | R | Compound Name | [M + H] | HPLC Ret Time (min) |
|---|---|---|---|---|
| 244 | (3-ethynylphenyl, racemic) | rac-(3R,5R)-4-amino-1-({4-[(3-ethynylphenyl)-amino]pyrrolo[2,1-f][1,2,4]triazin-5-yl}methyl)piperidine-3,5-diol | 379 | 1.122 |
| 245 | (3-ethynylphenyl, Enantiomer A) | (3R,5R)-4-amino-1-({4-[(3-ethynylphenyl)-amino]pyrrolo[2,1-f][1,2,4]triazin-5-yl}methyl)piperidine-3,5-diol | 379 | 1.122 (8.496[a]) |
| 246 | (3-ethynylphenyl, Enantiomer B) | (3S,5S)-4-amino-1-({4-[(3-ethynylphenyl)-amino]pyrrolo[2,1-f][1,2,4]triazin-5-yl}methyl)piperidine-3,5-diol | 379 | 1.122 (12.704[a]) |

[a]Chiral normal phase HPLC conditions: Chiralpak AD, isocratic, eluted with EtOH-DEA: 100/0.1.

EXAMPLE 247 rac-5-{[(3R,4R)-4-amino-3-methoxypiperidin-1-yl]methyl}-N-(3-methoxyphenyl)pyrrolo[2,1-f][1,2,4]triazin-4-amine

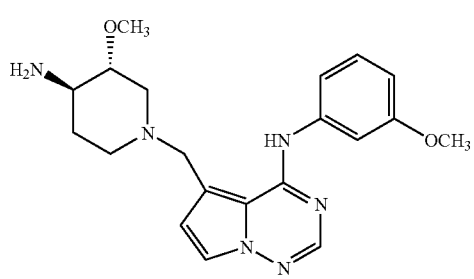

247

247A. Preparation of (3R,4R)-rel-tert-butyl 4-azido-3-methoxypiperidine-1-carboxylate

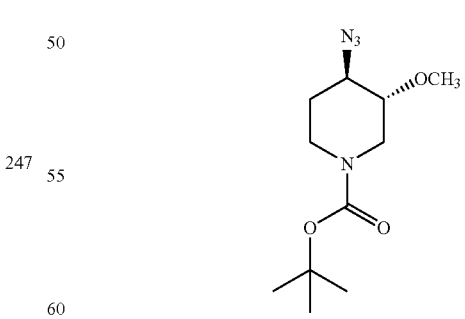

To a stirred mixture of 146A (320 mg, 1.32 mmol) and iodomethane (0.25 mL, 3.96 mmol) in 4 mL of dry THF at room temperature under nitrogen was added 95% NaH (40.0 mg, 1.58 mmol). This mixture was stirred at room temperature for 15 h and then quenched by addition of 30 mL of water. The aqueous solution was extracted with EtOAc (2×40 mL). The combined EtOAc extracts were washed with brine (30 mL), dried (MgSO₄), filtered and concentrated in vacuo to give 310 mg (Yield: 92%) of 247A. It had an analytical HPLC retention time=2.86 min. (Phenomenox S5 C18-HC 4.6×50 mm column, 10–90% aqueous methanol over 4 minutes containing 0.1% TFA, 4 ml/min, monitoring at 220 nm) and a LC/MS M$^+$+Na=279.

247B. Preparation of 5-(((3R,4R)-rel-4-azido-3-methoxypiperidin-1-yl)methyl)-N-(3-methoxyphenyl)pyrrolo[1,2-f][1,2,4]triazin-4-amine

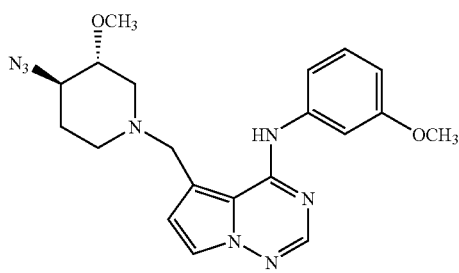

To a stirred solution of 247A (310 mg, 1.21 mmol) in 2 mL of CH₂Cl₂ at room temperature was added TFA (2.00 mL, 26.0 mmoL). This mixture was stirred at room temperature for 15 min and concentrated in vacuo to give 390 mg of (3R,4R)-rel-4-azido-3-methoxypiperidine as the TFA salt. Compound 247B was prepared from this TFA salt (52.0 mg, 0.19 mmoL) in a similar process as described for 146E. It had an analytical HPLC retention time=1.97 min. (Phenomenox S5 C18-HC 4.6×50 mm column, 10–90% aqueous methanol over 4 minutes containing 0.1% TFA, 4 ml/min, monitoring at 220 nm) and a LC/MS M$^+$+1=409.

247C. Preparation of 5-(((3R,4R)-4-amino-3-methoxypiperidin-1-yl)methyl)-N-(3-methoxyphenyl)pyrrolo[1,2-f][1,2,4]triazin-4-amine (Racemic)

Compound 247C (racemic) was prepared from 247B in a similar process as described for 146. Compound 247C was purified by passing a 1 g SCX cartridge, eluted with MeOH (16 mL), followed by the elution of 2M NH₃ in MeOH (16 mL). The eluant was concentrated in vacuo and further purified by prep HPLC to give 26 mg of 247C (Yield: 42%) as a solid. It had an analytical HPLC retention time=1.51 min. (Phenomenox S5 C18-HC 4.6×50 mm, 10–90% aqueous methanol over 4 minutes containing 0.1% TFA, 4 ml/min, monitoring at 220 nm) and a LC/MS M$^+$+1=383.

247D. Preparation of 5-(((3R,4R)-4-amino-3-methoxypiperidin-1-yl)methyl)-N-(3-methoxyphenyl)pyrrolo[1,2-f][1,2,4]triazin-4-amine (Enantiomer A)

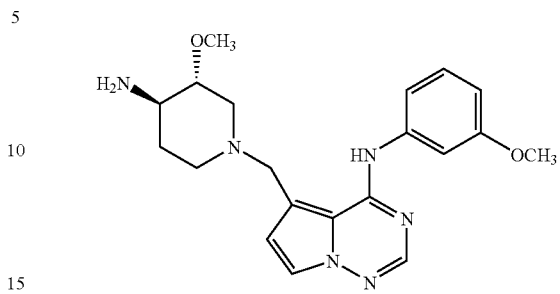

Compound 247D was obtained from Compound 247C by a chiral preparative HPLC separation (Chiralpak AD, 10 micro, 2×5 cm column, 220 nm, 20 mL/min, EtOH/MeOH/DEA, 50/50/0.1). Compound 247D is a solid and has an >99% ee with the HPLC retention time=6.5 min (Chiralpak AD, 250×4.6 mm, 10 micron; EtOH/MeOH/DEA: 50/50/0.1, 0.8 mL/min, 220 nM).

247E. Preparation of 5-(((3S,4S)-4-amino-3-methoxypiperidin-1-yl)methyl)-N-(3-methoxyphenyl)pyrrolo[1,2-f][1,2,4]triazin-4-amine (Enantiomer B)

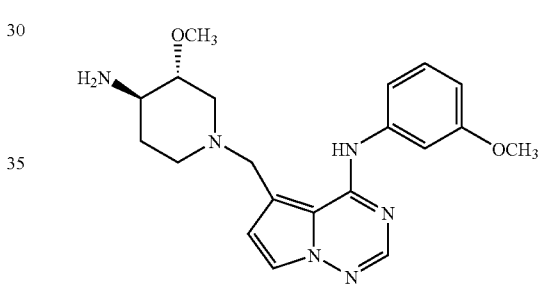

Compound 247E was obtained from Compound 247C by a chiral preparative HPLC separation (Chiralpak AD, 10 micro, 2×5 cm column, 220 nm, 20 mL/min, EtOH/MeOH/DEA, 50/50/0.1). Compound 247E is a solid and has an >99% ee with the HPLC retention time=8.9 min (Chiralpak AD, 250×4.6 mm, 10 micron; EtOH/MeOH/DEA: 50/50/0.1, 0.8 mL/min, 220 nM).

EXAMPLE 248 rac-5-{[((3R,4R)-4-amino-3-methoxypiperidin-1-yl]methyl}-N-(4-fluoro-3-methoxyphenyl)pyrrolo[2,1-f][1,2,4]triazin-4-amine

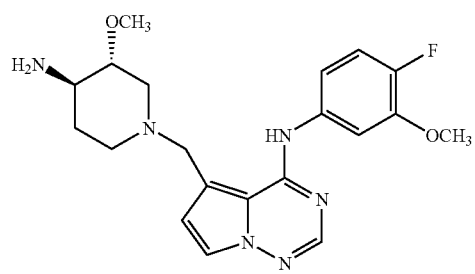

Compound 248 was prepared from 247A in a similar process as Compound 247 and had an analytical HPLC retention time=1.18 min. (Phenomenox S5 C18-HC 4.6×50 mm column, 10–90% aqueous methanol over 4 minutes containing 0.1% TFA, 4 ml/min, monitoring at 220 nm) and a LC/MS $M^++1=401$.

EXAMPLE 249

(4aR,8aR)-rel-6-((4-(3-methoxyphenylamino)pyrrolo[1,2-f][1,2,4]triazin-5-yl)methyl)-hexahydro-1H-pyrido[3,4-b][1,4]oxazin-2(3H)-one

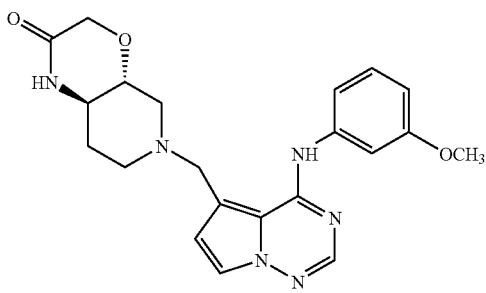

249A. Preparation of (3R,4R)-rel-tert-butyl 4-amino-3-hydroxypiperidine-1-carboxylate

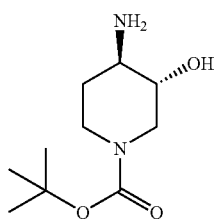

To a stirred solution of 15A (540 mg, 2.23 mmol) in 10 mL of MeOH under $N_2$ was added 20% Pd(OH)$_2$/C (108 mg). The reaction flask was purged with $H_2$ several times and stirred under hydrogen atmosphere for 18 hrs. The catalyst was removed by filtration through a 4 μM polycarbonate film and rinsed with MeOH (6×30 mL). The filtrate was concentrated in vacuo to give 453 mg (Yield: 94%) of 249A. It had an analytical HPLC retention time=0.73 min. (Chromolith SpeedROD 4.6×50 mm, 10–90% aqueous methanol over 4 minutes containing 0.2% phosphoric acid, 4 ml/min, monitoring at 220 nm) and a LC/MS $M^++1=217$.

249B. Preparation (3R,4R)-rel-tert-butyl 4-(2-chloroacetamido)-3-hydroxypiperidine-1-carboxylate

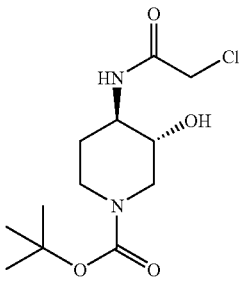

To a stirred mixture of 249A (428 mg, 1.98 mmol) and NaOAc (325 mg, 3.96 mmol) in 2.5 mL of acetone and 0.8 mL of water under $N_2$ at 0° C. was added dropwise chloroacetyl chloride (0.17 mL, 2.08 mmol) over 5 min. This mixture was stirred at 0° C. for 10 min and at room temperature for 25 min. The mixture was diluted with 160 mL of EtOAc and washed with water (2×40 mL), saturated NaHCO$_3$ solution (1×30 mL) and brine (1×30 mL). The EtOAc layer was dried (MgSO$_4$), filtered and concentrated in vacuo to give 415 mg (yield: 72%) of 249B. It had an analytical HPLC retention time=1.96 min. (Chromolith SpeedROD 4.6×50 mm, 10–90% aqueous methanol over 4 minutes containing 0.2% phosphoric acid, 4 ml/min, monitoring at 220 nm) and a flow injection MS $M^-=291$.

249C. Preparation (4aR,8aR)-rel-tert-butyl 2-oxo-hexahydro-1H-pyrido[3,4-b][1,4]oxazine-6(7H)-carboxylate

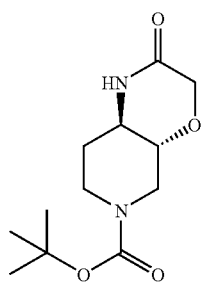

To a stirred mixture of 249B (410 mg, 14.0 mmol) in 10 mL of dry THF under $N_2$ at room temperature was added 60% NaH (84.0 mg, 2.10 mmol). This mixture was stirred at room temperature for 45 min and quenched with 3 mL of saturated NH$_4$Cl solution. The mixture was concentrated in vacuo and diluted with 40 mL of saturated NaHCO$_3$ solution. The aqueous solution was extracted with EtOAc (3×60 mL). The combined EtOAc extracts were washed with brine (1×30 mL). The EtOAc layer was dried (MgSO$_4$), filtered and concentrated in vacuo to give 344 mg (yield: 96%) of 249C. It had an analytical HPLC retention time=2.01 min. (Chromolith SpeedROD 4.6×50 mm, 10–90% aqueous methanol over 4 minutes containing 0.2% phosphoric acid, 4 ml/min, monitoring at 220 nm) and a LC/MS $M^+=257$.

249D. Preparation (4aR,8aR)-rel-hexahydro-1H-pyrido[3,4-b][1,4]oxazin-2(3H)-one

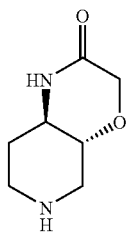

To a stirred mixture of 249C (70.0 mg, 0.0.27 mmol) in 1 mL of CH₂Cl₂ at room temperature was added TFA (2.00 mL, 25.9 mmol). The mixture was stirred at room temperature for 1 hr and concentrated in vacuo to give crude 249D. This material was mixed with DMA to make a 2 mL stock solution and was used as is in next step reaction.

Compound 249 was prepared from 249D in a similar process as Compound 146. It had an analytical HPLC retention time=1.85 min. (Phenomenox S5 C18-HC 4.6×50 mm column, 10–90% aqueous methanol over 4 minutes containing 0.1% TFA, 4 ml/min, monitoring at 220 nm) and a LC/MS M⁺+1=409.

EXAMPLE 250

5-(((4aR,8aR)-rel-hexahydro-1H-pyrido[3,4-b][1,4]oxazin-6(7H)-yl)methyl)-N-(3-methoxyphenyl)pyrrolo[1,2-f][1,2,4]triazin-4-amine

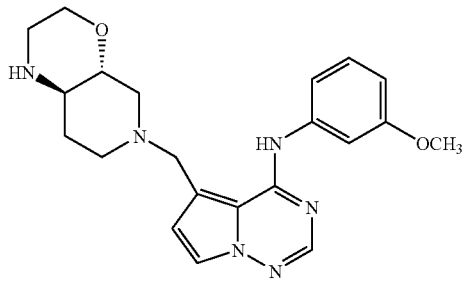

To a stirred mixture of Compound 249 (100 mg, 0.24 mmoL) at room temperature in 4 mL of dry THF was added dropwise 1M LiAlH₄/ether solution (0.70 mL, 0.70 mmoL). This mixture was stirred at room temperature for 70 min and quenched by the addition of 200 mg of Celite and 200 mg of sodium sulfate decahydrate. The mixture was stirred at room temperature for 50 min. The insoluble was filtered off and rinsed with MeOH (3×15 mL). The filtrate was concentrated in vacuo and purified by a prep HPLC to give 78 mg (yield: 81%) of Compound 250. It had an analytical HPLC retention time=1.68 min. (Phenomenox S5 C18-HC 4.6×50 mm column, 10–90% aqueous methanol over 4 minutes containing 0.1% TFA, 4 ml/min, monitoring at 220 nm) and a LC/MS M⁺+1=395.

EXAMPLE 251

N-(4-fluoro-3-methoxyphenyl)-5-(((4aR,8aR)-rel-hexahydro-1H-pyrido[3,4-b][1,4]oxazin-6(7H)-yl)methyl)pyrrolo[1,2-f][1,2,4]triazin-4-amine

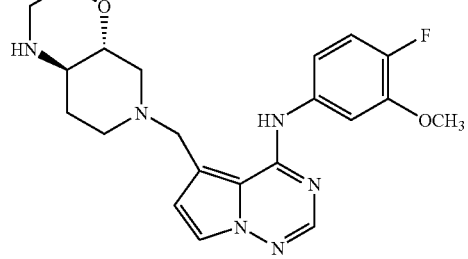

Compound 251 was prepared from 249D in a similar process as Compound 250. It had an analytical HPLC retention time=1.64 min. (Phenomenox S5 C18-HC 4.6×50 mm column, 10–90% aqueous methanol over 4 minutes containing 0.1% TFA, 4 ml/min, monitoring at 220 nm) and a LC/MS M⁺+1=413.

EXAMPLE 252

(3R,4R)-4-amino-1-({4-[(3-methoxyphenyl)amino]pyrrolo[2,1-f][1,2,4]triazin-5-yl}methyl)-N-(methylsulfonyl)piperidine-3-carboxamide

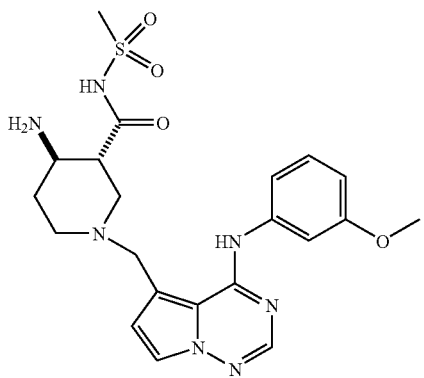

252A. Preparation of 1-tert-butyl 3-ethyl 4-oxopiperidine-1,3-dicarboxylate

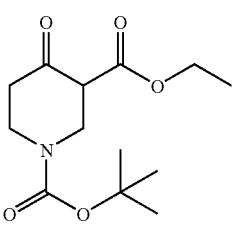

A solution of ethyl 4-oxopiperidine-3-carboxylate (16.2 g, 95 mmol) in CHCl₃ (160 mL) was treated with a solution of NaHCO₃ (9.6 g, 114 mmol) in water (170 mL). This biphasic reaction was treated with a solution of Boc₂O (20.7 g, 95 mmol) in CHCl₃ (60 mL). The resulting reaction was heated to reflux for 18 hours, cooled to room temperature and the layers were separated. The aqueous layer was extracted with CHCl₃ (2×100 mL). The combined organic layers were dried (Na₂SO₄), filtered and concentrated to give 22 g (yield: 86%) of Compound 252A as an oil.

252B. Preparation of (R)-1-tert-butyl 3-ethyl 4-(1-phenyl-ethylamino)-5,6-dihydro-pyridine-1,3(2H)-dicarboxylate after the final addition. The mixture was then cooled to −10° C. and slowly quenched by addition of 1 N NaOH (100 mL), 4 N NaOH (100 mL), 6 N NaOH (100 mL) followed by 50% NaOH (50 mL). The reaction was warmed to room temperature and the layers were separated. The aqueous layer was extracted with CH₂Cl2₂ (2×250 mL) and the combined organic layers were dried (Na₂SO₄), filtered and concentrated in vacuo. Purification by flash chromatography (10% to 30% EtOAc/hexane gradient) on silica gel afforded 6.0 g (yield: 41%) of Compound 252C.

252D. Preparation of (3R,4R)-1-tert-butyl 3-ethyl 4-((R)-1-phenylethylamino)-piperidine-1,3-dicarboxylate

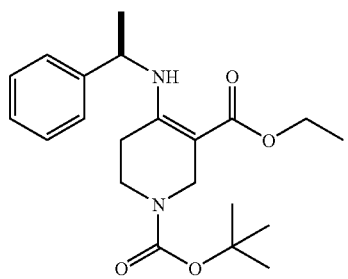

252B

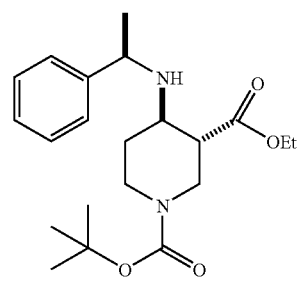

252D

A solution of 252A (22 g, 81 mmol) and toluene (400 mL) was treated with (R)-1-phenylethanamine (12.5 mL, 97 mmol) and p-TsOH (1.5 g). The reaction mixture was heated to reflux with a Dean-Stark trap for 23 hours. The mixture was cooled to room temperature, washed with saturated aqueos NaHCO₃ (2×200 mL) and brine (2×200 mL). The combined organic layers were dried (Na₂SO₄), filtered and concentrated. The crude material was filtered through a pad of silica (100% CH₂Cl₂) and concentrated to provide 14.7 g (yield: 49%) of Compound 252B as an oil.

252C. Preparation of (3S,4R)-1-tert-butyl 3-ethyl 4-((R)-1-phenylethylamino)-piperidine-1,3-dicarboxylate A solution of 252C (2.90 g, 7.71 mmol) in ethanol (70 mL) was treated with 21% NaOEt in ethanol (7.5 mL). The reaction mixture was heated to 50° C. for three hours, cooled to room temperature, and then concentrated. The resulting oil was taken up in dichloromethane (150 mL), washed with 20% NH4Cl (2×50 mL). The organic layer was dried (Na₂SO₄) and concentrated to an oil. Purification by flash chromatography (10 to 25% EtOAc/Hexane gradient) on silica gel afforded 1.20 g (yield: 41%) of Compound 252D as an oil.

252E. Preparation of (3R,4R)-1-tert-butyl 3-ethyl 4-aminopiperidine-1,3-dicarboxylate.

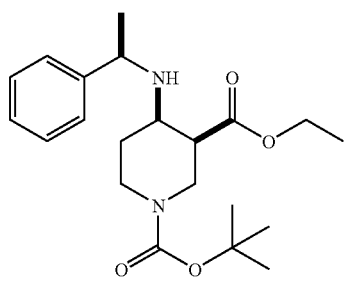

252C

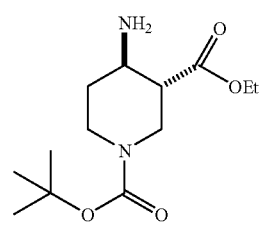

252E

A 1L 3-neck round bottom flask equipped with a mechanical stirrer and addition funnel was charged with 252B (14.7 g, 39 mmol) and acetonitrile (200 mL) and acetic acid (100 mL). The solution was cooled to 0° C. and Na(OAc)₃BH (33.3 g, 157 mmol) was added in three portions over 2 hours. The reaction was stirred for two hours at this temperature A solution of 252D (1.18 g, 3.13 mmol) in MeOH (31 mL) was treated with ammonium formate (1.58 g, 25.1 mmol) and 10% Pd/C. The reaction mixture was heated to reflux for 14 hours then cooled to room temperature. The resulting solid was removed by filtration and washed with MeOH. The filtrate was dried (Na₂SO₄) and concentrated under reduced pressure to give 0.82 g (yield: 96%) of Compound 252E as an oil.

252F. Preparation of (3R,4R)-1-tert-butyl 3-ethyl 4-aminopiperidine-1,3-dicarboxylate

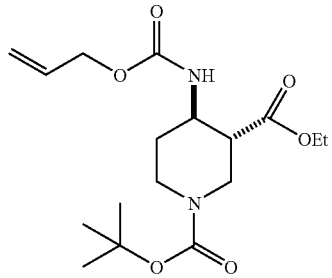

252F

A solution of 252E (0.80 g, 2.94 mmol) in dichloromethane (29 mL) at 0° C. was treated with diisopropylethylamine (0.41 g, 3.23 mmol). A solution of allylchloroformate (0.46 g, 3.83 mmol) in dichloromethane (29 mL) was slowly added over 30 minutes. The reaction mixture was stirred at 0° C. for 16 hours, then slowly warmed to room temperature. The resulting solution was diluted with dichloromethane and washed with saturated NaHCO$_3$ (2×50 mL). The organic layer was dried (Na$_2$SO$_4$) and concentrated under reduced pressure. The resulting oil was purified by flash chromatography (20 to 25% EtOAc/Hexane) on silica gel to give 0.88 g (yield: 84%) of Compound 252F as an oil.

252G. Preparation of (3R,4R)-methyl 4-(allyloxycarbonyl)piperidine-3-carboxylate

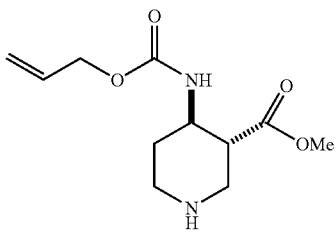

252G

A solution of 252F (0.87 g, 2.44 mmol) in dichloromethane (12 mL) was treated with TFA (2.4 mL) at 0° C. The reaction mixture was stirred at 0° C. for one hour then allowed to slowly warm to room temperature. Stirring was continued at this temperature for five hours, concentrated, and azeotropically evaporated with MeOH and toluene. The resulting oil was purified by flash chromatography (0 to 2% MeOH/CH$_2$Cl$_2$) on silica gel to give 0.47 g (yield: 79%) of Compound 252G as an oil.

252H. Preparation of (3R,4R)-methyl 4-(allyloxycarbonyl)-1-((4-(3-methoxyphenyl-amino)pyrrolo[1,2-f][1,2,4]triazin-5-yl)methyl)piperidine-3-carboxylate

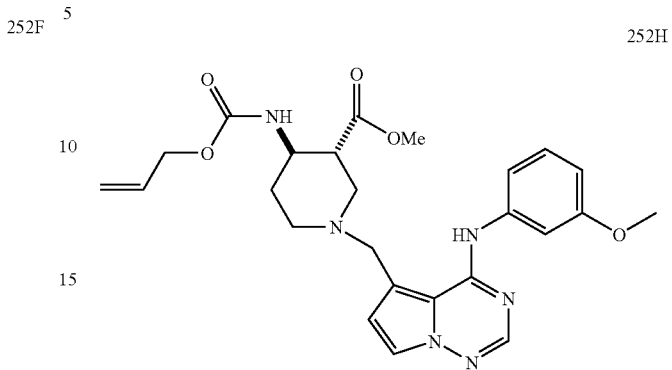

252H

A suspension of 252G (0.21 g, 0.87 mmol), 4-(3-methoxyphenylamino)-pyrrolo[1,2,4]trizin-5-ylmethyl triethylammonium bromide (0.40 g, 0.87 mmol), and diisopropylethylamine (0.11 g, 0.87 mmol) in MeCN (15 mL) was heated to 60° C. for one hour then concentrated in vacuo. The resulting oil was purified by flsh chromatography (2 to 5% MeOH/CH$_2$Cl$_2$) on silic gel to give 0.33 g (yield: 77%) of Compound 252H as a solid.

252I. Preparation of (3R,4R)-4-(allyloxycarbonyl)-1-((4-(3-methoxyphenylamino)-pyrrolo[1,2-f][1,2,4]triazin-5-yl)methyl)piperidine-3-carboxylic acid

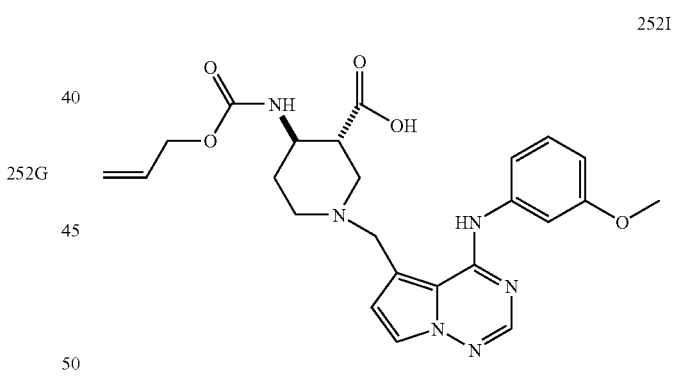

252I

A solution of 252H (0.33 g, 0.67 mmol) in MeOH/THF/water (3/3/1/mL) was treated with LiOH monohydrate (0.25 g, 6.7 mmol). The reaction mixture was stirred for 14 hours, neutralized to pH=7 with saturated aqueous NaHCO$_3$, then concentrated to a volume of 1 mL. The resulting slurry was dissolved in MeOH and purified by preparative HPLC (YMC ODS-A 5 um, 20×100 mm, solvent A 10% MeOH-90% H$_2$O-0.1% TFA, solvent B 90% MeOH-10% H$_2$O-0.1% TFA, gradient 0–100% B, 12 mintues). The desired fractions were combined and concentrated under reduced pressure to remove most of the MeOH, neutralized with saturated aqueous NaHCO$_3$ to pH=7, and extracted with EtOAc (2×50 mL). The combined organic layers were dried (Na$_2$SO$_4$) and concentrated to give 0.30 g (yield: 94%) of Compound 252I as a solid.

131

252J. Preparation of allyl (3R,4R)-1-((4-(3-methoxyphenylamino)pyrrolo[1,2-f][1,2,4]-triazin-5-yl)methyl)-3-(methylsulfonylcarbamoyl)piperidin-4-ylcarbamate

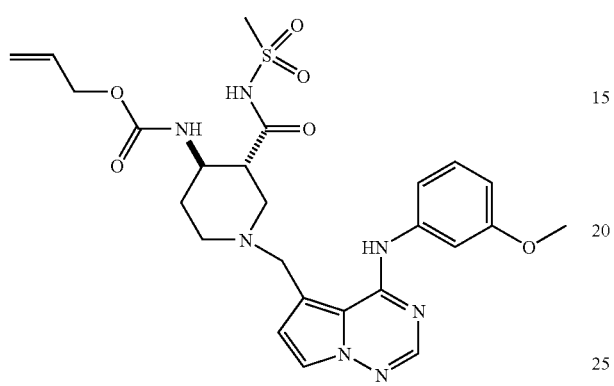

252J

A solution of 252I (0.30 g, 0.63 mmol) in MeCN (6.2 mL) was treated with dimethylaminopiperidine (77 mg, 0.63 mmol), DECI (0.18 g, 0.94 mmol), followed by methanesulfonamide (0.18 g, 1.88 mmol). The reaction mixture was stirred for two hours, quenched with water, and concentrated. The resulting slurry was dissolved in MeOH and purified by preparative HPLC (YMC ODS-A 5 um, 20×100 mm, solvent A 10% MeOH-90% $H_2O$-0.1% TFA, solvent B 90% MeOH-10% $H_2O$-0.1% TFA, gradient 0–100% B, 12 minutes). The desired fractions were combined and concentrated in vacuo, neutralized with saturated aqueous $NaHCO_3$ to pH=10, and extracted with EtOAc (2×50 mL). The combined organic layers were dried ($Na_2SO_4$) and concentrated to give 0.22 g (yield: 62%) of Compound 252J as a solid.

A solution of 252J (100 mg, 0.18 mmol) in THF (4 mL, degassed with argon) was treated with Pd(PPh$_3$)$_4$ (21 mg, 0.018 mmol) and Et$_2$NH (33 mg, 0.45 mmol). The reaction mixture was stirred for 90 minutes then concentrated. The resulting solid was dissolved in MeOH, purified by preparative HPLC (YMC ODS-A 5 um, 20×100 mm, solvent A 10% MeOH-90% $H_2O$-0.1% TFA, solvent B 90% MeOH-10% $H_2O$-0.1% TFA, gradient 0–100% B, 12 minutes). The desired fractions were concentrated to, neutralized with saturated aqueous $NaHCO_3$ to pH=10, and extracted with EtOAc (2×50 mL). The combined organic layers were dried ($Na_2SO_4$) and concentrated to give 36 mg (yield: 42%) of Compound 252 as a solid. It had an analytic HPLC retention time=1.62 min (Phenomenex Su C18 4.6×50 mm column 10–90% aqueous methanol containing 0.2% $H_3PO_4$, 4 min grad. monitored at 220 nm), [M+H]$^+$=474.

132

EXAMPLE 253

(3R,4R)-4-amino-1-({4-[(3-ethynylphenyl)amino]pyrrolo[2,1-f][1,2,4]triazin-5-yl}methyl)-N-methylpiperidine-3-carboxamide

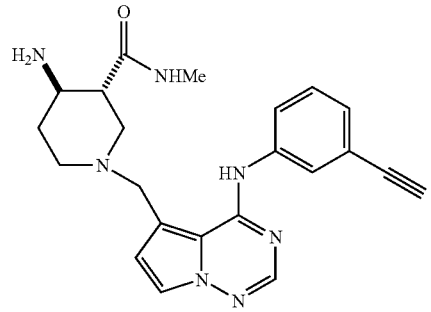

253

253A. Preparation of (3R,4R)-methyl 4-(allyloxycarbonyl)-1-((4-(3-ethynylphenyl-amino)pyrrolo[1,2-f][1,2,4]triazin-5-yl)methyl)piperidine-3-carboxylate

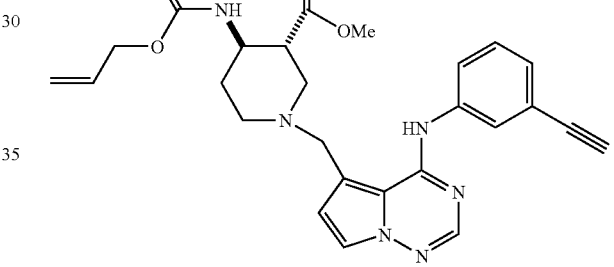

A suspension of 252G (0.24 g, 1.0 mmol), 4-(3-ethynylphenylamino)-pyrrolo[1,2,4]trizin-5-ylmethyl triethylammonium bromide (0.43 g, 1.0 mmol), and diisopropylethyl amine (0.13 g, 1.0 mmol) in MeCN (15 mL) was heated to 60° C. for one hour, then concentrated in vacuo. The residue was purified by flash chromatography (2 to 5% MeOH/CH$_2$Cl$_2$) on silica gel gave 0.24 g (yield: 50%) of Compound 253A as a solid.

253B. Preparation of (3R,4R)-4-(allyloxycarbonyl)-1-((4-(3-ethynylphenylamino)-pyrrolo[1,2-f][1,2,4]triazin-5-yl)methyl)piperidine-3-carboxylic acid

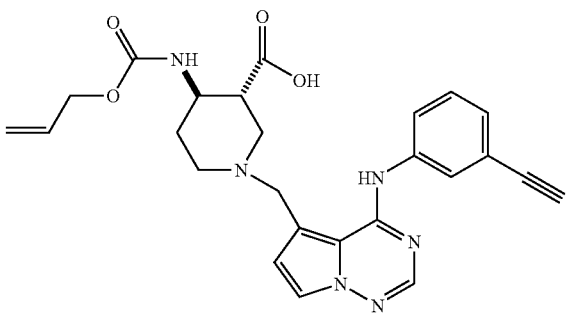

253B

A solution of 253A (0.24 g, 0.50 mmol) in MeOH/THF/water (3/3/1/mL) was treated with LiOH monohydrate (0.21 g, 5.0 mmol) at room temperature. The reaction mixture was stirred for 14 hours, neutralized to pH=7 with saturated aqueous NaHCO$_3$, then concentrated. The resulting slurry was dissolved in MeOH and purified by preparative HPLC (YMC ODS-A 5 um, 20×100 mm, solvent A 10% MeOH-90% H$_2$O-0.1% TFA, solvent B 90% MeOH-10% H$_2$O-0.1% TFA, gradient 0–100% B, 12 minutes). The desired fractions were concentrated, neutralized with saturated NaHCO$_3$ to pH=7, and extracted with EtOAc (2×50 mL). The combined organic layers were dried (Na$_2$SO$_4$) and concentrated in vacuo to give 0.22 g (yield: 93%) of Compound 253B as a solid.

253C. Preparation of allyl (3R,4R)-1-((4-(3-ethynylphenylamino)pyrrolo[1,2-f][1,2,4]-triazin-5-yl)methyl)-3-(methylcarbamoyl)piperidin-4-ylcarbamate

253C

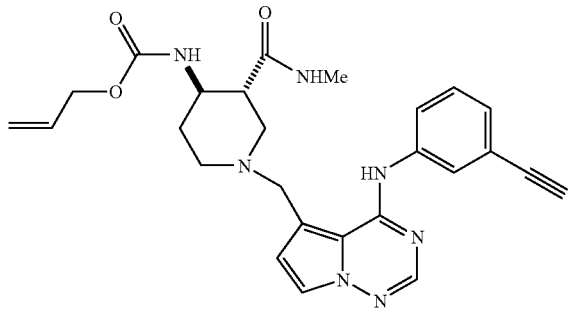

A solution of 253B (0.22 g, 0.46 mmol) in MeCN (4.6 mL) was treated with diisopropylethylamine (59 mg, 0.46 mmol), benzotriazol-1-yloxy-tris(dimethylamino)phosphonium hexafluorophosphate (hereinafter referred to as the "Bop Reagent") (0.36 g, 0.69 mmol), and 2 N methylamine in THF (0.70 mL, 1.38 mmol). The reaction mixture was stirred for two hours, quenched with water, and concentrated. The resulting slurry was dissolved in MeOH and purified by preparative HPLC (YMC ODS-A 5 um, 20×100 mm, solvent A 10% MeOH-90% H$_2$O-0.1% TFA, solvent B 90% MeOH-10% H$_2$O-0.1% TFA, gradient 0–100% B, 12 minutes). The desired fractions were concentrated, neutralized by saturated aqueous NaHCO$_3$ to pH=10, and extracted with EtOAc (2×50 mL). The combined organic layers were dried (Na$_2$SO$_4$) and concentrated in vacuo to give 0.21 g (yield: 92%) of Compound 253C as a solid.

A solution of 253C (100 mg, 0.20 mmol) in THF (5 mL, degassed with argon) was treated with Pd(PPh$_3$)$_4$ (23 mg, 0.020 mmol) and Et$_2$NH (37 mg, 0.51 mmol). The reaction mixture was stirred for 90 minutes, and then concentrated. The resulting solid was dissolved in MeOH and purified by preparative HPLC (YMC ODS-A 5 um, 20×100 mm, solvent A 10% MeOH-90% H$_2$O-0.1% TFA, solvent B 90% MeOH-10% H$_2$O-0.1% TFA, gradient 0–100% B, 12 minutes). The desired fractions were concentrated, neutralized with saturated aqueous NaHCO$_3$ to pH=10, and extracted with EtOAc (2×50 mL). The combined organic layers were dried (Na$_2$SO$_4$) and concentrated in vacuo to give 36 mg (yield: 42%) of Compound 253 as a solid. It had an analytic HPLC retention time=1.96 min (Phenomenex Su C18 4.6×50 mm column 10–90% aqueous methanol containing 0.2% H$_3$PO$_4$, 4 min grad. monitored at 220 nm), [M+H]$^+$=404.

EXAMPLE 254

(3R,4R)-4-amino-1-({4-[(3-methoxyphenyl)amino]pyrrolo[2,1-f][1,2,4]triazin-5-yl}methyl)-N-methylpiperidine-3-carboxamide

254

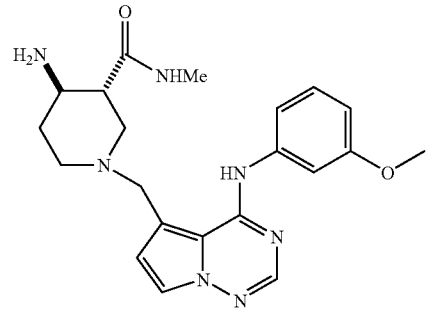

254A. Preparation of (3R,4R)-1-tert-butyl 3-ethyl 4-(benzyloxycarbonyl)piperidine-1,3-dicarboxylate

254A

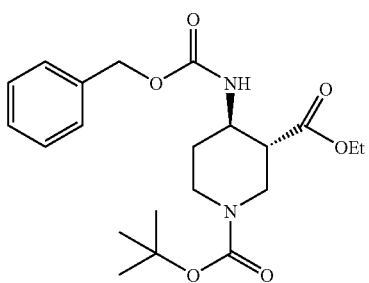

A solution of 252E (180 mg, 0.66 mmol) in CH$_2$Cl$_2$ (5 mL) was treated with benzyloxychloroformate (0.1 mL, 0.73 mmol) and triethylamine (0.12 mL, 0.86 mmol). The reaction was stirred at room temperature for 18 hours, diluted with CH$_2$Cl$_2$ (10 mL) and washed with water (2×10 mL), 0.1 N HCl (2×10 mL), saturated aqueous NaHCO$_3$ (2×10 mL) and brine (1×10 mL). The organic layer was dried (Na$_2$SO$_4$), filtered and concentrated to give 243 mg (yield: 91%) of Compound 254A as an oil.

254B. Preparation of (3R,4R)-ethyl 4-(benzyloxycarbonyl)piperidine-3-carboxylate

254B

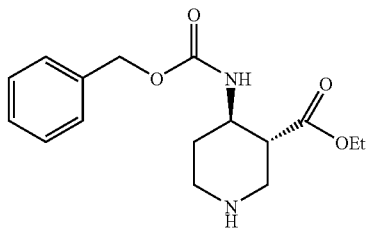

A solution of 254A (243 mg, 0.60 mmol) in CH$_2$Cl$_2$ (3 mL) at 0° C. was treated with trifluoroacetic acid (0.3 mL). The reaction was stirred at room temperature for one hour, then concentrated to an oil. The crude amine was dissolved in EtOAc (10 mL), washed with saturated aqueous NaHCO$_3$ and dried (Na$_2$SO$_4$), filtered and concentrated in vacuo. The product was purified by flash chromatography (10% MeOH/ CH$_2$Cl$_2$) on silica gel to afford 95 mg (yield: 52%) of Compound 254B.

254C. Preparation of (3R,4R)-methyl 4-(benzyloxycarbonyl)-1-((4-(3-methoxyphenyl-amino)pyrrolo[1,2-f][1,2,4]triazin-5-yl)methyl)piperidine-3-carboxylate

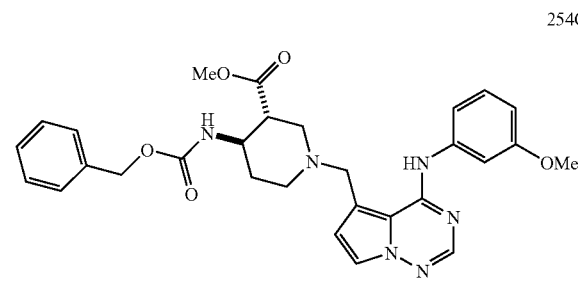

254C

A suspension of N,N-diethyl-N-((4-(3-methoxyphenylamino)pyrrolo[1,2-f][1,2,4]triazin-5-yl)methyl)ethanaminium bromide (1.7 g, 3.62 mmol) and 254B (1.06 g, 3.6 mmol) in acetonitrile (75 mL) was treated with DIEA (0.63 mL, 3.6 mmol) and warmed to 55° C. for 12 hours. The reaction was concentrated, dissolved in EtOAc (100 mL) and washed with water (2×100 mL). The crude material was dried (Na$_2$SO$_4$), filtered and concentrated to afford 1.7 g (yield: 89%) of Compound 254C.

254D. Preparation of (3R,4R)-4-(benzyloxycarbonyl)-1-((4-(3-methoxyphenylamino)-pyrrolo[1,2-f][1,2,4]triazin-5-yl)methyl)piperidine-3-carboxylic acid

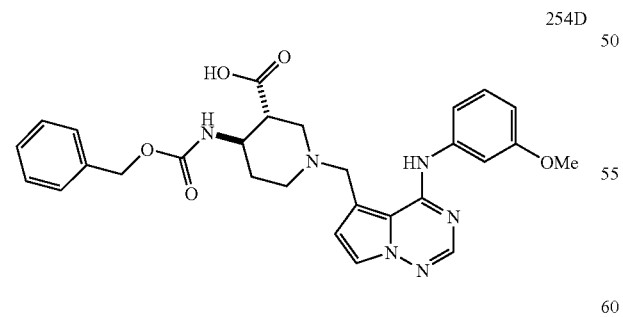

254D

Compound 254D (1.67 g, yield: 100%) was prepared from 254C (1.7 g, 3.13 mmol) in a similar process as used for Compound 252I.

254E. Preparation of Benzyl (3R,4R)-1-((4-(3-methoxyphenylamino)pyrrolo[1,2-f][1,2,4]triazin-5-yl)methyl)-3-(methylcarbamoyl)piperidin-4-ylcarbamate

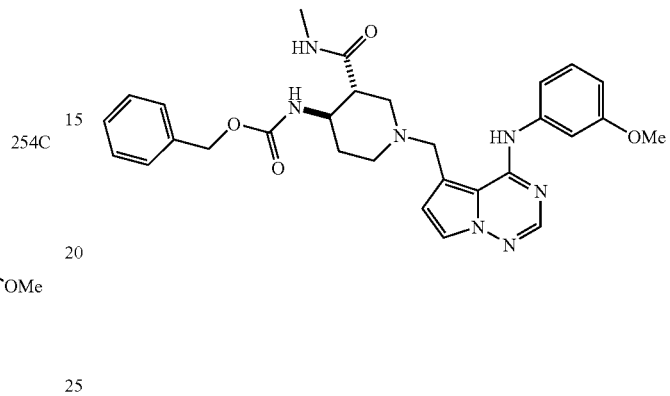

254E

Compound 254E (790 mg, yield: 54%) was prepared from 254D (1.44 g, 2.71 mmol) in a similar process as used for Compound 253C.

A solution of 254E (1.66 g, 3.13 mmol) in MeOH (50 mL) was purged with argon for 30 minutes. 5% Pd/C (300 mg) was added. The reacton mixture was stirred under a hydrogen atmosphere for three hours, then filtered through a pad of celite. The filtrate was concentrated in vitro to provide 1.21 g (yield: 94%) of Compound 254 as a solid. It had an analytical HPLC retention time=1.57 min (YMC S5 ODS 4.6×50 mm, 10–90% aqueous methanol containing 0.2% H3PO4, 4 min gradient, monitored at 220 nm), [M+H]$^+$= 410.

EXAMPLE 255

(3R,4R)-4-amino-1-({4-[(3-methoxyphenyl)amino]pyrrolo[2,1-f][1,2,4]triazin-5-yl}methyl)piperidine-3-carboxylic acid

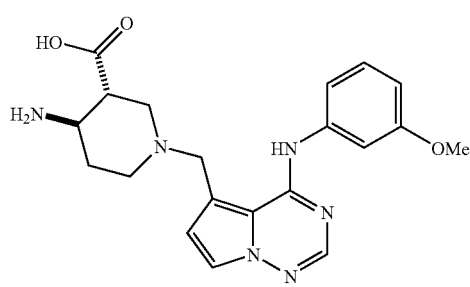

Compound 255 (33 mg, yield: 89%) was prepared from 254D (50 mg, 0.094 mmol) in a similar process as used for 254. It had an analytical HPLC retention time=1.54 min (YMC S5 ODS 4.6×50 mm, 10–90% aqueous methanol containing 0.2% H$_3$PO$_4$, 4 min gradient, monitored at 220 nm). [M+H]$^+$=397.

EXAMPLE 256

(3R,4R)-4-amino-1-({4-[(3-methoxyphenyl)amino]pyrrolo[2,1-f][1,2,4]triazin-5-yl}methyl)piperidine-3-carboxamide

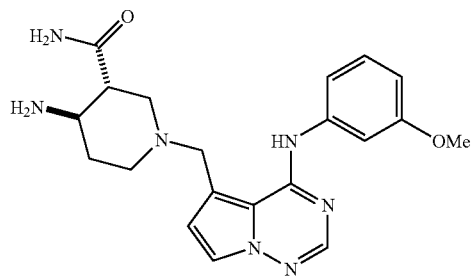

256A. Preparation of Benzyl (3R,4R)-3-((3,4-dimethoxybenzyl)carbamoyl)-1-((4-(3-methoxyphenylamino)pyrrolo[1,2-f][1,2,4]triazin-5-yl)methyl)piperidin-4-ylcarbamate

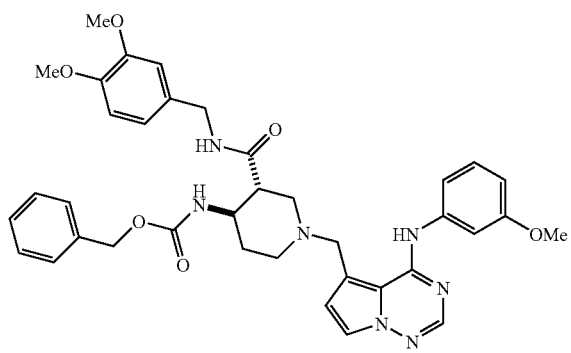

A solution of 254D (150 mg, 0.23 mmol) in DMF (5 mL) was treated with 3,4-dimethoxybenzylamine (77 mg, 0.46 mmol), DIEA (80 µL, 0.46 mmol) and Bop Reagent (132 mg, 0.25 mmol). The reaction was stirred at room temperature for four hours, then poured into EtOAc (25 mL). The mixture was washed with saturated aqueous NaHCO$_3$ (3×25 mL) and dried (Na$_2$SO$_4$), filtered and concentrated in vacuo. The crude product was purified by flash chromatography (3% MeOH/CH$_2$Cl$_2$) on silica gel to afford 174 mg (yield: 95%) of Compound 256A.

A solution of 256A (50 mg, 0.06 mmol) in TFA (3 mL) was stirred at room temperature for 5 days. The reaction was concentrated and purified by preparative HPLC to afford 7 mg (yield: 30%) of Compound 256 as a solid. It had an analytical HPLC retention time=1.62 min (YMC S5 ODS 4.6×50 mm, 10–90% aqueous methanol containing 0.2% H$_3$PO$_4$, 4 min gradient, monitored at 220 nm), [M+H]$^+$=396.

EXAMPLE 257

(3S,4R)-4-amino-1-({4-[(3-methoxyphenyl)amino]pyrrolo[2,1-f][1,2,4]triazin-5-yl}methyl)-N-(methylsulfonyl)piperidine-3-carboxamide

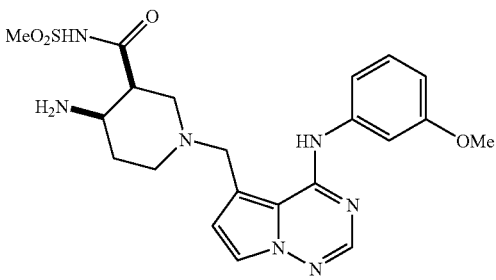

257A. Preparation of (3S,4R)-1-tert-butyl 3-methyl 4-aminopiperidine-1,3-dicarboxylate

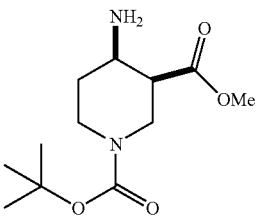

Compound 257A (447 mg, 63%) was prepared in a similar process as used for 252E.

257B. Preparation of (3S,4R)-1-tert-butyl 3-methyl 4-(benzyloxycarbonyl)piperidine-1,3-dicarboxylate

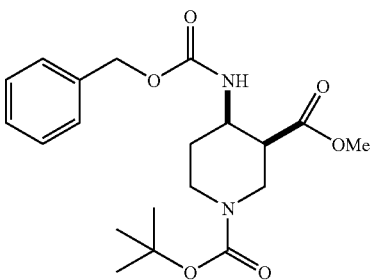

A solution of 257A (447 mg, 1.7 mmol) in CH$_2$Cl$_2$ (20 mL) was treated with triethylamine (0.3 mL, 2.2 mmol) followed by benzyl chloroformate (0.27 mL, 1.9 mmol) at room temperature. The reaction mixture was stirred for 18 hours, then washed with water (25 mL). The aqueous layer was extracted with CH$_2$Cl$_2$ (25 mL) and the combine organics were washed with saturated aqueous NaHCO$_3$, 0.1N HCl, and brine. The organic layer was dried (Na$_2$SO$_4$), filtered and concentrated in vacuo to an oil. The crude material was purified by flash chromatography (30% EtOAc/hexanes) on silica gel to afford 411 mg (yield: 75%) of Compound 257B as an oil.

257C. Preparation of (3S,4R)-methyl 4-(benzyloxycarbonyl)piperidine-3-carboxylate

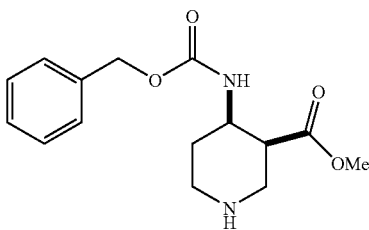

A solution of 257B (411 mg, 1.04 mmol) in CH₂Cl₂ (5 mL) was treated with TFA (0.5 mL) at room temperature. The reaction mixture was stirred for 5.0 hours, then concentrated in vacuo. The residue was dissolved in EtOAc (10 mL) and washed with saturated aqueous NaHCO₃. The organics were dried (Na₂SO₄), filtered and concentrated in vacuo to give 365 mg of 257C as a solid.

257D. Preparation of (3S,4R)-methyl 4-(benzyloxycarbonyl)-1-((4-(3-methoxyphenyl-amino)pyrrolo[1,2-f][1,2,4]triazin-5-yl)methyl)piperidine-3-carboxylate

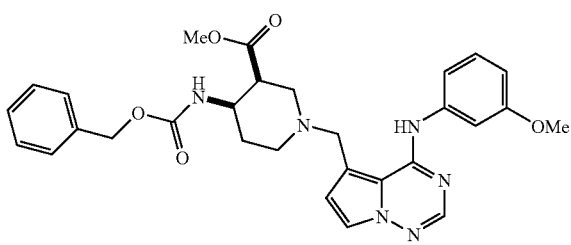

A suspension of 257C (292 mg, 0.62 mmol) and N,N-diethyl-N-((4-(3-methoxyphenylamino)pyrrolo[1,2-f][1,2,4]triazin-5-yl)methyl)ethanaminium bromide (292 mg, 0.62 mmol) in acetonitrle (10 mL) were treated with DIEA (0.2 mL, 1.24 mmol) at room temperature. The reaction mixture was warmed to 55° C. for 3.0 hours, then concentrated in vacuo to dryness. The crude residue was purified by flash chromatography (30% EtOAc/hexanes) on silica gel to afford 269 mg (yield: 80%) of 257D.

257E. Preparation of (3S,4R)-4-(benzyloxycarbonyl)-1-((4-(3-methoxyphenylamino)-pyrrolo[1,2-f][1,2,4]triazin-5-yl)methyl)piperidine-3-carboxylic acid

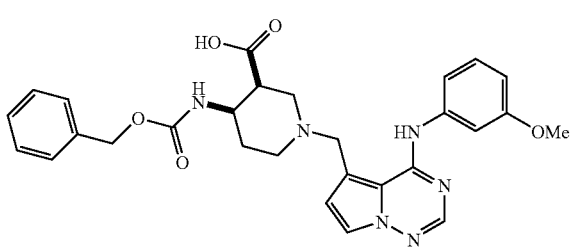

A solution of 257D (200 mg, 0.37 mmol) in THF/MeOH (1:1, 4 mL) was treated with LiOH monohydrate (30 mg, 0.74 mmol) in water (1 mL) at room temperature. The reaction mixture was stirred for eight hours, then concentrated to 1 mL. The residue was diluted with water (10 mL) and extracted with EtOAc (3×10 mL). The organics were dried (Na₂SO₄), filtered and concentrated in vacuo to afford 200 mg (yield: 100%) of Compound 257E as a solid.

257F. Preparation of (3S,4R)-1-((4-(3-methoxyphenylamino)pyrrolo[1,2-f][1,2,4]triazin-5-yl)methyl)-3-(methylsulfonylcarbamoyl)piperidin-4-ylcarbamate acid.

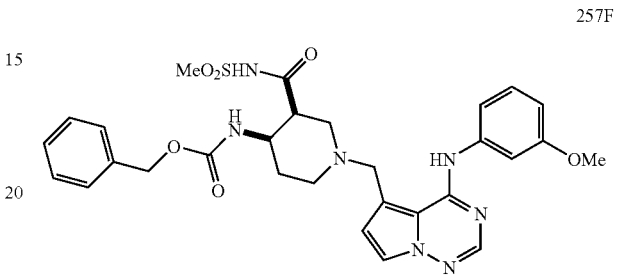

A solution of 257E (30 mg, 0.06 mmol) in DMF (2 mL) was treated with methansulfonamide (11 mg, 0.11 mmol), DMAP (7 mg, 0.06 mmol) and EDAC (13 mg, 0.07 mmol). The reaction mixture was stirred at room temperature for 48 hours. The resulting suspension was diluted with EtOAc (10 mL), washed with brine (3×10 mL), saturated aqueous NaHCO₃ (2×10 mL), dried (Na₂SO₄), filtered and concentrated in vacuo to afford 35 mg of 257E which was used without further purification.

A solution of 257F (35 mg) in MeOH (3 mL) was treated with 10% Pd/C (15 mg) and stirred under a hydrogen atmosphere for three hours at room temperature. The slurry was filtered through a nylon filter and the filtrate was concentrated. The crude material was purified by preparative HPLC to afford 12 mg of Compound 257 as a solid. It had an analytical HPLC retention time=1.77 min (YMC S5 ODS 4.6×50 mm, 10–90% aqueous methanol containing 0.2% H₃PO₄, 4 min gradient, monitored at 220 nm) [M+H]⁺=474.

EXAMPLE 258

(3R,4S)-4-amino-1-({4-[(3-methoxyphenyl)amino]pyrrolo[2,1-f][1,2,4]triazin-5-yl}methyl)-N-(methylsulfonyl)piperidine-3-carboxamide

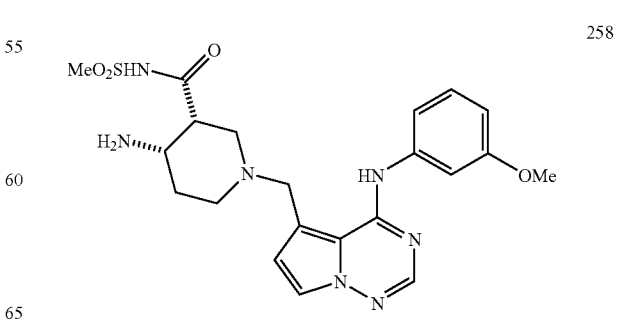

258A. Preparation of (3R,4S)-1-tert-butyl 3-methyl 4-((S)-1-phenylethylamino)-piperidine-1,3-dicarboxylate

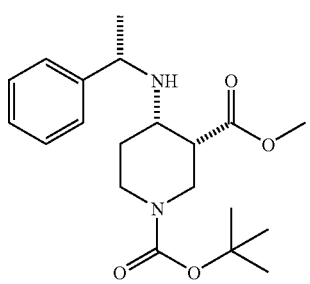

Compound 258A was prepared in the same manner as 252C using the appropriate starting materials.

258B. Preparation of (3R,4S)-1-tert-butyl 3-methyl 4-aminopiperidine-1,3-dicarboxylate

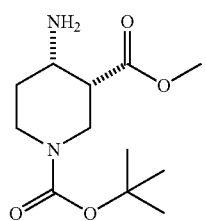

Compound 258B was prepared according to the procedures described in Example 257 using the appropriate starting materials.

Compound 258 was prepared from 258B in the same manner as described for 257. Compound 258 had an analytical HPLC retention time=1.77 min (YMC S5 ODS 4.6×50 mm, 10–90% aqueous methanol containing 0.2% $H_3PO_4$, 4 min gradient, monitored at 220 nm) $[M+H]^+=474$.

EXAMPLE 259

(3S,4R)-4-amino-1-({4-[(3-ethynylphenyl)amino]pyrrolo[2,1-f][1,2,4]triazin-5-yl}methyl)-N-methylpiperidine-3-carboxamide

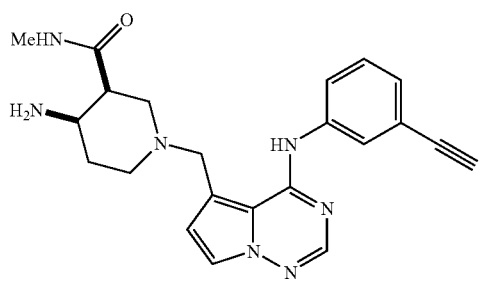

259A. Preparation of (3S,4R)-1-tert-butyl 3-ethyl 4-aminopiperidine-1,3-dicarboxylate

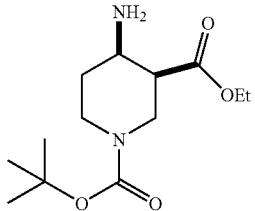

A solution of 252C (2.6 g, 6.9 mmol) in EtOH (100 mL) was treated with ammonium formate (3.5 g, 55.3 mmol) and 10% Pd/C (390 mg). The reaction mixture was heated to reflux under a nitrogen atmosphere for three hours. The resulting suspension was filtered through a pad of celite and concentrated in vacuo to afford 1.8 g (yield: 96%) Compound 259A as a solid.

259B. Preparation of ((3S,4R)-1-tert-butyl 3-ethyl 4-(allyloxycarbonyl)piperidine-1,3-dicarboxylate

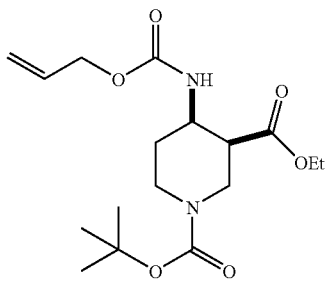

A solution of 259A (900 mg, 3.3 mmol) in $CH_2Cl_2$ (20 mL) was treated with triethylamine (0.64 mL, 4.62 mmol) and allylchloroformate (0.35 mL, 3.96 mmol) at room temperature. The mixture was stirred for four hours, then washed with 0.1 N HCl (2×10 mL), 1N NaOH (2×10 mL) and brine (10 mL). The organic layer was dried ($Na_2SO_4$), filtered and concentrated in vacuo to give 680 mg (yield: 58%) of Compound 259B as an oil.

259C. Preparation of (3S,4R)-ethyl 4-(allyloxycarbonyl)piperidine-3-carboxylate

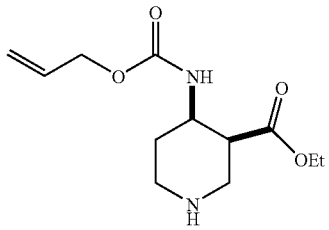

A solution of 259B (680 mg, 1.9 mmol) in $CH_2Cl_2$ (10 mL) was treated with TFA (1 mL) at room temperature. The reaction mixture was stirred for 16 hours, then concentrated. The residues was dissolved in EtOAc (20 mL) and washed with saturated aqueous $NaHCO_3$ (2×20 mL), dried ($Na_2SO_4$), filtered and concentrated in vacuo to afford 170 mg of Compound 259C.

259D. Preparation of (3S,4R)-methyl 4-(allyloxycarbonyl)-1-((4-(3-ethynylphenylamino)-pyrrolo[1,2-f][1,2,4]triazin-5-yl)methyl)piperidine-3-carboxylate 259F. Preparatio of allyl (3S,4R)-1-((4-(3-ethynylphenylamino)pyrrolo[1,2-f][1,2,4]-triazin-5-yl)methyl)-3-(methylcarbamoyl)piperidin-4-ylcarbamate

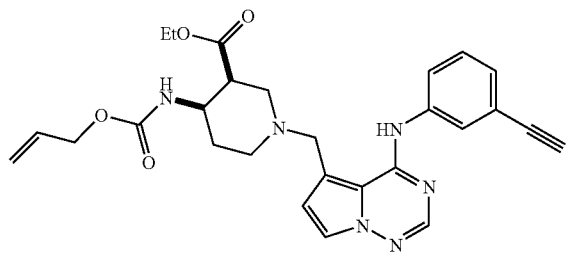
259D

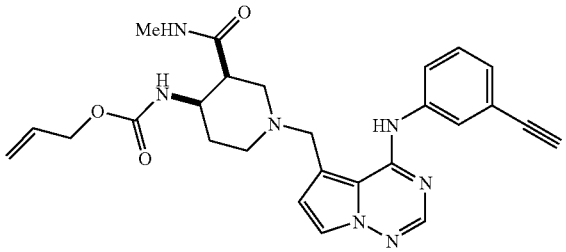
259F

A suspension of 259C (50 mg, 0.2 mmol) and N,N-diethyl-N-((4-(3-ethynylphenyl-amino)pyrrolo[1,2-f][1,2,4]triazin-5-yl)methyl)ethanaminium bromide (82 mg, 0.18 mmol) in acetonitrile (2 mL) were treated with DIEA (31 µL, 0.18 mmol). The mixture was heated to 65° C. for 6.0 hours, cooled to room temperature and concentrated. The crude material was purified by radial chromatography (SiO$_2$, 2 mm plate, 100% CH$_2$Cl$_2$ to 1% MeOH/CH$_2$Cl$_2$ gradient) to afford 63 mg (yield: 70%) of Compound 259D.

259E. Preparation of (3S,4R)-4-(allyloxycarbonyl)-1-((4-(3-ethynylphenylamino)-pyrrolo[1,2-f][1,2,4]triazin-5-yl)methyl)piperidine-3-carboxylic acid A solution of 259E (56 mg, 0.12 mmol) in DMF (3 mL) was treated sequentially with methylamine (2M in THF, 0.12 mL, 0.24 mmol), DIEA (0.02 mL, 0.12 mmol) and Bop Reagent (68 mg, 0.13 mmol). The reaction mixture was stirred for 18 hours at room temperature. The resulting mixture was diluted with EtOAc (25 mL), washed with brine (3×15 mL), dried (Na$_2$SO$_4$), filtered and concentrated in vacuo. The crude 259E (71 mg) was used without further purification.

A solution of 259F (71 mg, 0.15 mmol) in THF(3 mL) was degassed with argon and treated with diethylamine (28 mg, 0.38 mmol) and Pd(PPh$_3$)$_4$ (17 mg, 0.02 mmol). The reaction was stirred under an argon atmosphere for 2.0 hours, then concentrated in vacuo and purified by preparative HPLC to afford 14 mg of Compound 259. It had an analytical HPLC retention time=2.10 min (YMC S5 ODS 4.6×50 mm, 10–90% aqueous methanol containing 0.2% H$_3$PO$_4$, 4 min gradient, monitored at 220 nm) [M+H]$^+$=404.

EXAMPLE 260

(3S,4S)-4-amino-1-((4-(3-methoxyphenylamino)pyrrolo[1,2-f][1,2,4]triazin-5-yl)methyl)-N-methylpiperidine-3-carboxamide

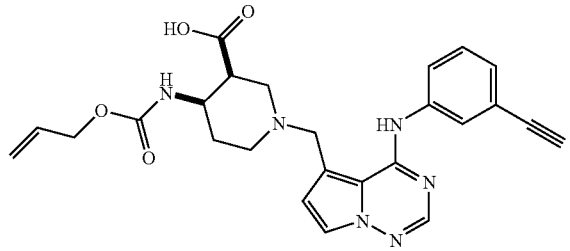
259E

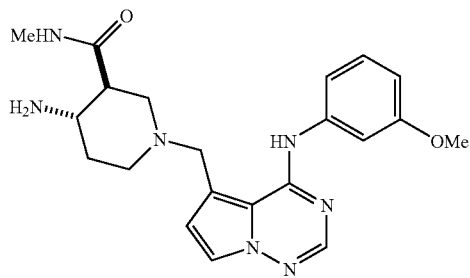
260

A solution of 259D (63 mg, 0.13 mmol) in THF/MeOH (1:1, 4 mL) was treated with a solution of LiOH monohydrate (17 mg, 0.39 mmol) at room temperature. The reaction mixture was stirred for 18 hours, then concentrated to 0.5 mL volume. The residues was diluted with water (5 mL) and brought to pH 6 with saturated aqueous NH$_4$Cl solution. The mixture was extracted with EtOAc (2×10 mL), the organic layers were dried (Na$_2$SO$_4$) filtered and concentrated in vacuo to afford 56 mg (yield: 92%) of Compound 259E.

260A. Preparation of (3S,4S)-1-tert-butyl 3-methyl 4-((S)-1-phenylethylamino)-piperidine-1,3-dicarboxylate

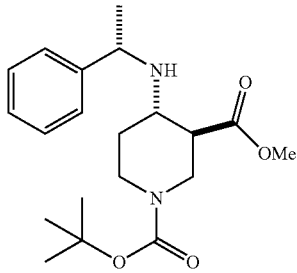

260A

A solution of 258A (4.50 g, 12.4 mmol) in methanol (124 mL) at room temperature was treated with 25% NaOMe in methanol (8.04 mL). This reaction mixture was heated to 50° C. for 3.0 hours, cooled to room temperature, and then concentrated in vacuo. The oily residue was dissolved in dichloromethane (200 mL), and washed with 20% NH₄Cl (2×75 mL). The organic layer was dried over Na₂SO₄ and concentrated in vacuo. The residue was purified by flash chromatography (10 to 25% EtOAc/hexanes) on silica gel to give 1.50 g (yield: 30%) of Compound 260A as an oil.

260B. Preparation of (3S,4S)-1-tert-butyl 3-methyl 4-aminopiperidine-1,3-dicarboxylate

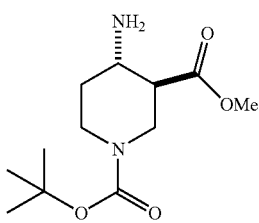

260B

A solution of 260A (1.10 g, 3.03 mmol) in MeOH (31 mL) at room temperature was treated with ammonium formate (1.51 g, 24.3 mmol) and 10% Pd/C (110 mg). The reaction mixture was heated to reflux for 14 hours then cooled to room temperature. The solid material was removed by filtration and washed with MeOH. The filtrate was concentrated in vacuo to give 0.75 g (yield: 96%) of Compound 260B as an oil.

260C. Preparation of (3S,4S)-1-tert-butyl 3-methyl 4-(benzyloxycarbonyl)piperidine-1,3-dicarboxylate

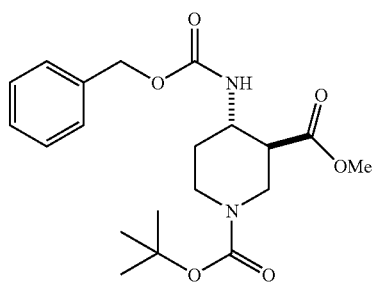

260C

A solution of 260B (0.75 g, 2.90 mmol) in dichloromethane (30 mL) at 0° C. was treated with triethylamine (0.35 g, 3.48 mmol) and N-(benzyloxycarbonyoxy) succinimide (0.72 g, 2.90 mmol). The reaction mixture was allowed to warm to room temperature and was stirred for 16 hours. The reaction mixture was diluted with dichloromethane, washed with 10% citric acid (2×50 mL), then saturated NaHCO₃ (2×50 mL). The organic layer was dried over Na₂SO₄ and concentrated in vacuo to give 1.01 g (yield: 89%) of Compound 260C as an oil. It was used in the next step without further purification.

260D. Preparation of (3S,4S)-methyl 4-(benzyloxycarbonyl)piperidine-3-carboxylate

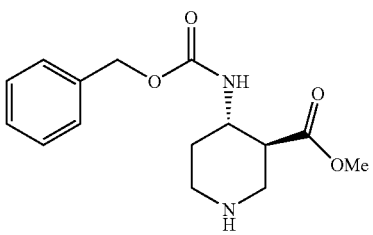

260D

A solution of 260C (1.01 g, 2.58 mmol) in dichloromethane (50 mL) at 0° C. was treated with TFA (5 mL). The reaction mixture was stirred at 0° C. for 1.0 hour then allowed to slowly warm to room temperature and stirred for an additional 2.0 hours. The mixture was concentrated, and then azeotropically evaporated with MeOH and toluene. The residue was dissolved in dichloromethane and washed with saturated NaHCO₃ (2×50 mL). The organic layer was dried over Na₂SO₄ and concentrated in vacuo to give 0.61 g (yield: 81%) of Compound 260D as an oil. It was used in the next step without further purification.

260E. Preparation of (3S,4S)-methyl 4-(benzyloxycarbonyl)-1-((4-(3-methoxyphenyl-amino)pyrrolo[1,2-f][1,2,4]triazin-5-yl)methyl)piperidine-3-carboxylate

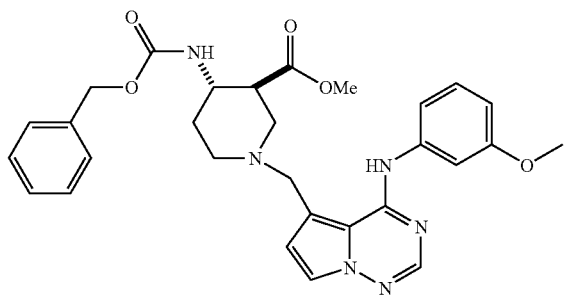

260E

A reaction mixture of 260D (0.18 g, 0.61 mmol), 4-(3-methoxyphenylamino)-pyrrolo[1,2,4]trizin-5-ylmethyl triethylammonium bromide (0.29 g, 0.61 mmol), and diisopropylethyl amine (79 mg, 0.61 mmol) in MeCN (6 mL) was heated to 55° C. for 12 hours and concentrated in vacuo. The residue was dissolved in dichloromethane and washed with water (2×50 mL). The dichloromethane portion was dried over Na₂SO₄ and concentrated in vacuo to give 0.33 g (yield: 99%) of Compound 260E as an oil. It was used in the next step without further purification. (M+H)⁺=545

260F. Preparation of (3S,4S)-4-(benzyloxycarbonyl)-1-((4-(3-methoxyphenylamino)-pyrrolo[1,2-f][1,2,4]triazin-5-yl)methyl)piperidine-3-carboxylic acid

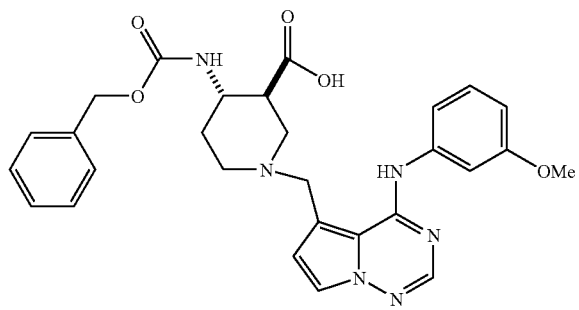

260F

A solution of 260E (95 mg, 0.18 mmol) in MeOH/THF/water (1/1/0.5 mL) at room temperature was treated with LiOH monohydrate (75 mg, 1.8 mmol). The reaction mixture was stirred for 18 hours, quenched with saturated NH$_4$Cl (5 mL), and extracted with EtOAc (3×15 mL). The EtOAc layer was dried over Na$_2$SO$_4$ and concentrated in vacuo to give 80 mg (yield: 89%) of Compound 260F as a film. It was used in the next step without further purification. Mass (M+H)$^+$=531

260G. Preparation of benzyl (3S,4S)-1-((4-(3-methoxyphenylamino)pyrrolo[1,2-f][1,2,4]triazin-5-yl)methyl)-3-(methylcarbamoyl)piperidin-4-ylcarbamate

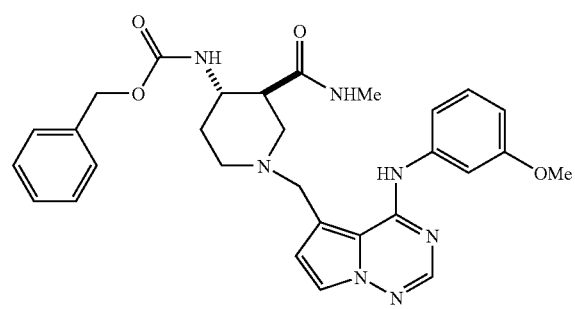

260G

A solution of 260F (40 mg, 0.075 mmol) in DMF (0.8 mL) at room temperature was treated with diisopropylethylamine (10 mg, 0.075 mmol), Bop Reagent (59 mg, 0.11 mmol), then 2N methylamine in THF (0.12 mL, 0.23 mmol). The reaction mixture was stirred for 16 hours, quenched with water, and concentrated. The resulting suspension was dissolved in MeOH, and purified by preparative HPLC (YMC ODS-A 5 um, 20×100 mm, solvent A 10% MeOH-90% H$_2$O-0.1% TFA, solvent B 90% MeOH-10% H$_2$O-0.1% TFA, gradient 0–100% B, 12 minutes). The desired fractions were concentrated to remove most of the MeOH, neutralized by saturated NaHCO$_3$ to pH 10 and extracted with EtOAc (2×50 mL). The combined organic layers were dried over Na$_2$SO$_4$ and concentrated in vacuo to give 38 mg (yield: 93%) of 260G as a solid. Mass (M+H)$^+$=544.

A solution of 260G (38 mg, 0.070 mmol) in MeOH (2 mL) at room temperature was treated with 5% Pd/C (10 mg). The reaction mixture was stirred under a hydrogen atmosphere for 16 hours. The catalyst was removed by filtration. The filtrate was concentrated in vacuo to give 25 mg (yield: 87%) of Compound 260 as a solid. It had an analytic HPLC retention time=1.71 min (Phenomenex Su C18 4.6×50 mm column 10–90% aqueous methanol containing 0.2% H$_3$PO$_4$, 4 min grad. monitored at 220 nm). Mass [M+H]$^+$=410.

EXAMPLE 261

((3R,4R)-1-((4-(3-methoxyphenylamino)pyrrolo[1,2-f][1,2,4]-triazin-5-yl)methyl)-4-((R)-1-phenylethylamino)piperidin-3-yl)methanol

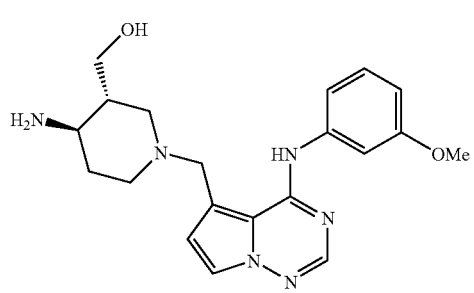

261

261A. Preparation of (3R,4R)-1-(tert-butoxycarbonyl)-4-((R)-1-phenylethylamino)-piperidine-3-carboxylic acid

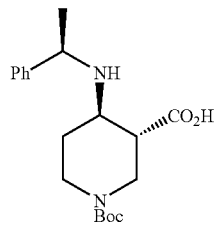

261A

A mixture of 252D (460 mg, 1.22 mmol) and NaOEt (1.25 mL, 21% wt in EtOH) in EtOH (10 ml) was stirred at 50° C. for 3 hrs, then at RT for about 48 hours. The reaction mixture was concentrated in vacuo, followed by the addition of water. The mixture was acidified with 1N HCl to pH 4–5 and the solid was collected by filtration, washed with water and dried to give 300 mg (yield: 71%) of 252A. It had an analytical HPLC retention time=2.065 min. (Chromolith SpeedROD column 4.5×50 mm, 10–90% aqueous methanol containing 0.1% TFA over 4 min, 4 mL/min, monitoring at 220 nm). Mass (M+1)$^+$=349.

261B. Preparation of (3R,4R)-1-tert-butyl 3-methyl 4-((R)-1-phenylethylamino)-piperidine-1,3-dicarboxylate

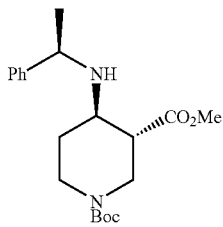

261B

To a solution of 261A (280 mg, 0.80 mmol) in 6 mL of 1:1 CH$_2$Cl$_2$/MeOH was added a solution of TMSCHN$_2$ (0.82 ml, 1.64 mmol, 2N in hexane). The mixture was stirred at room temperature for 30 min, then concentrated in vacuo and purified by flash chromatography (hexane/EtOAc: 80:20) on silica gel to give Compound 261B as an oil. It had an analytical HPLC retention time=2.187 min. (Chromolith SpeedROD column 4.5×50 mm, 10–90% aqueous methanol containing 0.1% TFA over 4 min, 4 mL/min, monitoring at 220 nm). Mass (M+1)$^+$=363.

261C. Preparation of ((3R,4R)-4-((R)-1-phenylethylamino)piperidin-3-yl)methanol

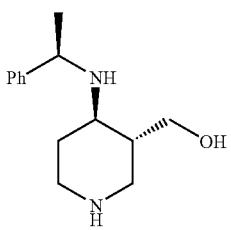

261C

To a solution of 261B (270 mg, 0.75 mmol) was added LiBH$_4$ (15.5 mg, 0.71 mmol). The mixture was heated to reflux for 1.0 hr. HPLC showed still some starting material remaining. More LiBH$_4$ (15.5 mg, 0.71 mmol) was added, and the mixture was heated for another 2.0 hrs. After cooling to room temperature, ice water was added, and the mixture was concentrated in vacuo to remove the THF. The aqueous residue was extracted with EtOAc (×3) and the combined extracts were dried (Na$_2$SO$_4$), and concentrated in vacuo. The residue was taken into 2 mL of CH$_2$Cl$_2$ and 2 mL of TFA was added. The mixture was stirred at room temperature for 30 min. The mixture was concentrated in vacuo, followed by drying under high vacuum overnight to afford 261C as an oil. It had an analytical HPLC retention time=0.590 min. (Chromolith SpeedROD column 4.5×50 mm, 10–90% aqueous methanol containing 0.1% TFA over 4 min, 4 mL/min, monitoring at 220 nm) and a LC/MS M$^+$+1=235. This material was used directly in the next reaction step without further purification.

261D. Preparation of ((3R,4R)-1-((4-(3-methoxyphenylamino)pyrrolo[1,2-f][1,2,4]-triazin-5-yl)methyl)-4-((R)-1-phenylethylamino)piperidin-3-yl)methanol

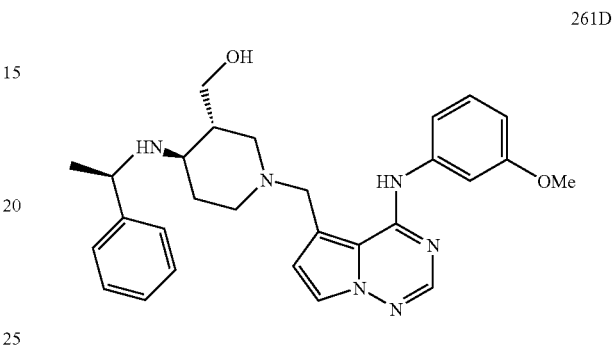

261D

Compound 261D was prepared from 261C in a similar process as used for Compound 146E. It had an analytical HPLC retention time=1.761 min. (Chromolith SpeedROD column 4.5×50 mm, 10–90% aqueous methanol containing 0.1% TFA over 4 min, 4 mL/min, monitoring at 220 nm) and a LC/MS M$^+$+1=487.

A mixture of 261D (160 mg, 0.33 mmol), 10% Pd/C (39 mg) and ammonium formate (166 mg, 2.63 mmol) in MeOH (15 ml) was heated to reflux for 1.0 hr. After cooling to room temperature, the catalyst was removed by filtration and the filtrate was concentrated in vacuo. The residue was dissolved in water, basified with aqueous NaHCO$_3$ and extracted with EtOAc (3×). The combined extracts were dried (Na$_2$SO$_4$) and concentrated in vacuo to give 64 mg (yield: 51%) of Compound 261 as a solid (64 mg, 51%). It had an analytical HPLC retention time=1.137 min. (Chromolith SpeedROD column 4.5×50 mm, 10–90% aqueous methanol containing 0.1% TFA over 4 min, 4 mL/min, monitoring at 220 nm) and a LC/MS M$^+$+1=383.

EXAMPLE 262 rac-(3R,4R)-1-({4-[(3-methoxyphenyl)amino]pyrrolo[2,1-f][1,2,4]triazin-5-yl}methyl)piperidine-3,4-diamine

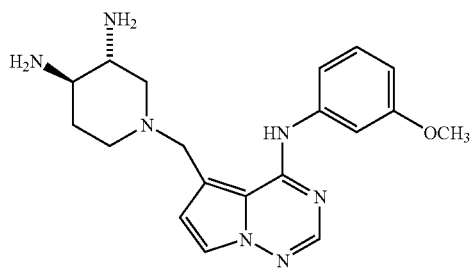

262A. Preparation of (3R,4R)-tert-butyl 4-(benzyloxycarbonyl)-3-hydroxypiperidine-1-carboxylate

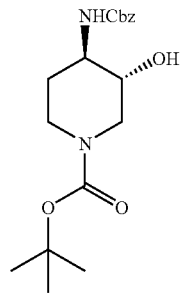

262A

To a stirred mixture of Compound 249A (1.40 g, 6.47 mmoL) in 10 mL of $CH_2Cl_2$ was added $Et_3N$ (1.08 mL, 7.76 mmoL), followed by Cbz-OSu (1.69 g, 6.80 mmoL). The reaction mixture was stirred at room temperature for 16 hrs and then diluted with 300 mL of EtOAc. The organic layer was washed with 5% citric acid solution (2×40 mL), 5% $K_2CO_3$ solution (2×40 mL) and brine (40 mL) and dried ($MgSO_4$). The residue was filtered and concentrated in vacuo to afford 2.25 g (yield: 99%) of Compound 262A. It had an analytical HPLC retention time=3.02 min. (Phenomenox S5 C18-HC 4.6×50 mm column, 10–90% aqueous methanol over 4 minutes containing 0.1% TFA, 4 ml/min, monitoring at 220 nm) and a LC/MS $M^++1=351$.

262B/C. Preparation of (3R,4R)-tert-butyl 3-azido-4-(benzyloxycarbonyl) piperidine-1-carboxylate

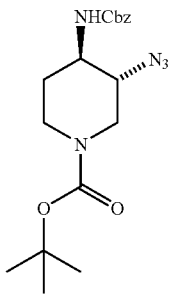

262B (cis)

Diastereomer A

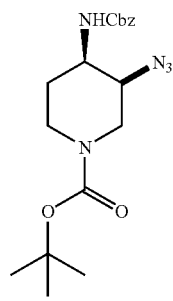

262C (trans)

Diastereomer B

To a stirred solution of Compound 262A (2.23 g, 6.36 mmoL) and $Et_3N$ (1.20 mL, 0.83 mmoL) in 30 mL of $CH_2Cl_2$ under nitrogen at 0° C. was added and methanesulfonyl chloride (0.49 mL, 6.36 mmoL) over 5 min. The mixture was stirred at 0° C. for 35 min and then diluted with 40 mL of $CH_2Cl_2$. The mixture was washed with water (2×25 mL), brine (20 mL) and dried ($MgSO_4$). The mixture was filtered and concentrated in vacuo to afford the crude mesylate. To the mesylate in 20 mL of DMSO was added $NaN_3$ (1.65 g, 25.5 mmoL). The mixture was heated at 90° C. for 17 h and cooled to room temperature. The mixture was diluted with 200 mL of EtOAc and washed with water (4×200 mL), saturated $NaHCO_3$ solution (40 mL), brine (40 mL) and dried ($MgSO_4$). Filtration, concentration in vacuo, followed by flash chromatography (15–50% EtOAc in hexane) on silica gel gave 696 mg (29%) of 262B (Diastereomer A, Rf=0.65) and 262C (Diastereomer B, Rf=0.70). 262B had an analytical HPLC retention time=3.51 min. (Phenomenox S5 C18-HC 4.6×50 mm column, 10–90% aqueous methanol over 4 minutes containing 0.1% TFA, 4 ml/min, monitoring at 220 nm) and a LC/MS $M^++1=376$. 262C had an analytical HPLC retention time=3.51 min. (Phenomenox S5 C18-HC 4.6×50 mm column, 10–90% aqueous methanol over 4 minutes containing 0.1% TFA, 4 ml/min, monitoring at 220 nm) and a LC/MS $M^++1=376$.

262D. Preparation of benzyl (3R,4R)-3-azido-1-((4-(3-methoxyphenylamino) pyrrolo[1,2-f][1,2,4]triazin-5-yl)methyl)piperidin-4-ylcarbamate

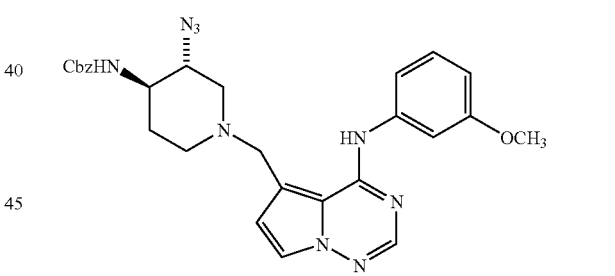

262D

Compound 262D was prepared from Compound 262B in a similar process as described for Compound 247A. It had an analytical HPLC retention time=2.96 min. (Phenomenox S5 C18-HC 4.6×50 mm column, 10–90% aqueous methanol over 4 minutes containing 0.1% TFA, 4 ml/min, monitoring at 220 nm) and a LC/MS $M^++1=528$.

Compound 262 was prepared from Compound 262D in a similar process as described for Compound 249A. It had an analytical HPLC retention time=1.27 min. (Phenomenox S5 C18-HC 4.6×50 mm column, 10–90% aqueous methanol over 4 minutes containing 0.1% TFA, 4 ml/min, monitoring at 220 nm) and a LC/MS $M^++1=368$.

EXAMPLE 263 rac-N-[(3R,4R)-4-amino-1-({4-[(3-methoxyphenyl)amino]pyrrolo[2,1-f][1,2,4]triazin-5-yl}methyl)piperidin-3-yl]urea

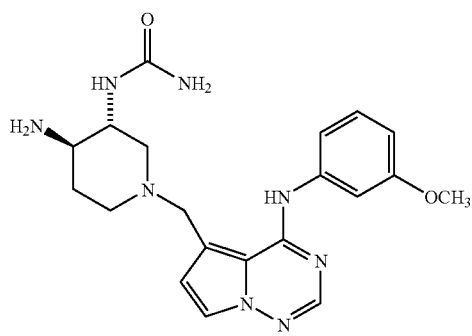

263A. Preparation of benzyl (3R,4R)-3-amino-1-((4-(3-methoxyphenylamino) pyrrolo[1,2-f][1,2,4]triazin-5-yl)methyl)piperidin-4-ylcarbamate (Chiral, Diastereomer A):

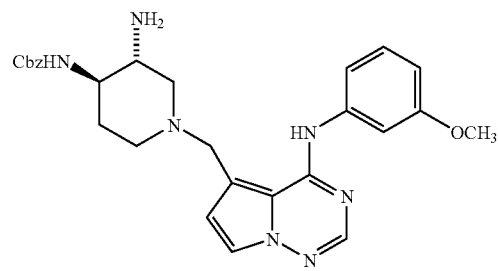

Compound 263A was prepared from Compound 262C in a similar process as described as used for Compound 146E. It had an analytical HPLC retention time 2.71 min. (Phenomenox S5 C18-HC 4.6×50 mm column, 10–90% aqueous methanol over 4 minutes containing 0.1% TFA, 4 ml/min, monitoring at 220 nm) and a LC/MS M$^+$+1=502.

263B. Preparation of benzyl (3R,4R)-1-((4-(3-methoxyphenylamino)pyrrolo[1,2-f][1,2,4]triazin-5-yl)methyl)-3-ureidopiperidin-4-ylcarbamate

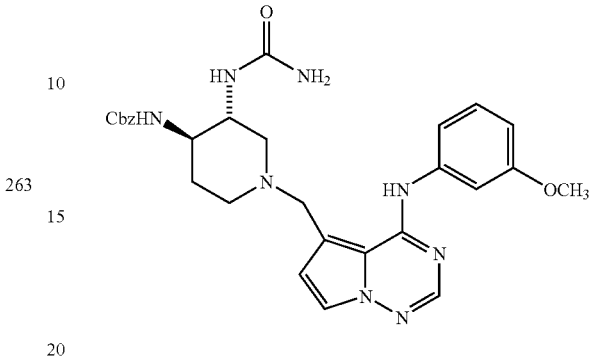

To a stirred mixture of Compound 263A (77.0 mg, 0.15 mmoL) in 2 mL of CH$_2$Cl$_2$ at 0° C. was added trichloroacetylisocyanate (28.9 mg, 0.18 mmoL). The mixture was stirred at 0° C. for 30 min, and 1 mL of methanol was added. This mixture was then concentrated in vacuo to give a crude oil. This crude material was dissolved in 3 mL of methanol and 2 mL of 20% K$_2$CO$_3$ solution was added. The mixture was stirred at room temperature for 2 h, then diluted with 10 mL of water. It was concentrated in vacuo to remove methanol and then extracted with EtOAc (3×15 mL). The combined EtOAc extracts were washed with brine (10 mL) and dried (MgSO$_4$). Filtration followed by concentration in vacuo afforded 70 mg (yield: 84%) of Compound 263B. It had an analytical HPLC retention time=2.51 min. (Phenomenox S5 C18-HC 4.6×50 mm column, 10–90% aqueous methanol over 4 minutes containing 0.1% TFA, 4 ml/min, monitoring at 220 nm) and a LC/MS M$^+$+1=(.

Compound 263 was prepared from Compound 263B in a similar way as described for compound 249A. It had an analytical HPLC retention time=1.32 min. (Phenomenox S5 C 18-HC 4.6×50 mm column, 10–90% aqueous methanol over 4 minutes containing 0.1% TFA, 4 ml/min, monitoring at 220 nm) and a LC/MS M$^+$+1=411.

EXAMPLE 264 rac-N-[(3R,4R)-4-amino-1-({4-[(3-methoxyphenyl)amino]pyrrolo[2,1-f][1,2,4]triazin-5-yl}methyl)piperidin-3-yl]methanesulfonamide

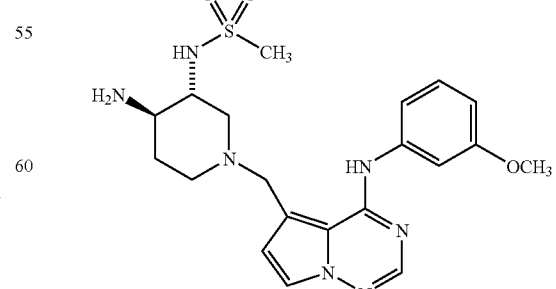

264A. Preparation of benzyl 7-(methylsulfonyl)-3,7-diaza-bicyclo[4.1.0]heptane-3-carboxylate (Racemic)

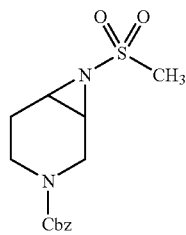

264A

To a stirred mixture of benzyl 3,7-diaza-bicyclo[4.1.0]heptane-3-carboxylate (410 mg, 1.77 mmoL, prepared as shown in Tetrahedron Letters, 43(23), 4289–4293, 2002) in 5 mL of $CH_2Cl_2$ was added triethylamine (0.74 mL, 5.31 mmoL), followed by methanesulfonyl chloride (0.18 mL, 2.30 mmoL). The mixture was stirred at room temperature for 2.5 h and then diluted with 120 mL of EtOAc. This mixture was washed with 5% citric acid solution (3×30 mL), saturated $NaHCO_3$ solution (30 mL), and brine (30 mL). The organic layer was dried ($MgSO_4$), filtered and concentrated in vacuo to give Compound 264A in quantitative yield. It had an analytical HPLC retention time=2.56 min. (Phenomenox S5 C18-HC 4.6×50 mm column, 10–90% aqueous methanol over 4 minutes containing 0.1% TFA, 4 ml/min, monitoring at 220 nm) and a LC/MS $M^++Na=333$.

264B. Preparation of (3R,4R)-rel-benzyl 4-azido-3-(methylsulfonamido)piperidine-1-carboxylate:

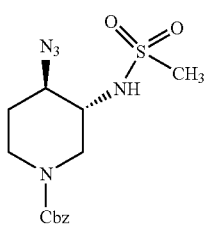

264B

To a stirred mixture of compound 264A (549 mg, 1.77 mmoL) in 4 mL of DMSO was added $NaN_3$ (458 mg, 7.08 mmoL). The mixture was stirred at room temperature for 2 h, and diluted with 80 mL of EtOAc. The mixture was washed with water (3×100 mL), saturated $NaHCO_3$ solution (40 mL), and brine (40 mL). The EtOAc layer was dried ($MgSO_4$), filtered and concentrated in vacuo to give 530 mg (yield: 85%) of Compound 264B. It had an analytical HPLC retention time=2.90 min. (Phenomenox S5 C18-HC 4.6×50 mm column, 10–90% aqueous methanol over 4 minutes containing 0.1% TFA, 4 ml/min, monitoring at 220 nm) and a LC/MS $M^++1=354$.

264C. Preparation of (3R,4R)-rel-benzyl 4-amino-3-(methylsulfonamido)piperidine-1-carboxylate:

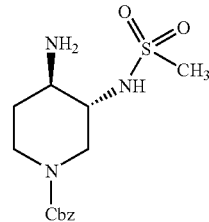

264C

To a stirred mixture of Compound 264B (530 mg, 1.50 mmoL) in 6 mL of THF and 1 mL of water was added $Ph_3P$ (900 mg, 3.43 mmoL). The reaction mixture was heated at 70° C. for 15 h and cooled to room temperature. This mixture was concentrated in vacuo, diluted with 15 mL of 2N HCl solution, and then washed with $CHCl_3$ (3×20 mL). The aqueous was basified to pH 12 by the addition of 50% NaOH solution, saturated with NaCl, and then extracted with EtOAc (3×25 mL). The combined EtOAc extracts were washed with brine (15 mL), dried ($MgSO_4$), filtered and concentrated in vacuo to give 490 mg (yield: 100%) of Compound 264C. It had an analytical HPLC retention time=1.67 min. (Phenomenox S5 C18-HC 4.6×50 mm column, 10–90% aqueous methanol over 4 minutes containing 0.1% TFA, 4 ml/min, monitoring at 220 nm) and a LC/MS $M^++1=328$.

264D. Preparation of tert-butyl (3R,4R)-rel-1-((4-(3-methoxyphenylamino)pyrrolo[1,2-f][1,2,4]triazin-5-yl)methyl)-3-(methylsulfonamido)piperidin-4-ylcarbamate

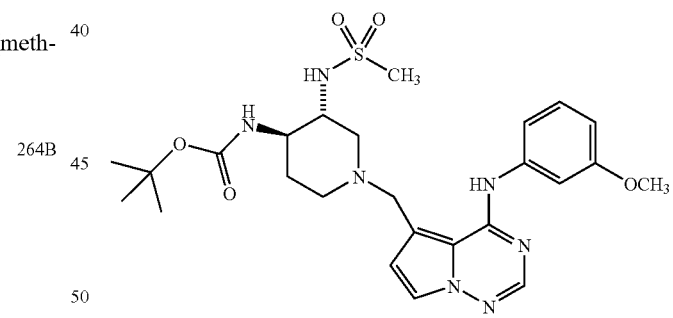

264D

To a stirred solution of compound 264C (490 mg, 1.50 mmoL) in 6 mL of $CH_2Cl_2$ was added $Et_3N$ (0.63 mL, 4.50 mmoL), followed by di-t-butyl dicarbonate (390 mg, 1.80 mmoL). The reaction mixture was stirred at room temperature for 3 h. The mixture was diluted with 60 mL of EtOAc, washed with saturated $NaHCO_3$ solution (2×15 mL) and brine (15 mL). The organic phase was dried ($MgSO_4$), filtered and concentrated in vacuo to give a crude intermediate. The crude intermediate was purified by flash chromatography (hexane-EtOAc) on silica gel to give 131 mg of pure meterial. To this intermediate in 6 mL of methanol under nitrogen was added 20% $Pd(OH)_2/C$ (30 mg). The reaction mixture was purged with hydrogen several times and stirred under hydrogen atmosphere for 18 h. The catalyst was removed by filtration using a 4 μM polycarbonate film and rinsed with MeOH (4×10 mL). The combined filtrates were concentrated in vacuo to give 89 mg of crude amine intermediate.

Compound 264D was prepared from this intermediate in a similar process as described for 146E. It had an analytical HPLC retention time=2.72 min. (Phenomenox S5 C18-HC 4.6×50 mm column, 10–90% aqueous methanol over 4 minutes containing 0.1% TFA, 4 ml/min, monitoring at 220 nm) and a LC/MS M$^+$+1=546.

To a stirred solution of compound 264D (120 mg, 0.22 mmoL) in 3 mL of CH$_2$Cl$_2$ was added TFA (2.5 mL, 32.4 mmoL). The mixture was stirred at room temperature for 40 min, concentrated in vacuo, and purified by a prep HPLC to give 71 mg (yield: 73%) of Compound 264. It had an analytical HPLC retention time=1.54 min. (Phenomenox S5 C18-HC 4.6×50 mm column, 10–90% aqueous methanol over 4 minutes containing 0.1% TFA, 4 ml/min, monitoring at 220 nm) and a LC/MS M$^+$+1=446.

EXAMPLE 265

N-[(3S,4R)-4-amino-1-({4-[(3-methoxyphenyl)amino]pyrrolo[2,1-f][1,2,4]triazin-5-yl}methyl)piperidin-3-yl]methanesulfonamide

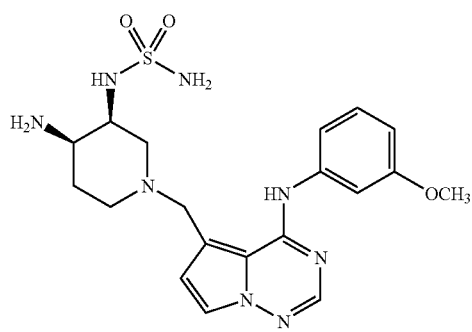

Preparation of compound 265A

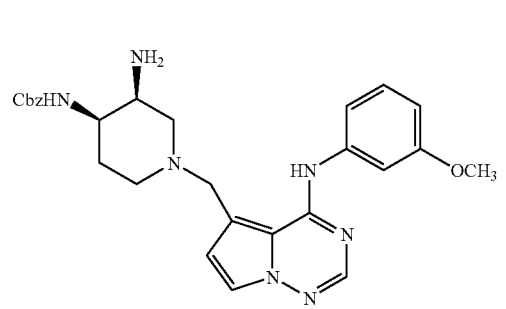

Compound 265A was prepared from compound 262C (chiral, regioisomer B) in a similar way as described for compound 262D. It had an analytical HPLC retention time=2.73 min. (Phenomenox S5 C18-HC 4.6×50 mm column, 10–90% aqueous methanol over 4 minutes containing 0.1% TFA, 4 ml/min, monitoring at 220 nm) and a LC/MS M$^+$+1=502.

Preparation of compound 265B

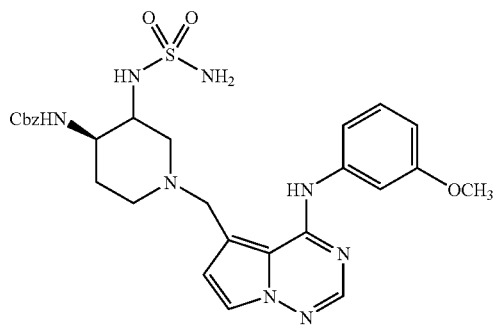

To a stirred mixture of compound 265A (60.0 mg, 0.12 mmoL) and Et$_3$N (0.05 mL, 0.36 mmoL) in 4 mL of DCM was added methanesulfonyl chloride (15.0 mg, 0.13 mmoL). This reaction mixture was stirred at room temperature for 20 h and then diluted with 100 mL of EtOAc. The mixture was washed with saturated NaHCO$_3$ solution (20 mL) and brine (20 mL). The EtOAc layer was dried (MgSO$_4$), filtered and concentrated in vacuo to give 70 mg of compound 265B in a quantitative yield. Compound 265B has an analytical HPLC retention time=2.61 min. (Phenomenox S5 C18-HC 4.6×50 mm column, 10–90% aqueous methanol over 4 minutes containing 0.1% TFA, 4 ml/min, monitoring at 220 nm) and a LC/MS M$^+$+1=580.

Compound 265 was prepared from compound 265B (chiral, regioisomer B) in a similar way as described for Compound 249A. The structure of Compound 265 was assigned based on comparison of $^1$H-NMR from that of Compound 264. The compound had an analytical HPLC retention time=1.50 min. (Phenomenox S5 C18-HC 4.6×50 mm column, 10–90% aqueous methanol over 4 minutes containing 0.1% TFA, 4 ml/min, monitoring at 220 nm) and a LC/MS M$^+$+1=446.

EXAMPLE 266

N-[(3R,4R)-4-amino-1-({4-[(3-methoxyphenyl)amino]pyrrolo[2,1-f][1,2,4]triazin-5-yl}methyl)piperidin-3-yl]methanesulfonamide (Enantiomer A)

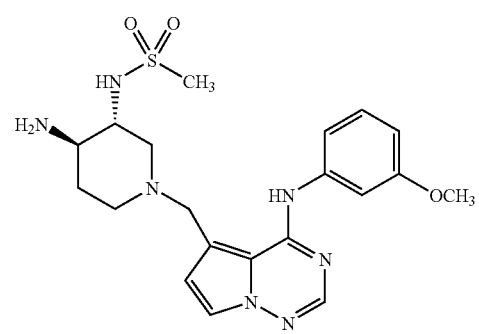

(Enantiomer A)

Compound 266 was obtained from 264 by a chrial preparative HPLC separation as the first eluted peak with >99% ee. Compound 127A an HPLC retention time=6.3 min (Chiral Pak, AD 250×4.6 mm column, 10 micron, 220 nM, 0.8 mL/min, EtOH as eluant). LC/MS M++1=446.

EXAMPLE 267

N-[(3S,4S)-4-amino-1-({4-[(3-methoxyphenyl)amino]pyrrolo[2,1-f][1,2,4]triazin-5-yl}methyl)piperidin-3-yl]methanesulfonamide (Enantiomer B)

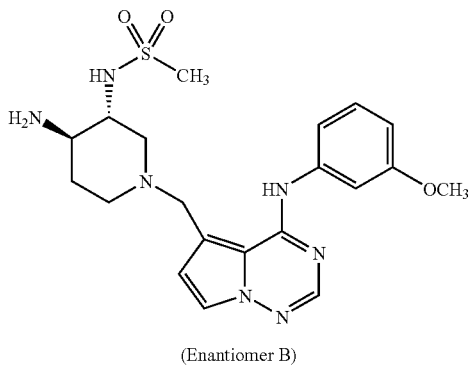

(Enantiomer B)

Compound 267 was obtained from 264 by a chiral preparative HPLC separation as the second eluted peak with >99% ee. Compound 267 had an HPLC retention time=7.9 min (Chiral Pak, AD 250×4.6 mm column, 10 micron, 220 nM, 0.8 mL/min, EtOH as eluant). LC/MS M++1=446.

We claim:
1. A compound selected from the group consisting of
5-[(4-Amino-1-piperidinyl)methyl]-N-(3-chloro-4-fluorophenyl)pyrrolo[2,1-f][1,2,4]triazine-4-amine,
5-[(4-Amino-1-piperidinyl)methyl]-N-2-naphthalenylpyrrolo[2,1-f][1,2,4]triazin-4-amine,
5-[(4-Amino-1-piperidinyl)methyl]-N-phenylpyrrolo[2,1-f][1,2,4]triazin-4-amine,
5-[(4-Amino-1-piperidinyl)methyl]-N-(3-methoxyphenyl)pyrrolo[2,1-f][1,2,4]triazin-4-amine,
5-[(4-Amino-1-piperidinyl)methyl]-N-(3-ethynylphenyl)pyrrolo[2,1-f][1,2,4]triazin-4-amine,
5-[(4-aminopiperidin-1-yl)methyl]-N-(4-fluoro-3-methoxyphenyl)pyrro-lo[2,1-f][1,2,4]triazin-4-amine,
(3R,4R)-4-amino-1-[[4-[(3-chloro-4-fluorophenyl)amino]pyrrolo[2,1-f][1,2,4]triazin-5-yl]methyl]piperidin-3-ol,
(3S,4S)-4-amino-1-[[4-[(3-chloro-4-fluorophenyl)amino]pyrrolo[2,1-f][1,2,4]triazin-5-yl]methyl]piperidin-3-ol,
(3R,4R)-4-amino-1-[[4-[(3-methoxyphenyl)amino]pyrrolo[2,1-f][1,2,4]triazin-5-yl]methyl]piperidin-3-ol,
(3S,4S)-4-amino-1-[[4-[(3-methoxyphenyl)amino]pyrrolo[2,1-f][1,2,4]triazin-5-yl]methyl]piperidin-3-ol,
(3R,4R)-4-amino-1-[[4-[(3-methoxy-4-fluorophenyl)amino]pyrrolo[2,1-f][1,2,4]triazin-5-yl]methyl]piperidin-3-ol,
(3R,4R)-4-amino-1-({4-[(3-ethynylphenyl)-amino]pyrrolo[2,1-f]-[1,2,4]-triazin-5-yl}-methyl)piperidin-3-ol,
(3R,4R)-4-amino-1-({4-[(3-ethoxyphenyl)-amino]-pyrrolo[2,1-f]-[1,2,4]triazin-5-yl}-methyl)piperidin-3-ol
(3R,4R)-4-amino-1-{[4-(2-naphthylamino)-pyrrolo[2,1-f][1,2,4]-triazin-5-yl]methyl}piperidin-3-ol,
(3R,4R)-4-amino-1-({4-[(3-methoxy-4-methyl-phenyl)amino]pyrrolo[2,1-f][1,2,4]triazin-5-yl}-methyl)piperidin-3-ol,
(3R,4R)-4-amino-1-({4-[(3-bromophenyl)amino]pyrrolo[2,1-f][1,2,4]-triazin-5-yl}methyl)-piperidin-3-ol,
(3R,4R)-4-amino-1-({4-[(3-fluoro-5-methoxy-phenyl)amino]pyrrolo[2,1-f][1,2,4]triazin-5-yl}-methyl)piperidin-3-ol,
(3S,4R)-4-amino-1-({4-[(3-methoxyphenyl)amino]pyrrolo[2,1-f][1,2,4]triazin-5-yl}methyl)piperidin-3-ol,
(3R,4S)-4-amino-1-({4-[(3-methoxyphenyl)amino]pyrrolo[2,1-f][1,2,4]triazin-5-yl}methyl)piperidin-3-ol
(3S,4R)-4-amino-1-({4-[(3-chlorophenyl)amino]-pyrrolo[2,1-f][1,2,4]-triazin-5-yl}methyl)-piperidin-3-ol,
(3S,4R)-4-amino-1-({4-[(3-chloro-4-fluoro-phenyl)amino]pyrrolo[2,1-f][1,2,4]triazin-5-yl}-methyl)piperidin-3-ol,
(3S,4R)-4-amino-1-({4-[(3-ethynylphenyl)amino]pyrrolo[2,1-f][1,2,4]triazin-5-yl}methyl)piperidin-3-ol,
(3R,4S)-4-amino-1-({4-[(3-ethynylphenyl)-amino]pyrrolo[2,1-f][1,2,4]triazin-5-yl}methyl)piperidin-3-ol,
(3R,4S)-4-amino-1-({4-[(3-chlorophenyl)amino]pyrrolo[2,1-f][1,2,4]-triazin-5-yl}methyl)-piperidin-3-ol,
(3R,4R)-4-amino-1-({4-[(3-methoxyphenyl)amino]pyrrolo[2,1-f][1,2,4]triazin-5-yl}methyl)piperidin-3-yl carbamate,
(3R,4R)-4-amino-1-({4-[(3-ethynylphenyl)-amino]pyrrolo[2,1-f][1,2,4]triazin-5-yl}-methyl)piperidin-3-yl carbamate,
(3R,4R)-4-amino-1-({4-[(3-chloro-4-fluoro-phenyl)amino]pyrrolo[2,1-f][1,2,4]triazin-5-yl}-methyl)piperidin-3-yl carbamate,
(3S,4R)-4-amino-1-({4-[(3-chloro-4-fluoro-phenyl)amino]pyrrolo[2,1-f][1,2,4]triazin-5-yl}-methyl)piperidin-3-yl carbamate,
(3S,4R)-4-amino-1-({4-[(3-ethynylphenyl)-amino]pyrrolo[2,1-f][1,2,4]triazin-5-yl}-methyl)piperidin-3-yl carbamate,
(3S,4R)-4-amino-1-({4-[(3-methoxyphenyl)amino]pyrrolo[2,1-f][1,2,4]triazin-5-yl}methyl)-3-methylpiperidin-3-ol,
(3R/S,5R/S)-4-amino-1-({4-[(3-methoxyphenyl)amino]pyrrolo[2,1-f][1,2,4]triazin-5-yl}methyl)piperidine-3,5-diol,
(3S,5S)-4-amino-1-({4-[(4-fluoro-3-methoxy-phenyl)amino]pyrrolo[2,1-f][1,2,4]triazin-5-yl}-methyl)piperidine-3,5-diol,
(3R,5R)-4-amino-1-({4-[(3-ethynylphenyl)-amino]pyrrolo[2,1-f][1,2,4]triazin-5-yl}methyl)piperidine-3,5-diol,
5-{[(3R,4R)-4-amino-3-methoxypiperidin-1-yl]methyl}-N-(3-methoxyphenyl)pyrrolo[2,1-f][1,2,4]triazin-4-amine,
5-(((4aR,8aR)-rel-hexahydro-1H-pyrido[3,4-b][1,4]oxazin-6(7H)-yl)methyl)-N-(3-methoxyphenyl)pyrrolo[1,2-f][1,2,4]triazin-4-amine,
(3R,4R)-4-amino-1-({4-[(3-methoxyphenyl)amino]pyrrolo[2,1-f][1,2,4]triazin-5-yl}methyl)-N-(methylsulfonyl)piperidine-3-carboxamide,
(3R,4R)-4-amino-1-({4-[(3-ethynylphenyl)amino]pyrrolo[2,1-f][1,2,4]triazin-5-yl}methyl)-N-methylpiperidine-3-carboxamide,
(3R,4R)-4-amino-1-({4-[(3-methoxyphenyl)amino]pyrrolo[2,1-f][1,2,4]triazin-5-yl}methyl)-N-methylpiperidine-3-carboxamide,
(3R,4R)-4-amino-1-({4-[(3-methoxyphenyl)amino]pyrrolo[2,1-f][1,2,4]triazin-5-yl}methyl)piperidine-3-carboxamide,

((3R,4R)-1-((4-(3-methoxyphenylamino)pyrrolo[1,2-f]
[1,2,4]-triazin-5-yl)methyl)-4-((R)-1-phenylethy-
lamino)piperidin-3-yl)methanol, N-[(3R,4R)-4-amino-1-({4-[(3-methoxyphenyl)amino]
pyrrolo[2,1-f][1,2,4]triazin-5-yl}methyl)piperidin-3-
yl]urea, N-[(3R,4R)-4-amino-1-({4-[(3-methoxyphenyl)amino]
pyrrolo[2,1-f][1,2,4]triazin-5-yl}methyl)piperidin-3-
yl]methanesulfonamide, and N-[(3S,4R)-4-amino-1-({4-[(3-methoxyphenyl)amino]
pyrrolo[2,1-f][1,2,4]triazin-5-yl}methyl)piperidin-3-
yl]methanesulfonamide, or a pharmaceutically acceptable salt thereof.

2. A pharmaceutical composition comprising one or more compounds of claim 1 and a pharmaceutically acceptable carrier.

3. A compound having the formula

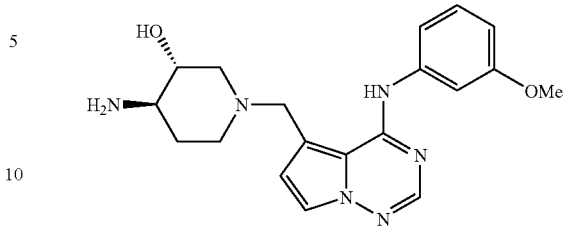

or a pharmaceutically acceptable salt thereof.

4. A pharmaceutical composition comprising the compound according to claim 3 and a pharmaceutically acceptable carrier.

* * * * *

UNITED STATES PATENT AND TRADEMARK OFFICE
CERTIFICATE OF CORRECTION

PATENT NO. : 7,141,571 B2  Page 1 of 2
APPLICATION NO. : 11/019901
DATED : November 28, 2006
INVENTOR(S) : Fink et al.

It is certified that error appears in the above-identified patent and that said Letters Patent is hereby corrected as shown below:

On the Title Page, Item (75), the last Inventor "Wen-Ching Han, Newton, PA (US)" should read: -- Wen-Ching Han, Newtown, PA (US) --

On the Title page, Item (74), Attorney, Agent, or Firm "Elliot Korsen" should read: -- Elliott Korsen --

In column 21, Lines 26-33 (Scheme 4)

"

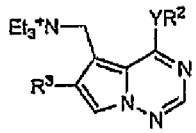

viii should read

--   --

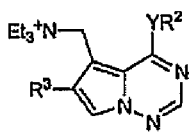

ix

In column 70, Line 48 "dry $CH_2Cl_2$ (15 mL) cooled at 0°C., was added trifluoro-" should read: -- dry $CH_2Cl_2$ (15 mL) cooled at 0°C, was added trifluoro- --

In column 70, Line 50 "C. for 15 min, then warmed to room temperature and stirred" should read: -- C for 15 min, then warmed to room temperature and stirred --

In column 71, Line 45 "Alternate preparation of Compuond 146" should read: -- Alternate preparation of Compound 146 --

UNITED STATES PATENT AND TRADEMARK OFFICE
CERTIFICATE OF CORRECTION

PATENT NO. : 7,141,571 B2
APPLICATION NO. : 11/019901
DATED : November 28, 2006
INVENTOR(S) : Fink et al.

It is certified that error appears in the above-identified patent and that said Letters Patent is hereby corrected as shown below:

In column 159, Line 46 "oxyphenyl)pyrro-lo[2, 1-*f*][1,2,4]triazin-4-amine," should read: -- oxyphenyl)pyrrolo[2,1-*f*][1,2,4]triazin-4-amine, --

Signed and Sealed this

Fourteenth Day of August, 2007

JON W. DUDAS
*Director of the United States Patent and Trademark Office*